(12) United States Patent
Beechem et al.

(10) Patent No.: US 7,282,339 B2
(45) Date of Patent: Oct. 16, 2007

(54) COMPETITIVE IMMUNOASSAY

(75) Inventors: Joseph Beechem, Eugene, OR (US); Kyle Richard Gee, Springfield, OR (US); David Carl Hagen, Eugene, OR (US); Iain D Johnson, Eugene, OR (US); Hee-Chol Kang, Eugene, OR (US); Christina Pastula, Seattle, WA (US)

(73) Assignee: Invitrogen Corporation, Carlsbad, CA (US)

( * ) Notice: Subject to any disclaimer, the term of this patent is extended or adjusted under 35 U.S.C. 154(b) by 155 days.

(21) Appl. No.: 10/943,463

(22) Filed: Sep. 17, 2004

(65) Prior Publication Data
US 2006/0160068 A1    Jul. 20, 2006

Related U.S. Application Data

(60) Provisional application No. 60/505,455, filed on Sep. 23, 2003, provisional application No. 60/504,322, filed on Sep. 17, 2003.

(51) Int. Cl.
*G01N 33/53* (2006.01)
*G01N 33/532* (2006.01)
*G01N 33/533* (2006.01)
*C12Q 1/42* (2006.01)
*C07K 1/13* (2006.01)

(52) U.S. Cl. .................. 435/7.1; 435/21; 435/968; 436/544; 436/546; 436/56; 436/800; 530/403; 530/406; 530/807; 568/17

(58) Field of Classification Search ............... 436/543, 436/546, 56, 800, 544; 435/21, 968, 7.1; 530/403, 406, 807; 568/17
See application file for complete search history.

(56) References Cited

U.S. PATENT DOCUMENTS

| | | |
|---|---|---|
| 3,996,345 A | 12/1976 | Ullman et al. |
| 3,998,943 A | 12/1976 | Ullman |
| 4,160,016 A | 7/1979 | Ullman |
| 4,174,384 A | 11/1979 | Ullman et al. |
| 4,196,265 A | 4/1980 | Koprowski et al. |
| 4,261,968 A | 4/1981 | Ullman et al. |
| 4,318,846 A | 3/1982 | Khana et al. |
| 4,603,209 A | 7/1986 | Tsien et al. |
| 4,714,763 A | 12/1987 | Theodoropulos |
| 4,774,339 A | 9/1988 | Haugland et al. |
| 4,810,636 A | 3/1989 | Corey |
| 4,812,409 A | 3/1989 | Babb et al. |
| 4,849,362 A | 7/1989 | DeMarinis et al. |
| 4,945,171 A | 7/1990 | Haugland et al. |
| 4,981,977 A | 1/1991 | Southwick et al. |
| 5,132,432 A | 7/1992 | Haugland et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Wagonner et al. |
| 5,274,113 A | 12/1993 | Kang et al. |
| 5,360,895 A | 11/1994 | Hainfeld et al. |
| 5,433,896 A | 7/1995 | Kang et al. |
| 5,442,045 A | 8/1995 | Haugland et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,627,027 A | 5/1997 | Waggoner |
| 5,696,157 A | 12/1997 | Wang |
| 5,798,276 A | 8/1998 | Haugland et al. |
| 5,808,044 A | 9/1998 | Brush et al. |

(Continued)

FOREIGN PATENT DOCUMENTS

EP    1 065 250    1/2001

(Continued)

OTHER PUBLICATIONS

Lee et al. (1999): STN international HCAPLUS database, columbus (OH), accession No. 1999: 120261.*

(Continued)

*Primary Examiner*—Long V. Le
*Assistant Examiner*—Shafiqul Haq

(57) ABSTRACT

The present invention provides ligand-detection reagents, ligand analogs and methods for determining the presence of a ligand in a sample. The ligand-detection reagent comprises a ligand-binding antibody and a ligand analog to form an antibody-ligand analog complex wherein the ligand analog is covalently bonded to a reporter molecule. This complex may additionally comprise a labeling protein non-covalently bonded to the antibody to form a ternary complex wherein the labeling protein comprises a monovalent antibody fragment or a non-antibody protein that is covalently bonded to a label moiety. The reporter molecule is either quenched by the ligand-binding antibody or by the label moiety of the labeling protein, depending on the reporter molecule and the ligand-binding antibody, wherein the amount of quenching is directly related to the amount of ligand present in the sample. Alternatively, the ligand analog is fluorogenic wherein the ligand analog is essentially non-fluorescent in solution but when bound by the ligand-binding antibody the detectable signal increases. In this instance a decrease in signal, as opposed to the relieving of quenching, is measured for the presence of a target ligand.

13 Claims, 17 Drawing Sheets

U.S. PATENT DOCUMENTS

| | | | |
|---|---|---|---|
| 5,830,912 | A | 11/1998 | Gee et al. |
| 5,846,737 | A | 12/1998 | Kang |
| 5,877,310 | A | 3/1999 | Reddington et al. |
| 6,002,003 | A | 12/1999 | Shen et al. |
| 6,080,868 | A | 6/2000 | Lee et al. |
| 6,130,101 | A | 10/2000 | Mao et al. |
| 6,162,931 | A | 12/2000 | Gee et al. |
| 6,229,055 | B1 | 5/2001 | Klaubert et al. |
| 6,348,596 | B1 | 2/2002 | Lee et al. |
| 6,399,392 | B1 | 6/2002 | Haugland et al. |
| 6,441,140 | B1 | 8/2002 | Comb et al. |
| 6,541,618 | B1 | 4/2003 | Lee et al. |

FOREIGN PATENT DOCUMENTS

| | | |
|---|---|---|
| WO | WO97/40104 | 10/1997 |
| WO | WO99/51702 | 10/1999 |
| WO | WO 01/21624 | 3/2001 |
| WO | WO 02/26891 | 4/2002 |
| WO | WO 03/030817 | 4/2003 |

OTHER PUBLICATIONS

Zhang et al. (2003): STN international HCAPLUS database, columbus (OH), accession No. 2003: 396733.*

Zhang, J. H., T. D. Chung, et al. (1999). "A Simple Statistical Parameter for Use in Evaluation and Validation of High Throughput Screening Assays." *J Biomol Screen* 4(2): 67-73.

Tyagi, S., D. P. Bratu, et al. (1998). "Multicolor molecular beacons for allele discrimination." *Nat Biotechnol* 16(1): 49-53.

Tyagi, S. and F. R. Kramer (1996). "Molecular beacons: probes that fluoresce upon hybridization."*Nat Biotechnol* 14(3): 303-8.

dos Remedios, C. G. and P. D. Moens (1995). "Fluorescence resonance energy transfer spectroscopy is a reliable "ruler" for measuring structural changes in proteins. Dispelling the problem of the unknown orientation factor." *J Struct Biol* 115(2): 175-85.

Wu, P. and L. Brand (1994). "Resonance energy transfer: methods and applications." *Anal Biochem* 218(1): 1-13.

Selvin, P. R. (1995). "Fluorescence resonance energy transfer." *Methods Enzymol* 246: 300-34.

Matayoshi, E. D., G. T. Wang, et al. (1990). "Novel fluorogenic substrates for assaying retroviral proteases by resonance energy transfer." *Science* 247(4945): 954-8.

Gorevic, P. D., F. C. Prelli, et al. (1985). "Immunoglobulin G (lgG)." *Methods Enzymol* 116: 3-25.

Morrison, L.E. (1992). "Detection of Energy Transfer and Fluorescence Quenching." *Nonisotopic DNA Probes Techniques* 311-52.

Furniss, B. S., A. J. Hannaford, et al. (1989). *Vogel's Textbook of Practical Organic Chemistry* 5th Ed: 809-23.

Heller, A. (1990). "Electrical Wiring of Redox Enzymes." Acc Chem Res 23: 128-34.

Haugland, R. P. (2002). *Handbook of Fluorescent Probes and Research Products* 9th Ed.

* cited by examiner

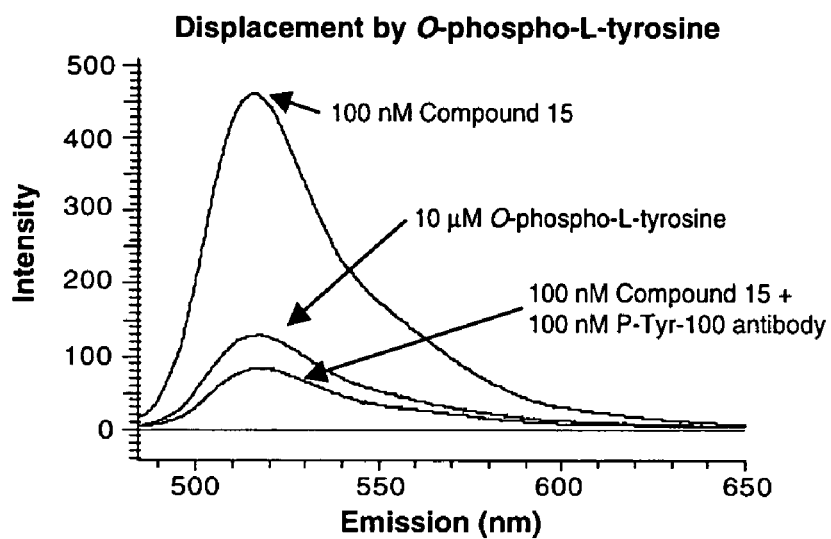
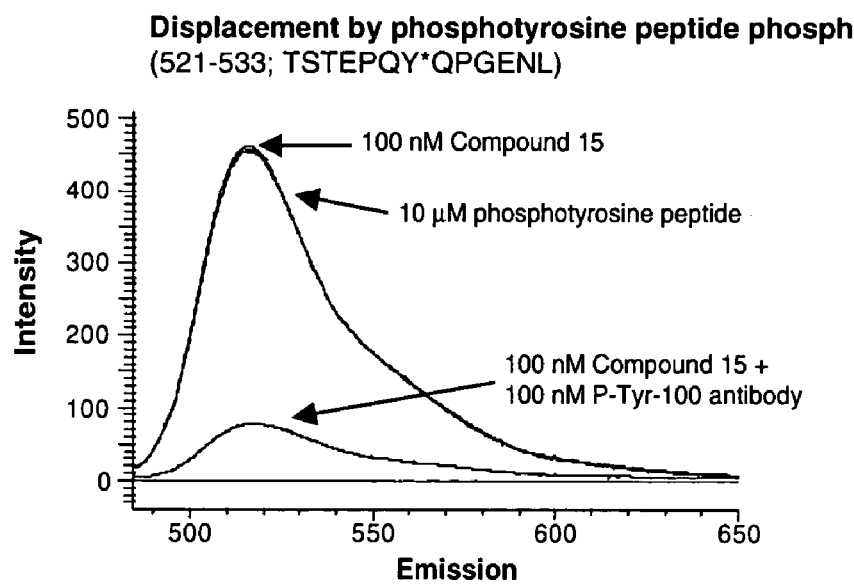
Figure 13

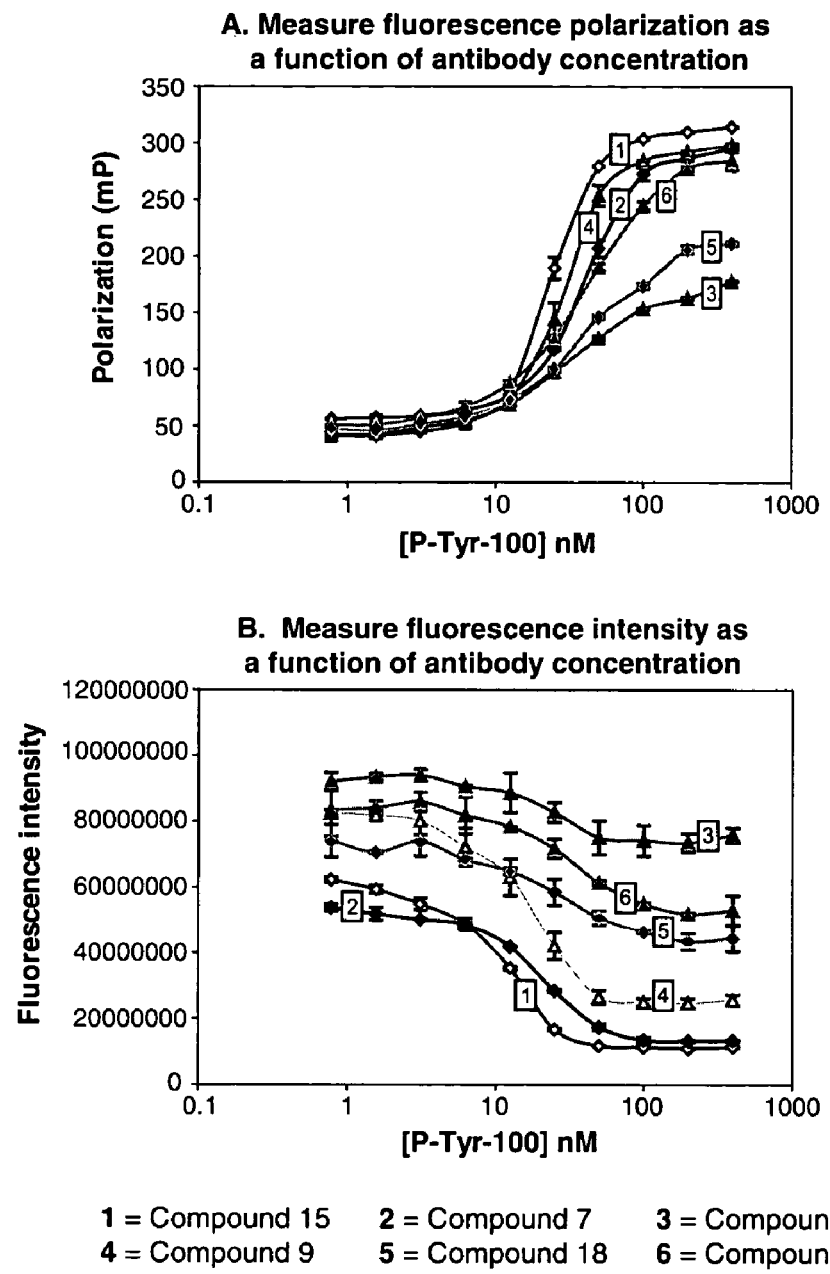
Figure 14 A, B

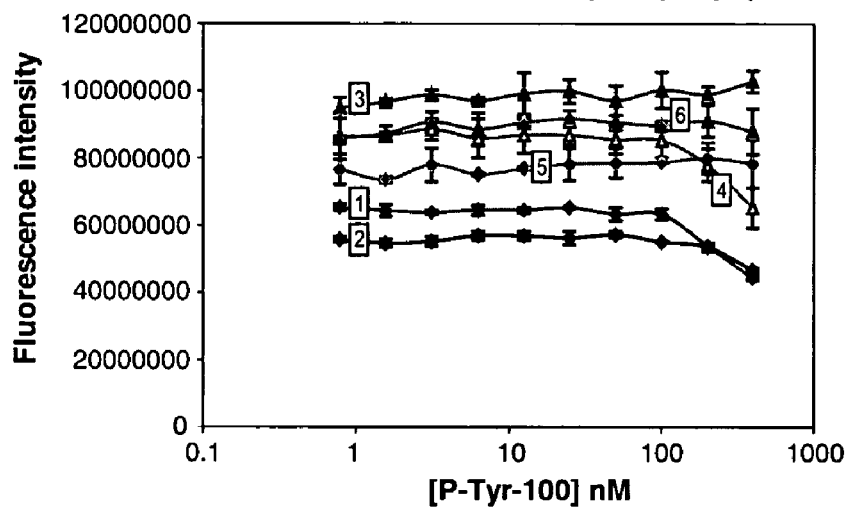
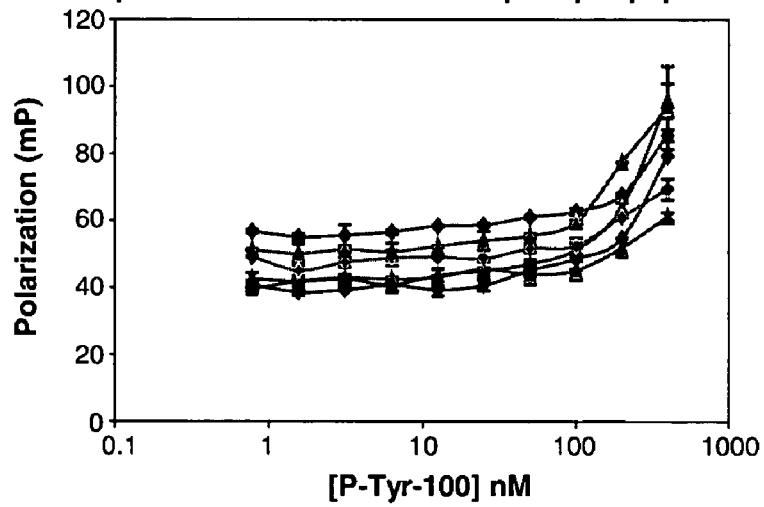
1 = Compound 15   2 = Compound 7    3 = Compound 8
4 = Compound 9    5 = Compound 18   6 = Compound 19
Figure 14 C, D

SEQUENCE LISTING

<160> NUMBER OF SEQ ID NOS: 14

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 1

Glu Asn Asp Tyr Ile Asn Ala Ser Leu
1               5

<210> SEQ ID NO 2
<211> LENGTH: 11
<212> TYPE: PRT
<213> ORGANISM: Mus musculus
<220> FEATURE:
<221> NAME/KEY: MOD_RES
<222> LOCATION: (5)..(5)
<223> OTHER INFORMATION: PHOSPHORYLATION

<400> SEQUENCE: 2

Asp Ala Asp Glu Tyr Leu Ile Pro Gln Gln Gly
1               5                   10

<210> SEQ ID NO 3
<211> LENGTH: 6
<212> TYPE: PRT
<213> ORGANISM: Trichodesmium erythraeum
<220> FEATURE:
<221> NAME/KEY: MOD_RES
<222> LOCATION: (5)..(5)
<223> OTHER INFORMATION: PHOSPHORYLATION

<400> SEQUENCE: 3

Asp Ala Asp Glu Tyr Leu
1               5

<210> SEQ ID NO 4
<211> LENGTH: 5
<212> TYPE: PRT
<213> ORGANISM: Drosophila melanogaster
<220> FEATURE:
<221> NAME/KEY: MOD_RES
<222> LOCATION: (2)..(2)
<223> OTHER INFORMATION: PHOSPHORYLATION

<400> SEQUENCE: 4

Ile Tyr Gly Glu Phe
1               5

<210> SEQ ID NO 5
<211> LENGTH: 5
<212> TYPE: PRT
<213> ORGANISM: Drosophila melanogaster

<400> SEQUENCE: 5

Ile Tyr Gly Glu Phe
1               5

<210> SEQ ID NO 6
<211> LENGTH: 9
<212> TYPE: PRT

```
<213> ORGANISM: Mus musculus
<220> FEATURE:
<221> NAME/KEY: MOD_RES
<222> LOCATION: (5)..(5)
<223> OTHER INFORMATION: PHOSPHORYLATION

<400> SEQUENCE: 6

Thr Glu Pro Glu Tyr Gln Pro Gly Glu
1               5

<210> SEQ ID NO 7
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 7

Asp Tyr Val Pro Met Leu
1               5

<210> SEQ ID NO 8
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Biotinylated
<220> FEATURE:
<221> NAME/KEY: MOD_RES
<222> LOCATION: (4)..(4)
<223> OTHER INFORMATION: PHOSPHORYLATION

<400> SEQUENCE: 8

Glu Pro Gln Tyr Glu Glu Ile Pro Ile Tyr Leu
1               5                   10

<210> SEQ ID NO 9
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Biotinylated

<400> SEQUENCE: 9

Glu Gly Pro Trp Leu Glu Glu Glu Glu Ala Tyr Gly Trp Met Ser
1               5                   10                  15

Phe

<210> SEQ ID NO 10
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 10

Thr Ser Thr Glu Pro Gln Tyr Gln Pro Gly Glu Asn Leu
1               5                   10

<210> SEQ ID NO 11
```

-continued

```
<211> LENGTH: 12
<212> TYPE: PRT
<213> ORGANISM: Pseudomonas syringae

<400> SEQUENCE: 11

Glu Ala Ile Tyr Ala Ala Pro Phe Ala Lys Lys Lys
1               5                   10

<210> SEQ ID NO 12
<211> LENGTH: 9
<212> TYPE: PRT
<213> ORGANISM: Homo sapiens

<400> SEQUENCE: 12

Trp Ala Gly Gly Asp Ala Ser Gly Glu
1               5

<210> SEQ ID NO 13
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 13

Trp Ala Gly Gly Asp Ala Ser Gly Glu
1               5

<210> SEQ ID NO 14
<211> LENGTH: 6
<212> TYPE: PRT
<213> ORGANISM: Homo sapiens

<400> SEQUENCE: 14

Arg Arg Ala Thr Val Ala
1               5
```

COMPETITIVE IMMUNOASSAY

CROSS-REFERENCE TO RELATED APPLICATIONS

This application claims priority of U.S. Ser. No. 60/505,455, filed Sep. 17, 2003 and U.S. Ser. No. 60/504,322, filed Sep. 17, 2003, which disclosures are herein incorporated by reference.

FIELD OF THE INVENTION

The present invention relates to ligand-binding reagents and use of the reagents in a competitive immunoassay for the detection and measurement of one or more target ligands in a biological sample. The invention has applications in the fields of molecular biology, cell biology, immunohistochemistry, diagnostics, and therapeutics.

BACKGROUND OF THE INVENTION

Antibodies are powerful tools for the detection, monitoring and quantitation of an unknown antigen in a sample wherein immunoassays have acquired widespread use. Enzyme immunosorbent immunoassays, typically referred to as an ELISA, are the most common form of immunoassays wherein a primary or secondary antibody is labeled with an enzyme or enzyme binding molecule wherein a luminescent signal is obtained after binding of the antigen. This method is heterogeneous and requires multiple steps and reagents. In the past decade fluorescent labeled primary and secondary antibodies have been employed for the detection of antigen allowing for more sensitivity and detection in samples such as tissue sections and intracellular targets. A particular type of immunoassay includes competitive immunoassays wherein the presence and amount of a particular antigen in an unknown sample is determined by its ability to compete with labeled reference antigen for binding to an antibody immobilized on a solid surface, e.g., microwell plate. To quantitate the bound antigen a standard curve of known concentrations of the antigen must be assayed with the unknown samples. Competitive immunoassays are powerful tools for their ability to detect small quantities of antigen in a complex sample, however, due to inherent limitations they have not acquired widespread use. Herein we report a novel homogenous competitive assay that allows for rapid detection of a target ligand in a sample.

The present invention takes advantage of fluorescent-labeled ligand analogs and fluorophore or quencher labeled labeling proteins wherein a target ligand displaces the ligand analog resulting in a change in the detectable signal. The change in detectable signal can be a result of FRET, inherent quenching by the ligand-binding antibody or the use of a fluorogenic ligand analog. Competitive immunoassays using chromophores as quenchers and acceptors for FRET have been disclosed wherein the ligand analog is conjugated to a chromophore and the primary or secondary antibody is conjugated to another chromophore (U.S. Pat. Nos. 3,998,943; 4,160,016; 4,174,384; 4,261,968; 3,996,345). This method has limitations in that either the primary antibody or secondary antibody are required to be conjugated to a fluorophore. When the primary antibody is conjugated to a chromophore the labeling method often result in labeling that interferes with binding or a lower detectable signal than expected. In addition, the labeling of primary antibody is an additional step for the end user. Alternatively, labeling of secondary antibody results in a more universal immunoassay, however the secondary antibody needs to be added sequentially to the sample or risk the primary+secondary antibody complex precipitating out of solution.

We have developed a homogenous competitive immunoassay that does not require labeling of primary antibody or the use of a labeled secondary antibody. For this invention a labeling protein is employed that is a monovalent antibody fragment or non-antibody protein that can be pre-complexed with the primary antibody. In addition, the present invention takes advantage of the inherent quenching of the ligand analog by the ligand antibody that is accomplished by appropriate matching of the ligand analog and the ligand-binding antibody.

SUMMARY OF THE INVENTION

The present invention provides ligand-detection reagents, ligand analogs and methods for determining the presence of a ligand in a sample. The ligand-detection reagent comprises a ligand-binding antibody and a ligand analog to form an antibody-ligand analog complex wherein the ligand analog is covalently bonded to a reporter molecule. This complex may additionally comprise a labeling protein non-covalently bonded to the antibody to form a ternary complex wherein the labeling protein comprises a monovalent antibody fragment or a non-antibody protein that is covalently bonded to a label moiety. The reporter molecule is either quenched by the ligand-binding antibody or by the label moiety of the labeling protein, depending on the reporter molecule and the ligand-binding antibody, wherein the amount of quenching is directly related to the amount of ligand present in the sample. Alternatively, the ligand analog is fluorogenic wherein the ligand analog is essentially non-fluorescent in solution but when bound by the ligand-binding antibody the detectable signal increases. In this instance a decrease in signal, as opposed to the relieving of quenching, is measured for the presence of a target ligand.

The ligand analog is covalently attached to a reporter molecule selected from the group consisting of a borapolyazaindacene, a coumarin, a xanthene, a cyanine, a fluorescent protein, and a phosphorescent dye. Through careful selection of the reporter molecule, ligand analog and ligand-binding antibody we have demonstrated that the reporter molecule can be substantially quenched or masked by the ligand-binding antibody. This substantial quenching is preferably more than 60%, even more preferable is more than 70% and the most preferred is wherein 80% or more of the detectable signal from the reporter molecule is quenched when complexed with a ligand-binding antibody. This unexpected advantage provides for a ligand-detection reagent wherein the reporter molecule is quenched without the use of a traditional quencher compound.

Alternatively, the ligand-detection reagent also comprises a labeling protein that is a monovalent antibody fragment or a non-antibody protein that has affinity for a region of the ligand-binding antibody. This labeling protein is covalently attached to a label wherein the label is capable of absorbing energy from the reporter molecule to form an energy transfer pair when complexed with the ligand-binding antibody. The emitted energy from the reporter molecule is either absorbed by the label and re-emitted at a longer wavelength than energy emitted by the reporter molecule or is absorbed with little or no energy being re-emitted at a longer wavelength. In this way the label is either considered a quencher or a fluorophore moiety, both of which are capable of absorbing energy from the reporter molecule.

Therefore a method is provided for determining the presence of a ligand in a sample employing the ligand-detection reagent. In carrying out the present methods the ligand analog-reporter molecule is complexed with the ligand-binding antibody and optionally the labeling protein is complexed with the ligand-binding antibody as well wherein the reporter molecule is quenched or masked. The reagent is incubated with the sample for a sufficient amount of time to allow for the target ligand present in the sample to displace the ligand-analog. In this way the unmasking of the reporter molecule provides either the presence of a detectable signal or a shift in color compared to when the ligand-binding antibody bound the ligand analog. Alternatively, a decrease in detectable signal is measured to indicate the presence of a target ligand when a fluorogenic ligand analog is employed.

The present invention provides novel ligand-detection reagents, ligand-analogs and a competitive immunoassay for the determination of the presence or absence of a target ligand in a sample.

BRIEF DESCRIPTION OF THE DRAWINGS

FIG. 13: Shows that phosphotyrosine causes minimal displacement of the phosphotyrosine ligand analog from antibody binding sites.

FIG. 14: Shows a method for selecting ligands for use in displacement assays. FIG. 14A shows the measure of fluorescence polarization as a function of antibody concentration, FIG. 14B shows the measure of fluorescence intensity as a function of antibody concentration, FIG. 14C shows a measure of fluorescence enhancement in the presence of target ligand (phosphopeptide) and FIG. 14D shows the confirmation of fluorescence enhancement by depolarization of the ligand analog.

DETAILED DESCRIPTION OF THE INVENTION

I. Definitions

Figure 1A:
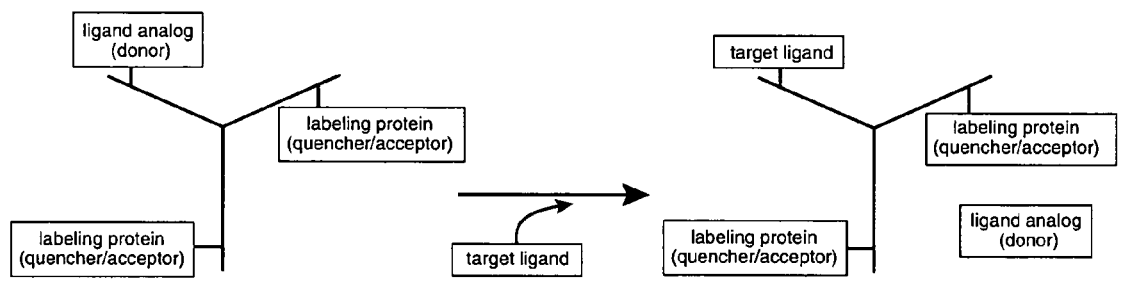
FIG. 1: Shows a schematic representation of the ligand-detection reagent with a labeling protein (FIG. 1A) and without a labeling protein (FIG. 1B).

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a protein-labeling complex" includes a plurality of complexes and reference to "a target-binding protein" includes a plurality of proteins and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

Although typically not shown for the sake of clarity, any overall positive or negative charges possessed by any of the compounds of the invention are balanced by a necessary counterion or counterions. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylborate, nitrate, hexafluorophosphate, and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized, and the sulfur atoms are optionally trivalent with alkyl or heteroalkyl substituents. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 4 rings), which are fused together or linked covalently. Specific examples of aryl substituents include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl Preferred aryl substituents are phenyl, substituted phenyl, naphthyl or substituted naphthyl.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, qunolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

Where a ring substituent is a heteroaryl substituent, it is defined as a 5- or 6-membered heteroaromatic ring that is optionally fused to an additional six-membered aromatic ring(s), or is fused to one 5- or 6-membered heteroaromatic ring. The heteroaromatic rings contain at least 1 and as many as 3 heteroatoms that are selected from the group consisting of O, N or S in any combination. The heteroaryl substituent is bound by a single bond, and is optionally substituted as defined below.

Specific examples of heteroaryl moieties include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5-(1,3-oxazolyl); 2-benzoxazolyl; 2-, 4-, or 5-(1, 3-thiazoly); 2-benzothiazolyl; 3-, 4-, or 5-isoxazolyl; N-, 2-, or 4-imidazolyl; N-, or 2-benzimidazolyl; 1- or 2-naphthofuranyl; 1- or 2-naphthothienyl; N-, 2- or 3-benzindolyl; 2-, 3-, or 4-benzoquinolyl; 1-, 2-, 3-, or 4-acridinyl. Preferred heteroaryl substituents include substituted or unsubstituted 4-pyridyl, 2-thienyl, 2-pyrrolyl, 2-indolyl, 2-oxazolyl, 2-benzothiazolyl or 2-benzoxazoly.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$ R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present. In the schemes that follow, the symbol X represents "R" as described above.

The aryl and heteroaryl substituents described herein are unsubstituted or optionally and independently substituted by H, halogen, cyano, sulfonic acid, carboxylic acid, nitro, alkyl, perfluoroalkyl, alkoxy, alkylthio, amino, monoalkylamino, dialkylamino or alkylamido.

Two of the substituents on adjacent atoms of the aryl or heteroaryl ring may optionally be replaced with a substituent of the formula -T—C(O)—(CRR')$_q$—U—, wherein T and U are independently —NR—, —O—, —CRR'— or a single bond, and q is an integer of from 0 to 3.

Alternatively, two of the substituents on adjacent atoms of the aryl or heteroaryl ring may optionally be replaced with a substituent of the formula -A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R'' (or NRR'R'') where R, R' and R'' are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R'' is other than hydrogen. In a primary amino group, both R' and R'' are hydrogen, whereas in a secondary amino group, either, but not both, R' or R'' is hydrogen. In addition, the terms "amine" and "amino" can include protonated and quaternized versions of nitrogen, comprising the group —NRR'R'' and its biologically compatible anionic counterions.

The term "affinity" as used herein refers to the strength of the binding interaction of two molecules, such as an antibody and a ligand or antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "High affinity" refers to a ligand that binds to an antibody having an affinity constant (K$_a$) greater than $10^4$ M$^{-1}$, typically $10^5$-$10^{11}$ M$^{-1}$; as determined by inhibition ELISA or an equivalent affinity determined by comparable techniques such as, for example, Scatchard plots or using K$_d$/dissociation constant, which is the reciprocal of the K$_a$, etc.

The term "antibody" as used herein refers to a protein of the immunoglobulin (Ig) superfamily that binds noncovalently to certain substances (e.g. antigens and immunogens) to form an antibody-antigen complex. Antibodies can be endogenous, or polyclonal wherein an animal is immunized to elicit a polyclonal antibody response or by recombinant methods resulting in monoclonal antibodies produced from hybridoma cells or other cell lines. It is understood that the term "antibody" as used herein includes within its scope any of the various classes or sub-classes of immunoglobulin derived from any of the animals conventionally used.

The term "antibody fragments" as used herein refers to fragments of antibodies that retain the principal selective binding characteristics of the whole antibody. Particular fragments are well-known in the art, for example, Fab, Fab', and F(ab')$_2$, which are obtained by digestion with various proteases, pepsin or papain, and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

The term "antigen" as used herein refers to a molecule that induces, or is capable of inducing, the formation of an antibody or to which an antibody binds selectively, including but not limited to a biological material. Antigen also refers to "immunogen". The ligand-binding antibodies selectively bind an antigen, as such the term can be used herein interchangeably with the terms "ligand" and "target".

The term "anti-region antibody" as used herein refers to an antibody that was either produced by immunizing an animal with a select region that is a fragment of a foreign antibody wherein only the fragment is used as the immunogen or isolated against the specific region of the antibody. Anti-region antibodies include monoclonal and polyclonal antibodies. The term "anti-region fragment" as used herein refers to a monovalent fragment that was generated from an anti-region antibody of the present invention by enzymatic cleavage.

The term "buffer" as used herein refers to a system that acts to minimize the change in acidity or basicity of the solution against addition or depletion of chemical substances.

The term "complex" as used herein refers to the association of two or more molecules, usually by non-covalent bonding, e.g., the association between an antibody and ligand (analog) or the labeling protein and the ligand-binding antibody.

The term "detectable response" as used herein refers to an occurrence of, or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters. Alternatively the detectable response is an occurrence of a signal wherein the fluorophore is inherently fluorescent and does not produce a change in signal upon binding to a biological compound. Other detectable responses include, for example, chemiluminescence, phosphorescence, radiation from radioisotopes, magnetic attraction, and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "energy transfer" as used herein refers to the process by which the excited state energy of an excited group, e.g. fluorescent reporter dye, is conveyed through space or through bonds to another group, e.g. a quencher moiety or fluorescer, which may attenuate (quench) or otherwise dissipate or transfer the energy to another reporter molecule or emit the energy at a longer wavelength. Energy transfer typically occurs through fluorescence resonance energy transfer (FRET).

The term "energy transfer pair" as used herein refers to any two moieties that participate in energy transfer. Typically, one of the moieties acts as a fluorescent reporter, i.e. donor, and the other acts as an acceptor, which may be a quenching compound or a compound that absorbs and re-emits energy in the form of a fluorescent signal ("Fluorescence resonance energy transfer." Selvin P. (1995) Methods Enzymol 246:300-334; dos Remedios C. G. (1995) J. Struct. Biol. 115:175-185; "Resonance energy transfer: methods and applications." Wu P. and Brand L. (1994) Anal Biochem 218:1-13). Fluorescence resonance energy transfer (FRET) is a distance-dependent interaction between two moieties in which excitation energy, i.e. light, is transferred from a donor to an acceptor without emission of a photon. The acceptor may be fluorescent and emit the transferred energy at a longer wavelength, or it may be non-fluorescent and serve to diminish the detectable fluorescence of the reporter molecule (quenching). FRET may be either an intermolecular or intramolecular event, and is dependent on the inverse sixth power of the separation of the donor and acceptor, making it useful over distances comparable with the dimensions of biological macromolecules. When an energy transfer pair is part of the present ligand-detection reagent the energy transfer is an intramolecular event. Thus, the spectral properties of the energy transfer pair as a whole change in some measurable way if the distance between the moieties is altered by some critical amount. Self-quenching probes incorporating fluorescent donor-non-fluorescent acceptor combinations have been developed primarily for detection of proteolysis (Matayoshi, (1990) Science 247: 954-958) and nucleic acid hybridization ("Detection of Energy Transfer and Fluorescence Quenching" Morrison, L., in Nonisotopic DNA Probe Techniques, L. Kricka, Ed., Academic Press, San Diego, (1992) pp. 311-352; Tyagi S. (1998) Nat. Biotechnol. 16:49-53; Tyagi S. (1996) Nat. Biotechnol 14:303-308). In most applications, the donor and acceptor dyes are different, in which case FRET can be detected by the appearance of sensitized fluorescence of the acceptor or by quenching of donor fluorescence.

The term "kit" as used herein refers to a packaged set of related components, typically one or more compounds or compositions.

The term "label" as used herein refers to a chemical moiety or protein that retains it's native properties (e.g. spectral properties, conformation and activity) when attached to a labeling protein and used in the present methods. The label can be directly detectable (fluorophore) or act as a quencher for the reporter molecule of the ligand analog. Such labels include, but are not limited to, pigments, dyes or other chromogens that can be visually observed or measured with a spectrophotometer; quenching moiety that functions to absorb and not re-emit the energy from the dye moiety of the ligand analog that is within close proximity; and fluorescent labels (fluorophores), where the output signal is generated by the excitation of a suitable molecular adduct and that can be visualized by excitation with light that is absorbed by the dye or can be measured with standard fluorometers or imaging systems, for example. Numerous fluorophore and quenching moiety labels are know by those of skill in the art and include, but are not limited to, cyanine, xanthene, borapolyazaindacene and other labels that are described in RICHARD P. HAUGLAND, MOLECULAR PROBES HANDBOOK OF FLUORESCENT PROBES AND RESEARCH PRODUCTS ($9^{th}$ edition, CD-ROM, September 2002), supra.

The term "labeling protein" as used herein refers to a monovalent antibody fragment or a non-antibody monomeric protein provided that the labeling protein has affinity for a selected region of the ligand-binding antibody and is covalently attached to a label.

The term "ligand" as used herein refers to a moiety that contains an antibody binding epitope. The ligand may contain amino acids to form peptides or proteins or the ligand may be essentially free of amino acids.

The term "ligand analog" as used herein refers to ligand that has been modified to contain a reporter molecule and optionally to alter the affinity of the ligand analog for the ligand-binding antibody compared to an appropriate ligand. Typically, reporter molecules are conjugated using an appropriate reactive group to a antibody binding epitope to form a ligand-analog. The affinity modification includes, but is not limited to, the addition of a dye moiety, addition of alkyl groups to the binding epitope, change of amino acid sequence of the epitope or spacing of the dye moiety from the epitope. Thus, the ligand analog has the same spatial and polar organization as the ligand to define one or more determinant or epitopic sites capable of competing with the ligand for the binding sites of a receptor, and differs from the ligand in the absence or presence of an atom or functional group at the site of binding to another molecule or in having a linking group which has been introduced in place of one or more atoms originally present in the ligand.

The term "ligand-binding antibody" as used herein refers to an antibody that has affinity for a discrete epitope, antigen or ligand that can be used with the methods of the present invention. Typically the discrete epitope is the target but the epitope can be a marker for the target such as CD3 on T cells. Ligand-binding antibody can be used interchangeably with the term "primary antibody" when describing methods that use an antibody that binds directly to the antigen as opposed to a "secondary antibody" that binds to a region of the primary antibody.

The term "ligand-detection reagent" as used herein refers to one of two immuno-complexes that are used to determine the presence of a target ligand in a sample. The first complex comprises a ligand-binding antibody and a non-covalently bound ligand analog wherein the dye moiety of the ligand analog is quenched by the ligand-binding antibody. The second complex comprises a ligand-binding antibody, a ligand analog and a labeling protein wherein the covalently bonded label is a fluorophore or a quenching moiety. In both cases, the ligand analog is displaced by the target ligand resulting in a change in signal intensity or a shift in color change of the detectable signal whereby the presence of a target ligand is determined.

The term "matrix" as used herein refers to a solid or semi-solid surface that a biological molecule can be attached to, such as a sample of the present invention or a capture reagent. Examples include, but are not limited to, agarose, polyacrylamide gel, polymers, microspheres, glass surface, plastic surface, membrane, margnetic surface, and an array.

The term "monovalent antibody fragment" as used herein refers to an antibody fragment that has only one antigen-binding site. Examples of monovalent antibody fragments include, but are not limited to, Fab fragments (no hinge region), Fab' fragments (monovalent fragments that contain a heavy chain hinge region), and single-chain fragment variable (ScFv) proteins.

The term "non-antibody monomeric protein" as used herein refers to a protein that binds selectively and non-covalently to a member of the Ig superfamily of proteins, including but not limited to proteins A, G, and L, hybrids thereof (A/G), recombinant versions and cloned versions thereof, fusions of these proteins with detectable protein labels, and lectins but the protein itself is not an antibody or an antibody fragment.

The terms "protein" and "polypeptide" are used herein in a generic sense to include polymers of amino acid residues of any length. The term "peptide" is used herein to refer to polypeptides having fewer than 100 amino acid residues, typically fewer than 10 amino acid residues. The terms apply to amino acid polymers in which one or more amino acid residues are an artificial chemical analog of a corresponding naturally occurring amino acid, as well as to naturally occurring amino acid polymers.

The term "purified" as used herein refers to a preparation of a ligand-binding antibody that is essentially free from contaminating proteins that normally would be present in association with the antibody, e.g., in a cellular mixture or milieu in which the protein or complex is found endogenously such as serum proteins or hybridoma supernatant.

The term "quenching moiety" or "quencher" as used herein refers to a compound that is capable of absorbing energy from an energy donor that is not re-emitted (non-fluorescent) or re-emitted at a detectably different wavelength from the energy emitted by the donor molecule. In this respect, quenchers may be essentially non-fluorescent or fluorescent. Numerous quenching moieties are well known in the art including xanthene and cyanine compounds and other compounds disclosed in RICHARD P. HAUGLAND, MOLECULAR PROBES HANDBOOK OF FLUORESCENT PROBES AND RESEARCH PRODUCTS ($9^{th}$ edition, CD-ROM, September 2002), supra.

The term "reporter molecule" as used herein refers to any luminescent molecule that is capable of functioning as a member of an energy transfer pair wherein the reporter molecule retains it's native properties (e.g. spectral properties, conformation and activity) when attached to a ligand analog and used in the present methods. Typically, luminescent molecules, as used herein include dyes, fluorescent proteins, phosphorescent dyes, chromophores and chemiluminescent compounds that are capable of producing a detectable signal upon appropriate activation. The term "dye" refers to a compound that emits light to produce an observable detectable signal. "Dye" includes fluorescent and nonfluorescent compounds that include without limitations pigments, fluorophores, chemiluminescent compounds, luminescent compounds and chromophores. The term "chromophore" as used herein refers to a label that emits and/or reflects light in the visible spectra that can be observed without the aid of instrumentation. The term "fluorophore" as used herein refers to a composition that is inherently fluorescent or demonstrates a change in fluorescence upon binding to a biological compound, i.e. can be fluorogenic or the intensity can be diminished by quenching. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

The term "sample" as used herein refers to any material that may contain a ligand or taget, as defined below. Typically, the sample comprises a population of cells, cellular extract, subcellular components, tissue culture, a bodily fluid, tissue, and reaction mixtures. The sample may be in an aqueous solution, a viable cell culture or immobilized on a solid or semi-solid surface such as a gel, a membrane, a glass surface, a microparticle or on a microarray.

The term "target" as used herein refers to any entity that a ligand-binding antibody has affinity for such as an epitope or antigen. This target includes not only the discrete epitope that the ligand-binding antibody has affinity for but also includes any subsequently bound molecules or structures. In this way an epitope serves as a marker for the intended target.

For example, a cell is a target wherein the ligand-binding antibody binds a cell surface protein such as CD3 on a T cell wherein the target marker is CD3 and the target is the T cell.

The term "ternary complex" as used herein refers to a composition that simultaneously comprises a ligand-binding antibody, a ligand analog of the present invention and labeling protein wherein the ligand analog is non-covalently bound in the binding groove of the ligand-binding antibody and the labeling protein is noncovalently bonded to a region, e.g. Fc, of the ligand-binding antibody.

II. Compositions and Methods of Use

The present invention provides ligand-detection reagents, ligand analogs and methods of employing the reagents for the detection of a target ligand. The ligand-detection reagents comprise a ligand-binding antibody, a ligand analog that is covalently attached to a reporter molecule and optionally a labeling protein that is covalently attached to a labeling protein. The ligand-detection reagent is a complex wherein the ligand analog is noncovalently bound by the binding groove of the antibody and the labeling protein is noncovalently bound to a region of the antibody. The methods employ the ligand-detection reagents wherein in one aspect of the invention energy transfer is utilized in a competitive immunoassay format to determine the presence of a ligand in a sample. In another aspect, a fluorogenic ligand analog is employed wherein energy transfer is typically not utilized.

A. Ligand Analog

The ligand analog comprises at least one epitope site for a desired ligand-binding antibody, a reporter molecule and a linker. Thus, the ligand analog may be monovalent or polyvalent. Typically the ligand analog is monovalent or divalent. In one aspect of the invention the monovalent ligand analog is quenched when bound by the ligand-binding antibody. Thus, monovalent ligand analogs are preferred for applications wherein it is desired that the ligand analog be quenched when bound by the ligand-binding antibody. In another aspect, the divalent ligand analog is fluorogenic wherein the ligand analog is essentially non-fluorescent when unbound from the ligand-binding antibody but when bound by the antibody in such a way that the each binding groove is bound to the bivalent ligand analog and the reporter molecule is held in between the two Fab fragments of the antibody the fluorogenic ligand analog becomes fluorescent, See Example 11 and Compounds 4 and 5. Thus, in this aspect a divalent ligand analog is preferred for applications wherein a fluorogenic ligand analog is employed.

The ligand analog typically has an altered affinity for the ligand-binding antibody compared to the target ligand. The altered affinity may be greater or less than the target ligand, typically the affinity is less or equal to the affinity of the target ligand. The affinity of the ligand analog is determined empirically along with the selection of the ligand-binding antibody, and optionally the labeling protein to optimize the displacement of the ligand analog by the target ligand in each assay system. The altered affinity of the ligand analog can be accomplished by a number of modifications to the target ligand to make a ligand analog or alternatively a synthetic chemical strategy can be employed to design and synthesize a ligand analog with the appropriate affinity, fluorescence response, and ability to be quenched. Modification to a ligand to form a ligand analog can include a change of a single, or multiple, amino acids, either in the epitope or the surrounding sequence, a change in the post-translational modification of a protein or peptide such as the addition or removal of a sugar group or phosphate, the addition of a linker or simply by the addition of a reporter molecule. Alternatively, the epitope can be synthesized with an appropriate linker and reporter molecule, such as was done for the phosphotyramide, phosphotyrosinamide, phosphoethanolamine and phosphoserine ligand analogs, See Examples 1-8.

Synthesis of the epitope, linker and reporter molecule provide for the most flexibility for designing a ligand analog with the appropriate affinity for the ligand-binding antibody and spectral properties of the reporter molecule. However, this method is typically not preferred wherein a ligand-binding antibody was raised against a ligand that requires a conformational epitope. In this instance, the sequence, spacing, and folding or conformation of the antigen is necessary for adequate binding by the ligand-binding antibody. Thus, for these ligand analogs, the reporter molecule is typically conjugated to the target ligand to form the analog resulting in linker that is typically less than 10 atoms in length.

The ligand analog for the most part will be haptenic, rather than antigenic, and generally be less than about 10,000 molecular weight, more usually less than about 6,000 molecular weight, and frequently in the range of about 125 to 1,000 molecular weight, excluding the linking group employed for linking to the reporter molecule.

Regardless of the method employed to derive a ligand analog, the reporter molecule is typically conjugated to the ligand analog. Thus, the reporter molecule and the ligand analog each need to contain an appropriate reactive or functional group that result in a covalent bond. The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive group of the reporter molecule and the reactive group of the ligand analog results in one or more atoms of the reactive group to be incorporated into a new linkage attaching the reporter molecule to the ligand analog. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the reporter molecule to the ligand analog typically depends on the reactive or functional group on the ligand analog and the type or length of covalent linkage desired. The types of functional groups typically present on biomolecules include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

A linker may be synthesized on the ligand analog or on the reporter molecule wherein after conjugation the linker is incorporated into the ligand analog. The linker typically incorporates 1-30 nonhydrogen atoms selected from the group consisting of C, N, O, S and P. The linker is optionally a substituted alkyl, amine or a substituted cycloalkyl. Alternately, the reporter molecule may be directly attached (where linker is a single bond) to the ligand analog or the alkyl may contain a benzene ring. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 20 nonhydrogen atoms and are composed of any combination of ether, thioether, thiourea, amine, ester, carboxamide, sulfonamide, hydrazide bonds and aromatic or heteroaromatic bonds. Most preferred are linkers that contain less than 10 non-hydrogen atoms. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoky, cycloalkyl and amine moieties.

Any combination of linkers may be used to attach the reporter molecule to the ligand analog. For monovalent ligand analogs the analog typically contains one linker and for divalent ligand analogs the analogs typically incorporate two linkers, which may be the same or different. The linker may also be substituted to alter the physical properties of the ligand analog, such as binding affinity for the ligand-binding antibody and spectral properties of the fluorophore.

We have unexpectedly discovered that the site of attachment of the linker on the reporter molecule alters the ability of the reporter molecule to be quenched when bound to the ligand-binding antibody and the binding affinity of the analog for the ligand-binding antibody. This is particularly true when the reporter molecule is a xanthene dye. By way of example Compound 8 and 9 are isomers but demonstrate different binding affinity for the same antibody and quenching by the same antibody, See, Example 22 and FIG. 14. In this instance, the 6-isomer (linker is attached to the 6 position of the pendent phenyl ring; Compound 9) demonstrates increased binding affinity and increased quenching compared to the 5-isomer of the same ligand analog, Compound 8. Therefore, the position of attachment of the linker on the reporter molecule is important for defining binding affinity of the ligand analog for the ligand-binding antibody and for the ability of the reporter molecule to be masked or quenched when bound by the ligand-binding antibody. This quenching property is particularly relevant when a monovalent ligand analog is employed and the antibody quenches the reporter molecule.

The length of the linker is another important aspect for optimizing the amount of quenching conferred on the reporter molecule. We have found that a shorter linker results in an increased quenching of the reporter molecule by the ligand-binding antibody. Without wishing to be bound by a theory, it appears that quenching is increased when the reporter molecule is "pulled" into the binding groove of the antibody, which is facilitated by a short linker; a short linker preferably containing 10 or less non-hydrogen atoms. In addition, the linker can be substituted by substitutents that alter the physical properties of the ligand analog, such as binding affinity and spectral properties of the reporter molecule. We have unexpectedly found that substituting the linker to form a phosphotyrosinamide instead of a phosphotyramide ligand analog alters the binding affinity and the ability of the reporter molecule to be quenched when bound by the ligand-binding antibody. See, Compounds 34-38 and 41-42 and Example 23.

Therefore, the linker of the ligand analog is important for attaching the reporter molecule to the ligand analog, for altering the binding affinity of the analog and for altering the spectral properties of the reporter molecule. The lengths of the linker, site of attachment on the reporter molecule and linker substituents all are parameters that can be altered to maximize the binding affinity of the analog for the antibody and the ability of the reporter molecule to be quenched when bound by the ligand-binding antibody.

The reporter molecules of the present invention include any detectable label known by one skilled in the art that can be covalently attached to the ligand analog of the present invention. When part of the ligand analog the reporter molecule is typically capable of transferring energy to another moiety to be absorbed and optionally re-emitted at a longer wavelength. Alternatively the reporter molecule is fluorogenic such that when the ligand analog is bound to the ligand-binding antibody the reporter molecule is fluorescent but when unbound is essentially non-fluorescent. Reporter molecules include, without limitation, a chromophore, a fluorophore, a fluorescent protein, and a phosphorescent dye. Typically, substituents on the fluorophore or ligand analog alter the spectral properties to form a fluorogenic ligand analog. Preferred reporter molecules include fluorophores and fluorescent proteins.

A fluorophore of the present invention is any chemical moiety that exhibits an absorption maximum beyond 280 nm, and when covalently attached to a ligand analog retains its spectral properties. Fluorophores of the present invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459, 276; 5,501,980 and 5,830,912), a benzofuran (including an corresponding compounds disclosed in U.S. Pat. Nos. 4,603, 209 and 4,849,362) and benzphenalenone (including any corresponding compounds disclosed in U.S. Pat. No. 4,812, 409) and derivatives thereof. As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Preferred fluorophores of the invention include xanthene (rhodol, rhodamine, fluorescein and derivatives thereof) coumarin, cyanine, pyrene, oxazine and borapolyazaindacene. Most preferred are fluorinated xanthenes, fluorinated coumarins and cyanines. It is preferred that the fluorophore not be substituted by a polar group such as $SO_3^-$ due to poor binding affinity conferred to the ligand analog for the ligand-binding antibody. The choice of the fluorophore attached to the ligand analog will determine the absorption and fluorescence emission properties of the ligand analog, the ligand-detection reagent and ultimately the assay solution in the presence of a ligand. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also preferred chromophores of the present invention.

In one aspect of the invention the ligand analogs are phospho-tyrosine, -threonine or -serine ligand analogs that are employed for the detection of phosphorylated biomolecules including proteins and peptides or for the detection of phosphorylated kinase or phosphatase substrates. Preferred phospho-ligand analogs typically comprise a phosphotyramide moiety a phosphoenthanolamide moiety or a phosphoserine moiety and include phosphotyramide, phosphotyrosinamide, phosphoserine and phosphoethanolamide ligand analogs.

Typically a ligand analog comprising a phosphophenol moiety has the following formula

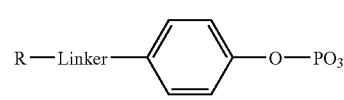

Formula I wherein R is a reporter molecule and linker is a single covalent bond or comprises 1-20 non-hydrogen atoms to covalently attach the reporter molecule to the phosphophenol moiety. Preferred reporter molecules include borapolyazaindacene, coumarin, xanthene, cyanine, fluorescent protein and phosphorescent dye. Most preferred reporter molecules are xanthene, borapolyazaindacene and coumarin, typically these reporter molecules are not substituted by polar groups. The linker typically contains alkyl and amine groups.

In one embodiment, ligand analogs comprising a phosphotyramide moiety are selected from the group consisting of:

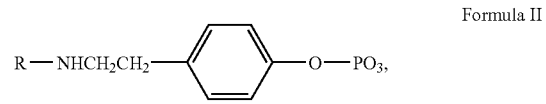

Formula II

Formula III

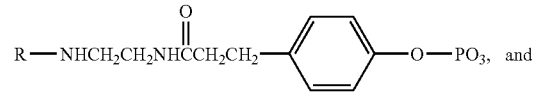

Formula IV

Exemplified Compounds according to Formula II include Compounds 2, 7-21 and 39, exemplified Compounds according to Formula III include Compounds 22-33 and 40, and exemplified compounds according to Formula IV include compounds 34-38 and 41-42.

Formula IV, as used herein is typically referred to as a phosphotyrosinamide ligand analog.

Alternatively, the phosphophenol moiety forms part of a fluorogenic ligand analog according to the following formula:

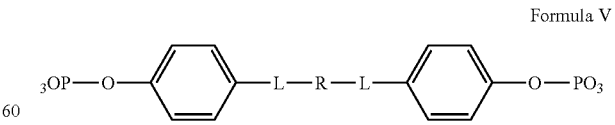

Formula V wherein R is a reporter molecule and L is a linker that is a single covalent bond or comprises 1-20 non-hydrogen atoms to covalently attached the reporter molecule to phosphophenol moiety. Again, preferred reporter molecules are selected from the group consisting of borapolyazaindacene, coumarin, xanthene, cyanine, fluorescent protein and phosphorescent dye. Most preferred is a borapolyazaindacene reporter molecule, See Compounds 4 and 5. The linker typically comprises alkyl and amino groups.

Thus, in a preferred embodiment a fluorogenic ligand analog comprising a phosphotyramide moiety is according to formula:

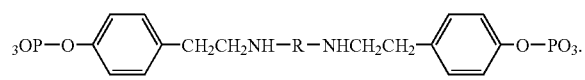

Formula VI $_3$OP—O—⟨⟩—CH$_2$CH$_2$NH—R—NHCH$_2$CH$_2$—⟨⟩—O—PO$_3$.

The fluorogenic ligand analogs are not limited to phosphotyramide moieties, it is appreciated that any epitope that has affinity for a ligand-binding antibody can replace the phosphotyramide moiety of formula VI to form a fluorogenic ligand analog. Preferred epitopes are single amino acids or fragments thereof.

In another aspect of the invention, the ligand analog has affinity for a phosphothreonine or phosphoserine ligand-binding antibody. In this instance the ligand analogs are typically phosphoethanolamines according to formula

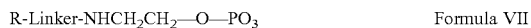

R-Linker-NHCH$_2$CH$_2$—O—PO$_3$    Formula VII wherein R is a reporter molecule and linker is a single covalent bond or comprises 1-20 non-hydrogen atoms to covalently attached the reporter molecule to phosphoethanolamine moiety. Typically the linker is a single covalent bond, See Compound 2.

In addition, it is also contemplated that serine and threonine residues conjugated to a reporter molecule also form part of the invention, See Compound 43 Example 8.

Theses non-fluorogenic ligand analogs that comprise phosphoethanolamine and phosphotyramide moieties are all capable of being quenched when bound by a ligand-binding antibody. Preferred ligand analogs that demonstrate a high degree of quenching typically comprise a xanthene reporter molecule wherein the linker is attached at the 6-position of the pendent phenyl ring including Compounds 7, 9, 12, 15, 19, 23, 25, 27, 33, 34 and 38. Most preferred ligand analogs for their ability to be quenched when bound by a phosphotyrosine ligand-binding antibody are Compounds 9, 15, 23 and 34.

Alternatively, these ligand analogs and others can be quenched when the ligand-detection reagent complex comprises a labeling protein (ligand analog-ligand-binding antibody-labeling protein complex).

B. Labeling Proteins

The labeling proteins are optionally part of the ligand-detection reagent wherein the labeling protein comprises a monovalent antibody fragment or a non-antibody protein and a covalently bound label. The label is selected from the group consisting of a chromophore, a fluorophore, a quenching moiety, a fluorescent protein and a phosphorescent dye. Typically the label is a fluorophore or a quenching moiety that is capable of absorbing energy from the reporter molecule of the ligand analog when bound by the ligand-binding antibody. The absorbed energy is either quenched (not re-emitted) or re-emitted at a longer wavelength resulting in a color shift of the detectable signal.

The labeling proteins of the present invention are monovalent antibody fragments or non-antibody monomeric proteins that have affinity for a region of a ligand-binding antibody. The regions of the ligand-binding antibody that can be bound by a labeling reagent include the Fc region, the Fab region, the kappa or lambda light chain region or a heavy chain region. When the labeling protein is derived from an antibody the monovalent fragment can be, anti-Fc, an anti-Fc isotype, anti-kappa light chain, anti-lambda light chain, anti-Fab region, or a single-chain fragment variable protein. Labeling proteins that are a non-antibody peptide or protein, are for example but not limited to, soluble Fc receptor, protein G, protein A, protein L, lectins, or a fragment thereof. The labeling proteins typically have affinity for the Fc region of the ligand-binding antibody but any region, except the binding domain, may be used as a binding site for the labeling protein. The Fc region is preferable because it is the farthest from the binding domain of the ligand-binding antibody and is unlikely to cause steric hinderance, when bound by a labeling protein, of the binding domain for the target ligand.

Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds). When IgG is treated with the enzyme papain, a monovalent antigen-binding fragment can be isolated, referred herein to as a Fab fragment. When IgG is treated with pepsin (another proteolytic enzyme), a larger fragment is produced, F(ab')$_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define both the Fab' and Fab portions of the antibody. It is well known in the art to treat antibody molecules with pepsin and papain in order to produce antibody fragments (Gorevic et al., Methods of Enzyol., 116:3 (1985)).

The monovalent Fab fragments of the present invention are produced from either murine monoclonal antibodies or polyclonal antibodies generated in a variety of animals that have been immunized with a foreign antibody or fragment thereof, U.S. Pat. No. 4,196,265 discloses a method of producing monoclonal antibodies. Typically, labeling proteins are derived from a polyclonal antibody that has been produced in a rabbit or goat but any animal known to one skilled in the art to produce polyclonal antibodies can be used to generate anti-species antibodies. However, monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art. It is a preferred embodiment of the present invention that the labeling proteins be generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments. As described in detail below, the labeling proteins are also covalently labeled with fluorophore labels when bound to the affinity column to eliminate incorporating label into the binding domain of the monovalent fragment. One of skill in the art will appreciate that this method can be used to generate monovalent fragments against any region of a ligand-binding protein and that selected peptide fragments of the ligand-binding antibody could also be used to generate fragments.

Alternatively, a non-antibody protein or peptide such as protein G, or other suitable proteins, can be used alone or coupled with albumin wherein albumin is attached with a label of the present invention. Preferred albumins of the invention include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are labeled in the same manner as the monovalent Fab fragments of the invention.

The labels of the present invention, by definition, are capable of absorbing energy from the reporter molecule when the ligand analog is bound by the ligand-binding antibody. The labels included a chromophore, a fluorophore, a quenching moiety, a fluorescent protein and a phosphorescent dye. Typically, these labels include fluorophores and quenching moieties, which include both fluorescent and essentially non-fluorescent compounds. The fluorophores (and chromophores) can be any of the compounds disclosed above for use as a reporter molecule.

Numerous quenching compounds are known to one of skill in the art including, but not limited to, compounds disclosed in U.S. Pat. No. 6,541,618 and U.S. Ser. No. 09/942,342 and cyanine compounds disclosed in U.S. Pat. Nos. 6,348,596; 6,080,868 and U.S. Ser. No. 60/491,783, xanthene compounds U.S. Pat. Nos. 6,399,392 and 4,318,846.

The labeling proteins can be independently attached to one or more labels of the present invention by a number of methods known to one skilled in the art and modification of such methods (PCT/US02/31416). Methods include, labeling in a solution or on an affinity column. For labeling in solution the monovalent antibody fragment or non-antibody protein is optionally modified to contain a reactive group and the label is modified to contain a reactive group, as described above, or is synthesized to contain a reactive group, as is typically the case with fluorophore labels wherein the reactive group facilitates covalent attachment. The modification of the labeling reagent to contain a reactive group includes (1) chemical addition of such a reactive group or (2) alternatively takes advantage of the disulfide bonds of the $F(ab')_2$ fragment wherein the fragment is reduced to break the bond and expose the thiol group that readily reacts with a reactive group on a label, as disclosed in U.S. Pat. No. 5,360,895. Typically, covalent attachment of the label to the fragment is the result of a chemical reaction between an electrophilic group and a nucleophilic group, See Table 1 for list of useful electrophile and nucleophile reactive groups. However, when a label is used that is photoactivated the covalent attachment results when the labeling solution is illuminated.

Briefly, for labeling in solution, the monovalent antibody fragments or the monomeric non-antibody proteins are incubated with a label that contains a reactive group and then the labeled anti-region Fab fragments or non-antibody monomeric proteins are isolated by size exclusion or affinity chromatography.

When a Fab fragment is to be labeled the whole antibody is cleaved with an enzyme, such as papain, to generate Fab monovalent fragments and the fragments are typically purified on an affinity column prior to addition of the label. The Fab fragment or non-antibody monomeric proteins are optionally chemically modified to contain a reactive group. However, for covalently attaching reactive fluorophore labels it has been found that this modification of the fragment of non-antibody protein is not necessary. The reactive label, typically a fluorophore or quenching moiety, are added to a solution of Fab fragments or non-antibody proteins and the labeling reagent is separated from excess label by size exclusion or affinity chromatorgraphy. The labeling proteins are then stored in an appropriate buffer.

Labeling in solution can have some drawbacks, especially when labeling of Fab fragments or non-antibody proteins with fluorophores. Thus, Fab fragments and non-antibody proteins of the present invention are preferably covalently attached to a fluorophore label when immobilized on an affinity column. The fragments and non-antibody proteins are immobilized on an affinity column that comprises a protein that the fragment has affinity for, typically IgG, and after immobilization a reactive fluorophore is added to the column wherein the fragments are labeled and unreacted fluorophores pass through the column.

The use of this affinity chromatography method avoids the incorporation of label into the binding domain of the Fab fragment or non-antibody protein. When Fab fragments are labeled with fluorophores using this method unexpected advantages were obtained wherein the fluorescent signal form fragments labeled on a column are brighter than fragments labeled in solution when the fluorophore and ratio of fluorophore to labeling reagent are held constant. Without wishing to be bound by a theory it is possible that the decreased brightness observed from the fragments labeled in solution is due to quenching of fluorphores that are bound in or near the binding domain by the high concentration of amine groups in the binding domain.

The affinity column is typically an agarose column that comprises either the selected region, such as the Fc region, or the entire antibody provided that the antibody or fragment thereof is the same species and isotype that was used to produce the antibodies that the labeling protein was generated from. However any column known to one skilled in the art can be used that allows for immobilization of a labeling protein and removal following attachment of the fluorophore or quenching label. Fab and Fab' fragments can both be labeled in this manner. However a free thiol group is not necessary and therefore Fab fragments are typically labeled using this method.

C. Ligand-Detection Reagent

Figure 1B:
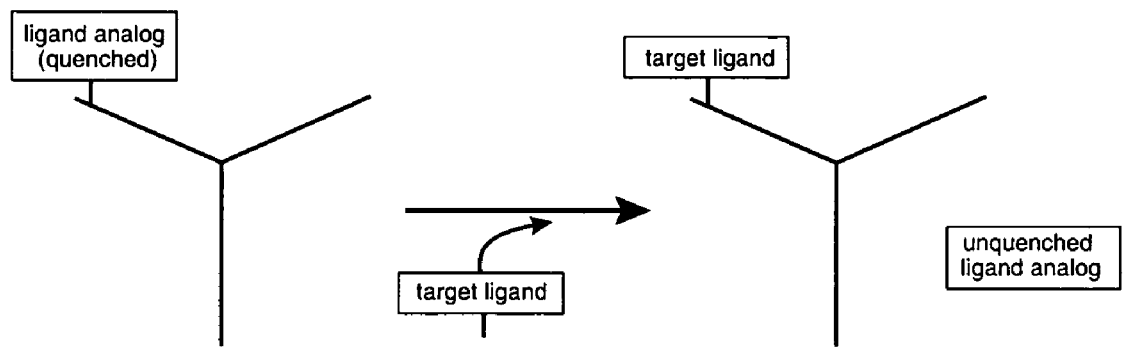

The present ligand-detection reagents comprise a ligand-binding antibody, a ligand analog and optionally a labeling protein, See FIG. 1. This reagent is formed by incubating the ligand-binding antibody, the ligand analog and optionally the labeling protein for sufficient amount of time to allow for a complex to form. The formation of the complex happens fairly rapidly, typically less than 30 minutes, preferably less than 15 minutes and most preferred the complex forms in 5 minutes or less.

For ligand-detection reagents that do not comprise a labeling protein, the ligand-binding antibody and ligand analog have been carefully screened and selected to result in a complex wherein the reporter molecule is quenched at least 60% by the ligand-binding antibody, See Example 22. Preferably, the reporter molecule is quenched more than 70% and most preferred the reporter molecule is quenched by 80% or more when bound by the ligand-binding antibody, See FIGS. 14A and B and Table 4 wherein Compound 15 demonstrates a Fmax/Fmin of 5.4, Compound 9 demonstrates a Fmax/Fmin of 3.2 and Compound 8 demonstrates a Fmax/Fmin of 1.3 when bound to the phosphotyrosine ligand-binding antibody wherein the larger the Fmax/Fmin value indicates a large percentage of quenching of the reporter molecule. This degree of quenching was unexpected and provides ligand-detection reagents that are easy to use and results in a large increase in fluorescence signal upon displacement of the ligand analog by the target ligand. This also indicated that the fluorinated xanthene dyes and rhodamine dyes are preferred to FITC and that attachment of the linker to the 6-position is preferred to attachment at the 5-position on the pendent phenyl ring of the xanthene dye moiety, The reporter molecules that are covalently attached to the ligand analog are preferably selected from the group consisting of a borapolyazaindacene, a coumarin, a xanthene, a cyanine, a fluorescent protein and a phosphorescent dye. Most preferred are borapolyazaindacene, fluorinated xanthene, fluorinated coumarin, including dyes sold under the trade name OREGON GREEN, BODIPY, PACIFIC BLUE and MARINA BLUE (Trade marks owned by Molecular Probes, Inc.) including any dyes disclosed in U.S. Pat. Nos. 6,162,931; 5,830,912; 4,774,339; 5,187,288; 5,248,782; and 5,433,896.

Ligand analogs containing these preferred reporter molecules were screened with ligand-binding antibodies specific for phosphotyrosine. Thus, preferred ligand-detection reagents for this application include a phosphotyrosine-binding antibody and the phosphotyramide and phosphotyrosinamide ligand analogs. Preferred ligand analogs include Compounds 6-38. Most preferred are Compounds 7, 9, 12, 15, 19, 23, 25, 27, 33, 34, 38 and 41-42. When the ligand-detection reagent comprise Compound 9 or 15 the respective reporter molecule is quenched by 80% or more.

Thus, a preferred embodiment of the present invention includes a ligand-detection reagent that comprises a ligand-binding antibody and a ligand analog to form an antibody-ligand analog complex wherein the ligand analog is selected from the group consisting of phosphotyramide, phosphotyrosinamide, phosphoethanolamine, phosphorylated kinase peptide substrate, phosphatase substrate and phosphorylated peptide and the analog is covalently bonded to a xanthene or borapolyazaindacene reporter molecule and the reporter molecule of ligand analog is capable of being quenched by the ligand-binding antibody.

In another aspect of the invention, fluorogenic ligand analogs are used resulting in fluorogenic ligand-detection reagents. In this instance, the ligand-detection reagent is fluorescent but when the target ligand displaces the ligand analog the fluorescent signal intensity deceases. Thus, the presence of a target ligand is determined by a decrease in fluorescence signal. Preferred fluorogenic ligand analogs include Compounds 4 and 5.

Alternatively, the ligand-detection reagent additionally comprises a labeling protein. The labeling protein comprises a label that is a fluorophore or a quenching moiety and a monovalent antibody fragment or a non-antibody protein wherein the label functions as an energy acceptor molecule. The labeling protein is incubated with the ligand-binding antibody and the ligand analog for a sufficient amount of time to form a ligand-detection reagent.

When preparing the ligand-detection reagent with a labeling protein using purified target-binding antibody, stock solutions of both the labeling protein and the ligand-binding antibody are typically near 1 mg/mL in an appropriate buffer, although more or less concentrated solutions are also suitable. Generally, the labeling protein is mixed in a molar ratio of at least one to 50 moles of labeling reagent to one mole of the ligand-binding antibody to be complexed. More commonly a ratio of at least one to as many as 10 moles of labeling protein per mole of target-binding antibody is combined. With an anti-Fc region Fab to a ligand-binding antibody, a molar ratio of approximately 2 to 10 is typical, more typically 3 to 5 (particularly for complexes in which the labeling protein has been labeled while immobilized on an affinity matrix). The ease of formation of the complex permits rapid optimization of the complex and assessment of the effect of variation in experimental parameters.

Complex formation appears to occur almost within the mixing time of the solutions (<1 minute) but the reaction typically is allowed to proceed for at least 5 minutes and can be longer before combining the ligand-detection reagent with the sample. Although complex formation can be reversed by addition of an unlabeled antibody that contains the same binding region, reversibility is very slow.

The non-covalent attachment of the labeling protein to the ligand-binding antibody optionally further comprises the addition of a capture component to remove excess labeling protein. For applications in which ligand-detection reagents of multiple primary antibodies from the same species (e.g. mouse monoclonal antibodies) or cross-reacting species (e.g. mouse and human antibodies) are to be used simultaneously or sequentially, it is necessary to quench or otherwise remove any excess labeling protein by use of a capture component or by other means to avoid inappropriate labeling of the sample. The most effective capturing components to capture excess labeling protein are those that contain the binding site of the labeling protein but are themselves not labeled, preferably an antibody or antibody fragment. Capture components may be free in solution or immobilized on a matrix, such as agarose, cellulose, or a natural or synthetic polymer, to facilitate separation of the excess capture component from the ligand-detection reagent. The capture component is optionally attached to a microsphere or magnetic particle. However, separation of excess labeling reagent is not essential for successful utilization of the invention, particularly when using a single ligand-binding antibody.

Appropriate matching of the reporter molecule and label are necessary to maximize the FRET between the reporter molecule and label for either optimal quenching or emission of energy at a longer wavelength. Many energy transfer dye pairs are known to one of skill in the art. Table 2 lists representative energy transfer pair dyes. This list is not intended to be limiting.

TABLE 2

| Donor Dye | Acceptor Compounds |
| --- | --- |
| Alexa Fluor 350 | Alexa Fluor 488; |
|  | QSY 36; |
|  | dabcyl |
| Alexa Fluor 488 | Alexa Fluor 546; |
|  | Alexa Fluor 555; |
|  | Alexa Fluor 568; |
|  | Alexa Fluor 594; |
|  | Alexa Fluor 647; |

TABLE 2-continued

| Donor Dye | Acceptor Compounds |
|---|---|
| Alexa Fluor 546 | QSY 35;<br>Dabcyl;<br>QSY 7;<br>QSY 9<br>Alexa Fluor 568;<br>Alexa Fluor 594;<br>Alexa Fluor 647;<br>QSY 35;<br>Dabcyl;<br>QSY 7;<br>QSY 9 |
| Alexa Fluor 555 | Alexa Fluor 594;<br>Alexa Fluor 647;<br>QSY 7;<br>QSY 9 |
| Alexa Fluor 568 | QSY 7;<br>QSY 9;<br>QSY 21 |
| Alexa Fluor 594 | Alexa Fluor 647;<br>QSY 21 |
| Alexa Fluor 647 | QSY 21 |
| Fluorescein | Tetramethylrhodamine;<br>QSY 7;<br>QSY 9 |
| IAEDANS | Fluorescein |
| BODIPY FL | Alexa Fluor 555;<br>QSY 9 |

Preferred energy transfer dye pairs are selected from the group consisting of Oregon Green 488-Alexa Fluor 555 dye pair, BODIPY-FL-Alexa Fluor 555 dye pair and BODIPY-FL-QSY 9 dye pair.

Therefore, a preferred embodiment of the present invention includes a ligand-detection reagent that comprises a ligand antibody, a ligand analog and a labeling protein to form a ternary complex wherein the ligand analog is selected from the group consisting of phosphotyramide, phosphoethanolamine, phosphorylated kinase peptide substrate, phosphatase substrate and phosphorylated peptide and the analog is covalently bonded to a xanthene reporter molecule and the labeling protein is an anti-Fc monovalent antibody fragment covalently bonded to a xanthene labeling moiety or non-fluorescent quenching moiety.

For the detection of phosphorylated molecules and enzymes that modify the degree of phosphorylation the phosphotyramide, phosphotyrosinamide and phosphoethanolamine ligand analogs are preferred, including Compounds 2 and 4-38. In addition, proteins or peptides that have been modified to be a ligand analog are also preferred. Table 3 contains a select list of some peptides that are specific for phosphotyrosine-binding antibodies that when conjugated to a reporter molecule of the present invention forms a ligand analog.

TABLE 3

| phosphotyrosine ligands | |
|---|---|
| Peptide | Sequence |
| pY-1 | ENDpYINASL |
| pY-2 | DADEpYLIPQQG |
| EGF Receptor | DADEpYL |
| M-2170 | IpYGEF |
| M-2165 | IYGEF |
| M-2035 | TEPEpYQPGE |
| N-1480 | DpYVPML |
| H-1546 | Biotin-EPQpYEEIPIYL |
| H-5458 | Biotin-EGPWLEEEEEAYGWMSF |
| pp60 | TSTEPQpYQPGENL |
| abl peptide | EAIYAAPFAKKK |
| DSIP | WAGGDASGE |
| pDSIP | WAGGDApSGE |
| pY | pY |

It is appreciated that the ligand-detection reagents can be designed to detect an unlimited number of target ligands utilizing a ligand analog and an appropriately matched ligand-binding antibody and that these reagents are in no way limited to the detection of phosphorylated biomolecules. Thus, ligand analogs and or target ligands are preferably selected from the group consisting of an amino acid, an enzyme, a phosphorylated kinase substrate, a peptide, a protein, a polysaccharide, a phosphatase substrate, a nucleoside, a nucleotide, an oligonucleotide, a nucleic acid, a hapten, digoxigenin, a cell surface receptor, a drug, a hormone, a lipid, a lipid assembly, a synthetic polymer, a polymeric microparticle, a biological cell and a virus wherein the ligand analog further comprise a reporter molecule. Preferred ligand analogs for the detection of phosphorylated biomolecules are selected from the group consisting of phosphotyramide, phosphotyrosinamide, phosphoethanolamine, kinase peptide substrate, phosphatase substrate and phosphorylated peptide. These ligand analogs are preferably conjugated to xanthene, borapolyazaindacene or coumarin reporter molecules.

C. Methods of Use

The ligand-detection reagents of the present invention can be used without limitation for the detection, analysis and monitoring of target ligands. These ligand-detection reagents are typically present in a ligand-detection solution, wherein the solution comprises a ligand antibody, a ligand analog and optionally a labeling protein to form a ternary ligand-detection reagent complex and a buffer. Appropriate buffer includes the family of Good's buffers or any buffer known to one of skill in the art that is typically used with antibodies.

Therefore, in one aspect of the invention a method for determining the presence of a target ligand in a sample comprises a) generating a ligand-detection reagent, wherein the ligand-binding antibody, the ligand analog and optionally the labeling protein are incubated together for a sufficient amount of time to form the ligand-detection reagent;

b) incubating the reagent with the sample for a sufficient amount of time for the ligand to displace the ligand analog from binding groove of the ligand-binding antibody;

c) illuminating the sample with an appropriate wavelength wherein the reporter molecule generates a detectable signal in the presence of the ligand whereby the ligand is detected.

The ligand-detection reagent is generated as described above. The reagent is incubated with the sample for a sufficient amount of time for the target ligand to displace the ligand analog. Typically this occurs very rapidly, usually within 5 minutes or less, preferably the displacement occurs within seconds of adding the ligand-detection reagent to the sample, See, Example 13. Illumination of the reporter molecule, as described below, depends on the reporter molecule of the ligand analog.

It is envisioned that any target ligand, wherein an appropriate ligand-binding antibody exists, can be detected using this method of the present invention. This includes the use of either a fluorogenic or non-fluorogenic ligand analog or the use of a labeling protein. A labeling protein is particularly preferred wherein further quenching is needed to easily resolve the detectable signal of bound verses unbound target ligand. Alternatively, the labeling protein is preferred wherein the ligand analog is not appreciably quenched by the ligand-binding antibody and the label is needed to function as a quenching moiety or a fluorophore to further shift the detectable signal from the reporter molecule signal.

In one aspect of the invention, the ligand detection reagents can be used to simultaneously detect multiple target ligands in a sample. This is accomplished by the simultaneous use of two (or more) detectably distinct ligand detection reagents. For instance, Compound 15 can be pre-complexed with an anti-phosphotyrosine antibody and utilized to detect the presence of phosphotyrosine. For the detection of a different target ligand such as the non-phosphorylated "pp60-peptide" in Table 3, a detectably distinct ligand analog with an appropriately matched ligand-binding antibody is employed. The two detectably distinct ligand detection reagents are mixed together and added to a sample or added sequentially, resulting in the simultaneous detection of two different target ligands in a sample. This process can be extended to an arbritary number of detectably distinct ligand detection reagents.

In a preferred embodiment, the method for determining the presence of a target ligand in a sample is used to detect phosphorylated biomolecules. In this instance the ligand-binding solution typically comprises a ligand-binding antibody that is capable of binding a phosphotyrosine, phosphoserine or phosphothreonine moiety, an appropriately matched ligand analog that is selected from the group consisting of phosphotyramide, phosphotyrosinamide, phosphoethanolamine, phosphorylated kinase peptide substrate, phosphatase substrate and phosphorylated peptide, and optionally a labeling protein whereby the amount of generated detectable signal from the reporter molecule is dependent on the presence of the phosphorylated target ligand. Preferably, the ligand analog is covalently bonded to a xanthene, coumarin, or borapolyazaindacene reporter molecule and the labeling protein, when present, is an anti-Fc monovalent antibody fragment covalently bonded to a xanthene labeling moiety or non-fluorescent quenching moiety.

Incubating phospho-tyrosine, -threonine or -serine binding antibodies with an appropriately matched ligand analog, generates the ligand-detection reagent. Preferably the ligand analog comprises a phosphophenol moiety including both phosphotyramide and phosphotyrosinamide ligand analogs. Optionally a labeling protein is incubated with the ligand analog and antibody to form a ternary complex. The labeling protein may be added prior to the addition of the ligand analog, after the addition of the ligand analog or all three components may be added simultaneously to form a ligand-detection reagent.

Following formation of the ligand-detection reagent in a ligand-detection solution, which comprises the reagent and an appropriate buffer, the ligand-detection reagent is incubated with the sample. If present, the target ligand will displace the ligand analog from the ligand-binding antibody almost immediately, less than 5 minutes. The ligand-detection reagent may be illuminated with an appropriate wavelength, before, during or after the reagent has been added to the sample. Alternatively, the reagent may be illuminated continuously from the time of formation to a time point after the reagent has been added to the sample.

This particular method also allows for the detection of enzymes that modify or create phosphorylated biomolecules, such as kinase and phosphatase enzymes, See Example 18.

Current commercial kinase and phosphatase assays are often time-consuming and require many steps such as electrophoresis, centrifugation, ELISA or immunoprecipitation. The present invention provides methods for the rapid, sensitive, and non-radioactive detection of a variety of selected kinases and phosphatases and provides, in addition, methods that are well suited for high-throughput screening. The kinase and phosphatase assays of the present invention also permit the screening of inhibitors and activators of, for example, tyrosine kinases and, in addition, also permit the monitoring and the purification of kinase and phosphatase enzymes. The enzyme substrate may be on a solid-or semi solid matrix such as an array including Hydrogel slides or present in a solution. The methods of the present invention are particularly advantageous for the monitoring of kinase and phosphatase activity in solution wherein the additional step adding the substrate to a matrix is not necessary. After the formation of the ligand-detection reagent the reagent is added along with enzyme substrate and enzyme to an appropriate buffer, such as kinase buffer comprising 50 mM Tris, pH 7.5, 10 mM $MgCl_2$, 1 mM EGTA, 0.01% Brij 35, 2 mM DTT and 500 μM ATP. The sample is typically continually illuminated and monitored or at set intervals for a period of time to determine the presence of kinase activity by the addition of phosphate groups to tyrosine, threonine or serine residues on an appropriate substrate. We have demonstrated that ATP does not displace the phosphotyramide ligand analog and therefore the observed detectable signal is related directly to the displacement of the ligand analog by the phosphorylated enzyme substrate, See Example 17.

In addition to a solution based assay, the present methods are also preferred for assay systems that employ immobilized enzyme substrate. In this instance, detection of the enzyme substrate on the array makes the methods of the invention far more sensitive than any known assays for kinases and phosphatases and use of fluorescence for detection on the array permits a higher density of labeling than is possible with radiochemical detection.

In addition to detecting a target ligand as an end point, the present ligand-detection reagents and methods for determining the presence of a target ligand in a sample can be employed to detect and monitor enzymes that directly or indirectly modify the target ligand.

The sample to be used with the methods of the present invention is defined to include any material that may contain a target ligand to which an antibody has affinity for. Typically the sample is biological in origin and comprises tissue, cell or a population of cells, cell extracts, cell homogenates, purified or reconstituted proteins, recombinant proteins, bodily and other biological fluids, viruses or viral particles, prions, subcellular components, synthesized proteins or reaction mixtures. Possible sources of cellular material used to prepare the sample of the invention include without limitation plants, animals, fungi, bacteria, archae, or cell lines derived from such organisms. The sample can be a biological fluid such as whole blood, plasma, serum, nasal secretions, sputum, saliva, urine, sweat, transdermal exudates, cerebrospinal fluid, or the like. Alternatively, the sample may be whole organs, tissue or cells from an animal.

Examples of sources of such samples include muscle, eye, skin, gonads, lymph nodes, heart, brain, lung, liver, kidney, spleen, solid tumors, macrophages, mesothelium, and the like.

Prior to combination with the ligand-detection reagent, the sample is prepared in a way that makes the target ligand, which is determined by the end user, in the sample accessible to the ligand-binding antibody. Typically, the samples used in the invention are comprised of tissue, cells, cell extracts, cell homogenates, purified or reconstituted proteins, recombinant proteins, biological fluids, synthesized proteins or reaction mixtures. Large macromolecules such as ligand-detection reagents tend to be impermeant to membranes of live biological cells. Treatments that permeabilize the plasma membrane, such as electroporation, shock treatments, or high extracellular ATP, can be used to introduce the ligand-detection reagents into cells. Alternatively, the immuno-labeled complexes can be physically inserted into cells, e.g. by pressure microinjection, scrape loading, patch-clamp methods, or phagocytosis. However, the desired target may require purification or separation prior to addition of the ligand-detection reagent, which will depend on the way the antigenic determinants are contained in the sample. For example, when the sample is to be separated on a SDS-polyacrylamide gel the sample is first equilibrated in an appropriate buffer, such as a SDS-sample buffer containing Tris, glycerol, DTT, SDS, and bromophenol blue.

When the sample contains purified target materials, the purified target materials may still be mixtures of different materials. For example, purified protein or nucleic acid mixtures may contain several different proteins or nucleic acids. Alternatively, the purified target materials may be electrophoresed on gels such as agarose or polyacrylamide gels to provide individual species of target materials that may be subsequently blotted onto a polymeric membrane or detected within the gel matrix. Preparation of a sample containing purified nucleic acids or proteins generally includes denaturation and neutralization. DNA may be denatured by incubation with base (such as sodium hydroxide) or heat. RNA is also denatured by heating (for dot blots) or by electrophoresing in the presence of denaturants such as urea, glyoxal, or formaldehyde, rather than through exposure to base (for Northern blots). Proteins are denatured by heating in combination with incubation or electrophoresis in the presence of detergents such as sodium dodecyl sulfate. The nucleic acids are then neutralized by the addition of an acid (e.g., hydrochloric acid), chilling, or addition of buffer (e.g., Tris, phosphate or citrate buffer), as appropriate.

In one aspect of the invention, the preparation of a sample containing purified target materials further comprises immobilization of the target materials on a solid or semi-solid support. Purified nucleic acids are generally spotted onto filter membranes such as nitrocellulose filters or nylon membranes in the presence of appropriate salts (such as sodium chloride or ammonium acetate) for DNA spot blots. Alternatively, the purified nucleic acids are transferred to nitrocellulose filters by capillary blotting or electroblotting under appropriate buffer conditions (for Northern or Southern blots). To permanently bind nucleic acids to the filter membranes, standard cross-linking techniques are used (for example, nitrocellulose filters are baked at 80° C. in vacuum; nylon membranes are subjected to illumination with 360 nm light). The filter membranes are then incubated with solutions designed to prevent nonspecific binding of the nucleic acid probe (such as BSA, casein hydrolysate, single-stranded nucleic acids from a species not related to the probe, etc.) and hybridized to probes in a similar solution. Purified proteins are generally spotted onto Hydrogel slides (Perkin Elmer), nitrocellulose or nylon filter membranes after heat and/or detergent denaturation. Alternatively, the purified proteins are transferred to filter membranes by capillary blotting or electroblotting under appropriate buffer conditions (for Western blots). Nonspecifically bound probe is washed from the filters with a solution such as saline-citrate or phosphate buffer. Filters are again blocked, to prevent nonspecific adherence of ligand-detection antibodies. Finally, samples are mixed with ligand-detection reagents. Nonspecifically bound ligand-binding antibodies are typically removed by washing.

When the sample contains cellular nucleic acids (such as chromosomal or plasmid-borne genes within cells, RNA or DNA viruses or mycoplasma infecting cells, or intracellular RNA) or proteins, preparation of the sample involves lysing or permeabilizing the cell, in addition to the denaturation and neutralization already described. Cells are lysed by exposure to agents such as detergent (for example sodium dodecyl sulfate, Tween, sarkosyl, or Triton), lysozyme, base (for example sodium, lithium, or potassium hydroxide), chloroform, or heat. Cells are permeabilized by conventional methods, such as by formaldehyde in buffer.

As with samples containing purified target materials, preparation of the sample containing cellular target materials optionally further comprises immobilization of the target materials on a surface such as a solid or semi-solid matrix. The targets may be arrayed on the support in a regular pattern or randomly. These supports include such materials as slides, polymeric beads including latex, optical fibers, and membranes. The beads are preferably fluorescent or non-fluorescent polystyrene, the slides and optical fibers are preferably glass or plastic or coated with a polymeric material such as Hydrogel slides, and the membrane is preferably poly(vinylidene difluoride) or nitrocellulose. Thus, for example, when the sample contains lysed cells, cells in suspension are spotted onto or filtered through nitrocellulose or nylon membranes, or colonies of cells are grown directly on membranes that are in contact with appropriate growth media, and the cellular components, such as proteins and nucleic acids, are permanently bound to filters as described above. Permeabilized cells are typically fixed on microscope slides with known techniques used for in situ hybridization and hybridization to chromosome "squashes" and "spreads," (e.g., with a reagent such as formaldehyde in a buffered solution). Alternatively, the samples used may be in a gel or solution.

In one aspect of the invention, the sample comprises cells in a fluid, such as ascites, hybridoma supernatant, or serum, wherein the presence or absence of the target in such cells is detected by using an automated instrument that sorts cells according to the detectable fluorescence response of the detectable moieties in the ligand-detection reagent bound to such cells, such as by fluorescence activated cell sorting (FACS). For methods using flow cytometry a cell population typically comprises individually isolated cells that have been isolated from other proteins and connective tissue by means well known in the art. For example, lymphocyte cells are isolated from blood using centrifugation and a density gradient. The cells are washed and pelleted and the ligand-detection solution added to the pelleted cells. In this instance, the ligand-detection solution typically comprises polymeric beads wherein either the ligand analog or ligand-binding antibody is covalently bonded to the beads.

At any time after addition of the ligand-detection reagent to the sample, the sample is illuminated with a wavelength of light selected to give a detectable optical response, and observed with a means for detecting the optical response. Equipment that is useful for illuminating the reporter molecule and/or label of the present invention includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard, expected response or ligand-detection reagent signal, indicates whether and to what degree the sample possesses a given characteristic, i.e. desired target ligand.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

III. Kits of the Invention

Suitable kits for preparing a ligand-detection reagent and for detection of a target ligand in a sample also form part of the invention. Such kits can be prepared from readily available materials and reagents and can come in a variety of embodiments. The contents of the kit will depend on the design of the assay protocol or reagent for detection or measurement. Generally, the kits will contain instructions, appropriate reagents, ligand analogs and optionally labeling protein, and solid supports, as needed. Typically, instructions include a tangible expression describing the reagent concentration or at least one assay method parameter such as the relative amounts of reagent and sample to be admixed, maintenance time periods for reagent/sample admixtures, temperature, buffer conditions and the like to allow the user to carry out any one of the methods or preparations described above.

In one aspect of invention a kit for the detection of a target ligand comprises a ligand analog, a ligand-binding antibody and optionally a labeling protein. In a preferred embodiment the kit comprises ligand-binding antibody that has affinity for a phosphorylated biomolecule and an appropriately matched ligand analog that is selected from the group consisting of a phosphotyramide, a phosphotyrosinamide, a phosphoethanolamine, phosphorylated a kinase peptide substrate, a phosphatase substrate, a phosphorylated peptide or a digoxigenin. If present, the labeling protein is preferably anti-Fc Fab fragment or anti-kappa Fab fragment and is bound to a fluorophore or quenching moiety.

A wide variety of kits and components can be prepared according to the present invention, depending upon the intended user of the kit and the particular needs of the user.

EXAMPLES

The following examples describe specific aspects of the invention to illustrate the invention and to provide a description of the methods for those of skill in the art. The examples should not be construed as limiting the invention, as the examples merely provide specific methodology useful in understanding and practicing the invention.

Example 1

Synthesis of Phosphorylethanolamine Ligand Analog, Compound 2

To an orange solution of BODIPY FL succinimidyl ester (Molecular Probes 2184, 200 mg, 0.51 mmol) in 20 mL anhydrous tetrahydrofuran was added a solution of ethanolamine (36 µL, 0.6 mmol) in 1 mL dioxane. The resulting cloudy orange mixture was stirred at room temperature for 3 hours, and concentrated in vacuo. The residue was purified by flash chromatography on silica gel using 10% methanol in chloroform as eluant to give the corresponding ethanolamine amide of BODIPY FL as 0.17 g (99%) of an orange powder: $^1$H NMR (CD$_2$Cl$_2$) δ 7.19 (s, 1H), 6.97 (d, 1H), 6.34 (d, 1H), 6.20 (s, 1H), 6.08 (br s, 1H), 3.65 (t, 2H), 3.36 (m, 2H), 3.26 (t, 2H), 2.66 (t, 2H), 2.57 (s, 3H), 2.30 (s, 3H); LRMS m/z 335 (335 calcd for C$_{16}$H$_{20}$N$_3$O$_2$BF$_2$).

Compound 1

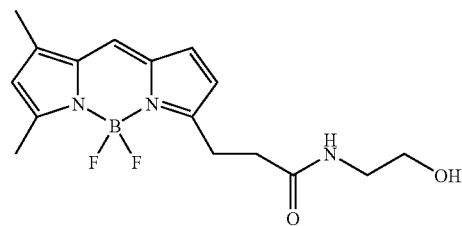

To a solution of BODIPY FL succinimidyl ester (Molecular Probes 2184, 50 mg, 0.13 mmol) in 5 mL dioxane was added a solution of O-phosphorylethanolamine (27 mg, 0.19 mmol) in 2 mL of 0.5 M triethylammonium bicarbonate. The resulting solution was kept at room temperature for 40 minutes and then concentrated to dryness. Water was twice evaporated from the residue, which was purified by chromatography on Sephadex LH-20 using water as eluant. Pure product fractions were pooled and lyophilized to give Compound 2 as an orange powder.

Compound 2

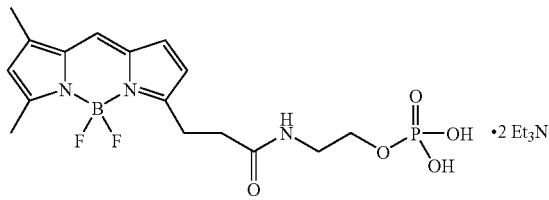

Example 2

Synthesis of Phosphotyramide Ligand Analog, Compound 4

To a solution of 4,4-difluoro-4-bora-3a,4a-diaza-s-indacene-3,5-dipropionic acid (Molecular Probes 6103, 0.10 g, 0.30 mmol) in 15 mL anhydrous THF under argon was added oxalyl chloride (78 µL, 0.89 mmol) and one drop of DMF. The volatiles were removed in vacuo after 15 minutes of stirring, leaving a residue of 4,4-difluoro-4-bora-3a,4a-diaza-s-indacene-3,5-dipropionyl chloride. This bis-acid chloride was dissolved in 15 mL anhydrous THF, and the resulting solution added dropwise to a solution of 4-aminophenol (98 mg, 0.90 mmol) and diisopropylethylamine (0.16 mL, 0.90 mmol) in 10 mL anhydrous THF with stirring. The resulting green-orange mixture was stirred at room temperature for 3 h and then quenched with 10% citric acid (75 mL). The resulting mixture was extracted with ethyl acetate (2×50 mL). The extract was washed with brine (1×), dried over sodium sulfate, and concentrated to an orange residue. Flash chromatography using methanol in chloroform gave Compound 3 as an orange powder: LCMS m/z 518 (518 calcd for $C_{27}H_{25}N_4O_4BF_2$).

Compound 3

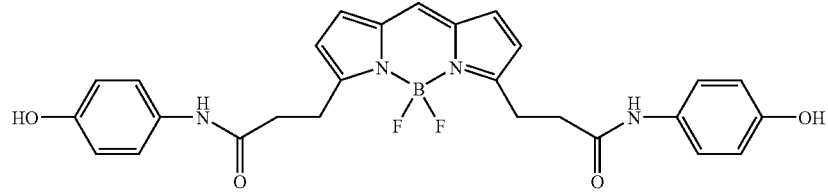

To a solution of 4,4-difluoro-4-bora-3a,4a-diaza-s-indacene-3,5-dipropionyl chloride (0.059 mmol) in 2 mL methylene chloride was added a solution of O-phosphoryl-4-aminophenol disodium salt (34 mg, 0.15 mmol) in 5 mL DMF/0.2 mL acetic acid. The resulting mixture was stirred at room temperature for two hours and then evaporated to dryness. Toluene was evaporated from the residue, which was purified by chromatography on Sephadex LH-20 using water as eluant to give Compound 4 as an orange powder.

Compound 4

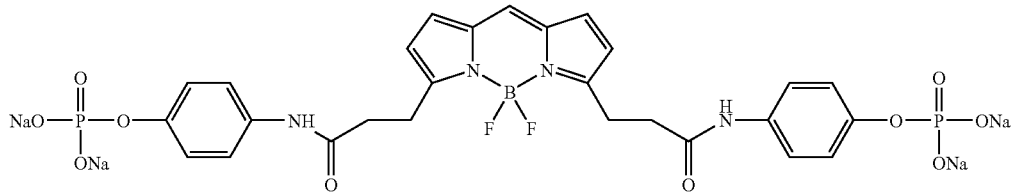

Example 3

Compound 5

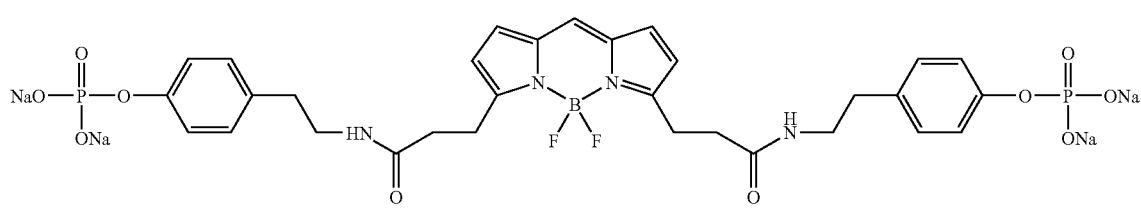

Synthesis of a Fluorogenic Phosphotyramide Ligand Analog, Compound 5

A 0.05M solution of 4,4-difluoro-4-bora-3a,4a-diaza-s-indacene-3,5-dipropionyl chloride in anhydrous dioxane is added dropwise to a 0.1M solution of 2.5 eq O-phosphotyramine disodium salt in water (pH 8-9) with stirring. After stirring at room temperature overnight, the volatiles are removed in vacuo. The residue is purified by chromatography on Sephadex LH-20 using water as eluant to give Compound 5 as an orange powder.

Example 4

Synthesis of Phosphotyramide Ligand Analog, Compound 6

To a solution of O-phosphoryl-4-aminophenol disodium salt (0.27 mmol) in 30 mL anhydrous DMF was added diisopropylethylamine (0.23 mL, 1.3 mmol) and a solution of 4,4-difluoro-4-bora-3a,4a-diaza-s-indacene-5,7-dimethyl-3-propionyl chloride in anhydrous dichloromethane (15 mL). The resulting mixture was stirred at room temperature overnight, then evaporated to dryness. The residue was dissolved in 1:1 methanol/water and then loaded onto a Sephadex LH-20 column, followed by gravity elution with water. Pure product fractions were combined and lyophilized to give Compound 6 as 10 mg of an orange powder.

Compound 6

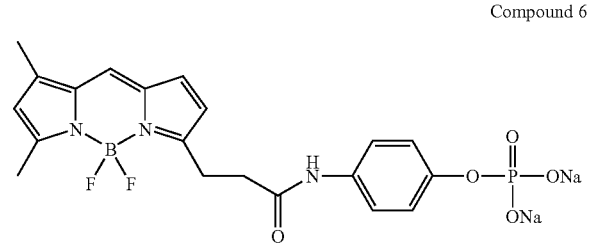

Example 5

Synthesis of Phosphotyramide Ligand Analog, Compounds 7-21 and 39

First, the intermediate O-phosphotyramine synthesized wherein the amine group was protected as t-BOC and the phosphorylation was done with $POCl_3$ and N,N-diisopropylethylamine in $CHCl_3$. The t-BOC group was removed by HCl in aqueous solution. Specifically this was accomplished wherein a suspension of tyramine (1.0 g, 7.29 mmol) in 50 ml of chloroform was added N.N-diisopropylethylamine (1.3 ml, 7.59 mmol) followed by addition of di-tert-butyl carbonate (1.60 g, 7.34 mmol) and the mixture was stirred at room temperature for 3 hours. The resulting reaction mixture was washed with 1% HCl (1×50 ml), water (2×50 ml) and then separated. Organic layer is dried over $Na_2SO_4$, filtered and concentrated under vacuum to give N-t-BOC protected intermediate. This intermediate (1.50 g, 6.33 mmol) is dissolved in 50 ml of chloroform and was added N,N-diisopropyl-ethylamine (1.09 ml, 6.36 mmol) and phosphorus oxychloride (580 µl, 6.34 mmol). After stirring at room temperature for 2 hours, all the chloroform was removed under vacuum and $H_2O$ (10 ml) was added, stirred at room temperature for 2 hours. The resulting aqueous solution was subjected to 2H-20 column by elution with water. From the combined desired fractions, O-Phosphotyramine (0.52 g) is obtained. (Rf=0.40 (silica gel, 20% water in acetonitrile)).

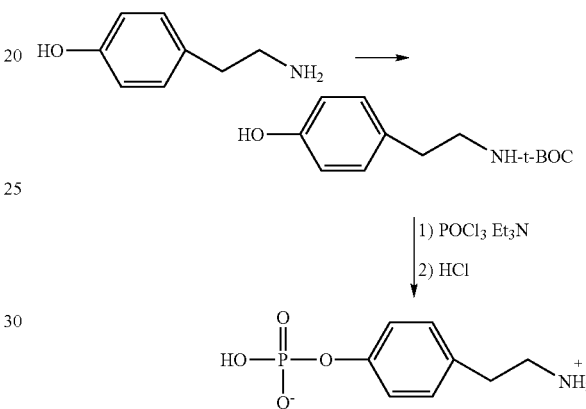

Next the succinimidyl ester version of the dye to O-Phosphotyramine was added to give Compound 7. This is accomplished wherein a solution of O-Phosphotyramine (3 mg, 0.01 mmol) and triethylamine (5 µl, 0.04 mmol) in 500 µl of water is added a solution of Dye-carboxylic acid, succinimidyl ester (6-isomer) (5 mg, 0.01 mmol) in 500 µl of DMF and the mixture is stirred at room temperature for 2 hours. To the reaction mixture is added ethyl acetate (10 ml) and stirred at room temperature for 5 minutes. The upper ethyl acetate layer is removed by decantation. The resulting aqueous layer is treated again with ethyl acetate (10 ml) and decanted. The remaining aqueous residue is purified by preparative TLC eluting with 20% H2O in acetonitrile. Obtained 4.0 mg of a pure desired product.

Compound 7

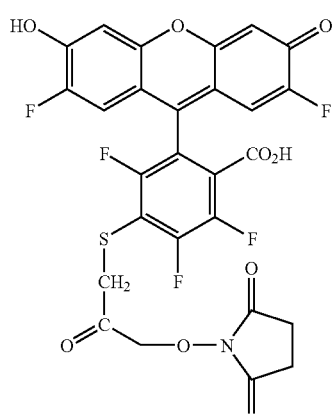

-continued

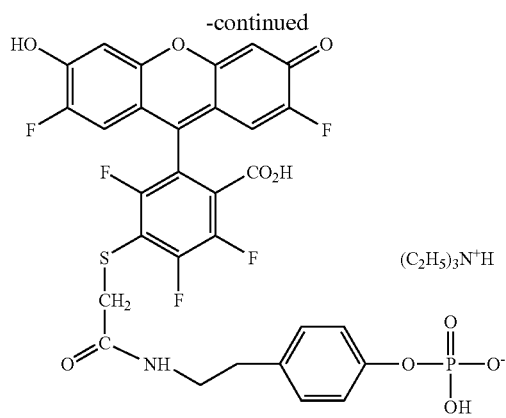
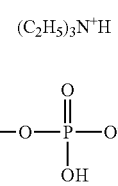

This synthesis scheme was followed to produce Compounds 8-21, wherein the same starting material was used but different reporter molecule compounds with a succinimidyl ester reactive group were conjugated to the O-Phosphotyramine intermediate. It is appreciated that numerous phosphotyramide ligand analogs can be made using this synthesis scheme wherein the desired reporter molecule with an appropriate reactive group such as succinimidyl ester is conjugated to the phosphotyramide moiety. In this instance the following compounds are not intended to be limiting.

Compound 8

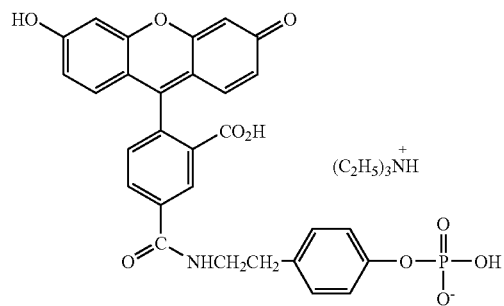

Compound 9

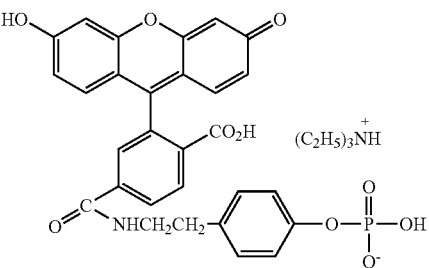

Compound 10

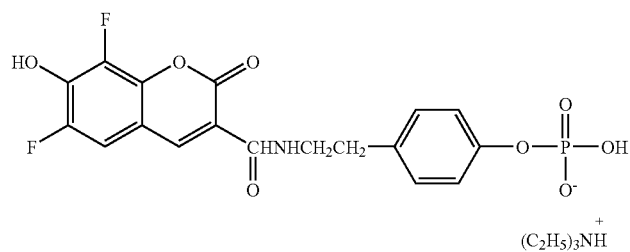

Compound 11

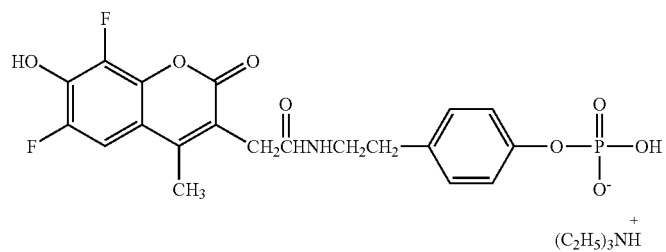

-continued
Compound 12
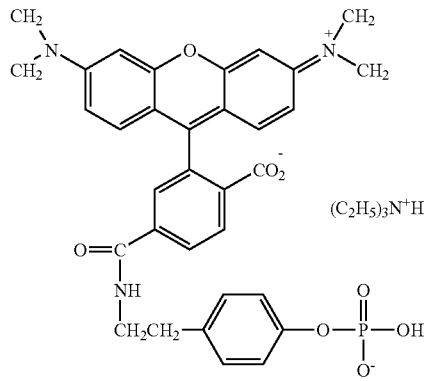
Compound 13
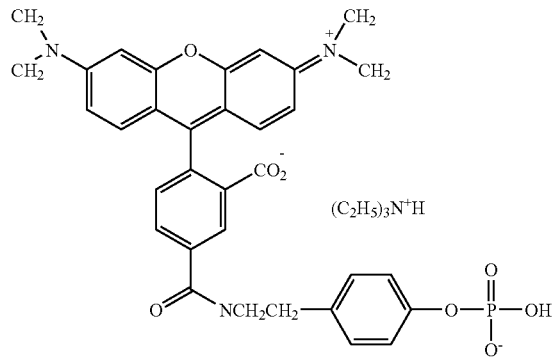
Compound 14
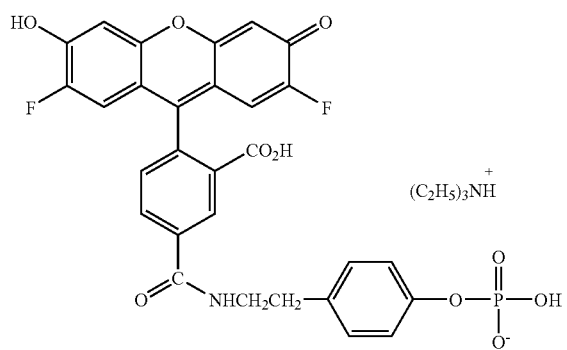
Compound 15
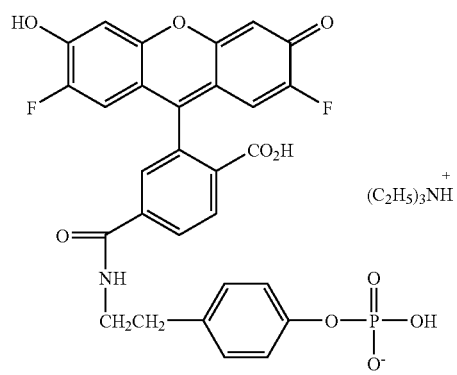
Compound 16
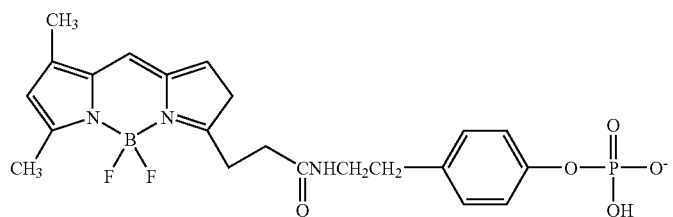
Compound 17
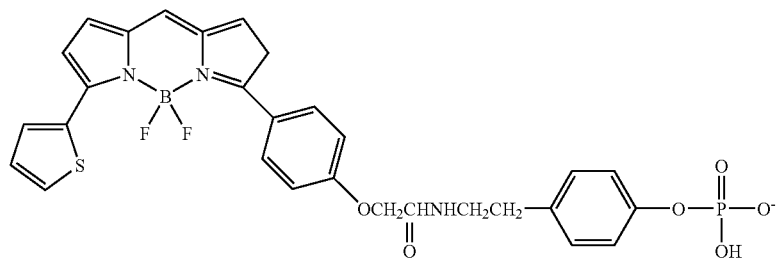

-continued

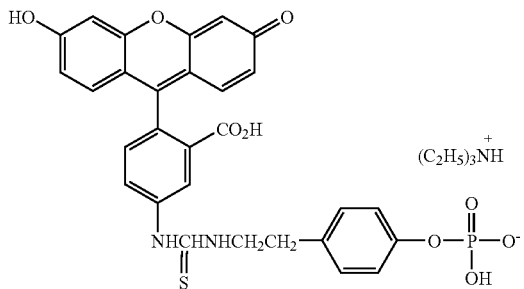
Compound 18

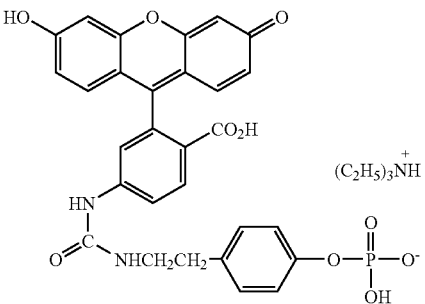
Compound 19

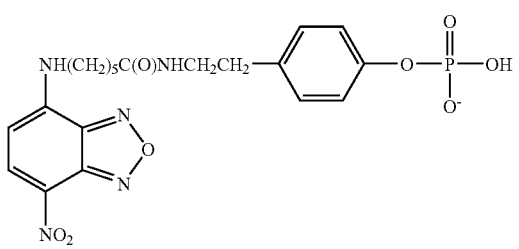
Compound 20

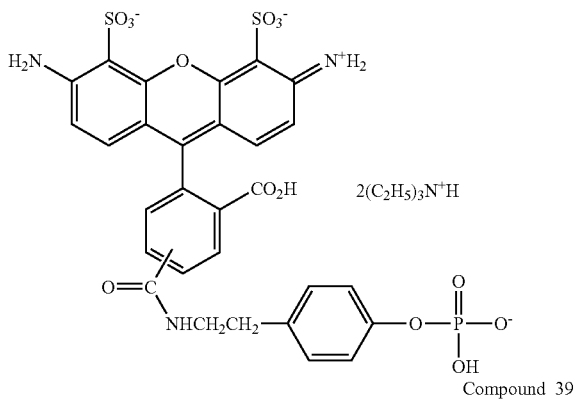
Compound 21

Compound 39

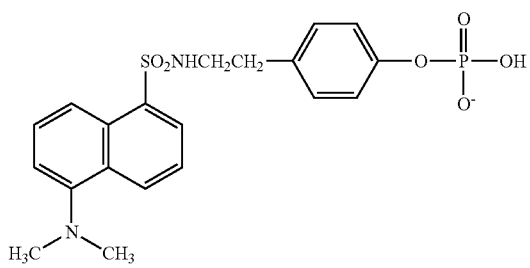

Example 6

Synthesis of Homolog of Phosphotyramide Ligand Analogs, Compounds 22-33 and 40

The following compounds were made with the same starting material but different reporter molecule compounds with a succinimidyl ester reactive group. First, the phosphotyramide intermediate was synthesized wherein a solution of mono N-t_BOC ethylenediamine hydrochloride (1.0 g, 4.84 mmol) and triethylamine (1.35 ml, 9.66 mmol) in 100 ml of dichloromethane is added N-succinimidyl 3-(4-hydroxyphenyl)propionate (1.27 g, 4.82 mmol) and the mixture is stirred at room temperature for 6 hours. It is washed with 0.5% HCl (1×100 ml) and then with water (2×100 ml). The separed organic layer is dried over $Na_2SO_4$, filtered and concentrated under vacuum to give 1.0 g of an off-white solid. The resulting solid is dissolved in 30 ml of dichloromethane and cooled with and ice-water bath. To this ice-water cooled solution is added triethylamine (540 µl, 3.82 mmol), followed by addition of phosphorus oxychloride (340 µl, 3.71 mmol). After stirring at room temperature for 1 hour, all the solvent is removed under vacuum. To the resulting residue is added a solution of sodium bicarbonate (84 mg, 1 mmol) in 10 ml of water and stirred at room temperature overnight. From the combined desired fractions, homolog of O-Phosphotyramine is obtained.

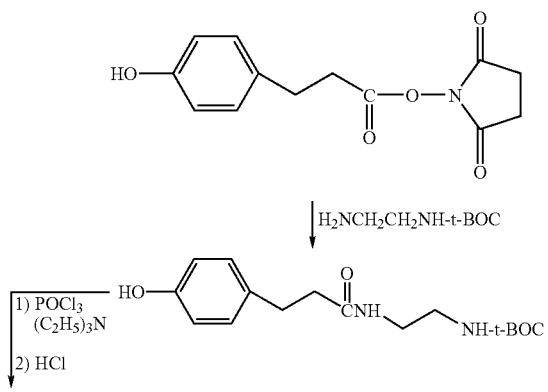

-continued

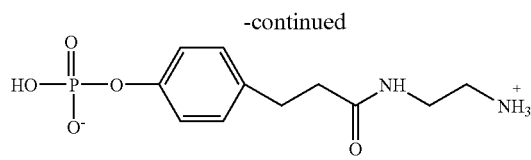

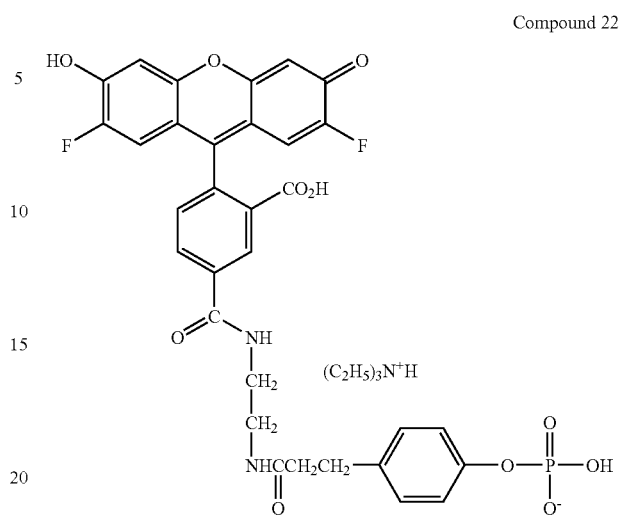

Compound 22

Next the succinimidyl ester version of the dye to homolog of O-Phosphotyramine was added to give Compound 22. This is accomplished wherein a solution of the homolog of O-Phosphotyramine (3 mg, 0.01 mmol) and triethylamine (5 µl, 0.04 mmol) in 500 µl of water is added a solution of Dye-carboxylic acid, succinimidyl ester (6-isomer) (5 mg, 0.01 mmol) in 500 µl of DMF and the mixture is stirred at room temperature for 2 hours. To the reaction mixture is added ethyl acetate (10 ml) and stirred at room temperature for 5 minutes. The upper ethyl acetate layer is removed by decantation. The resulting aqueous layer is treated again with ethyl acetate (10 ml) and decanted. The remaining aqueous residue is purified by preparative TLC eluting with 20% H2O in acetonitrile. Obtained 4.0 mg of a pure desired product.

It is appreciated that numerous homologs of phosphotyramide ligand analogs can be made using this synthesis scheme wherein the desired reporter molecule with an appropriate reactive group such as succinimidyl ester is conjugated to the phosphotyramide moiety. In this instance the following compounds are not intended to be limiting. Compounds 23-33 and 40 were made using this synthesis scheme.

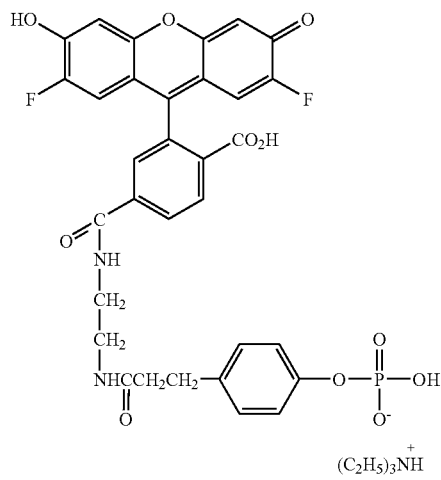

Compound 23

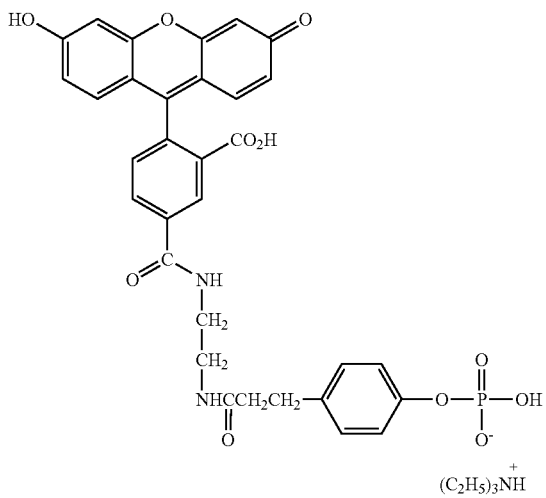

Compound 24

-continued
Compound 25
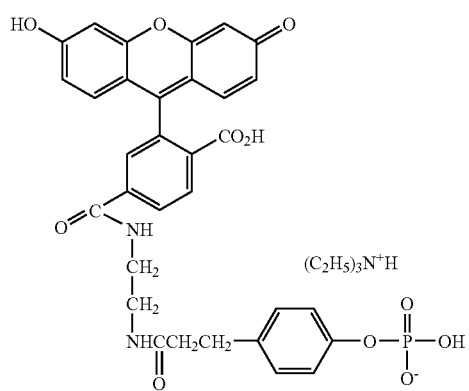
Compound 26
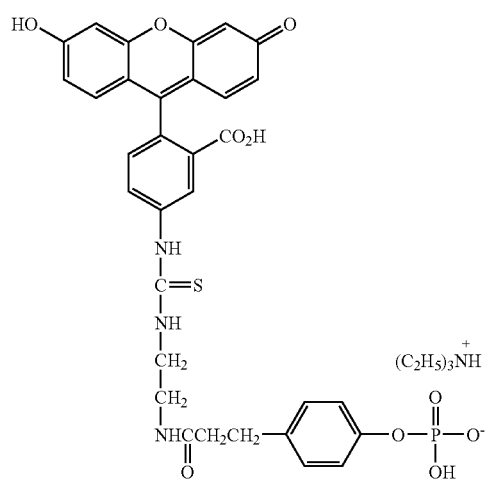
Compound 27
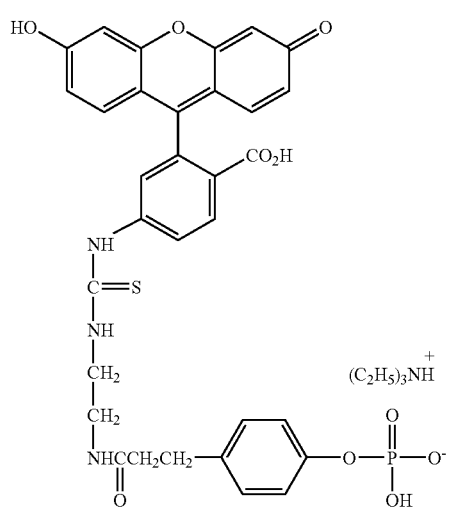
Compound 28
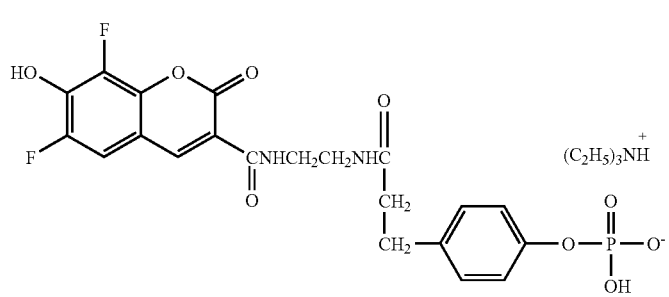
Compound 29
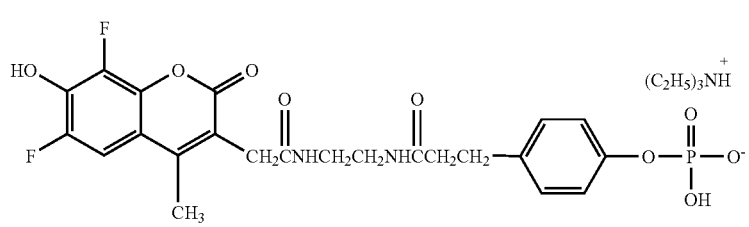

-continued
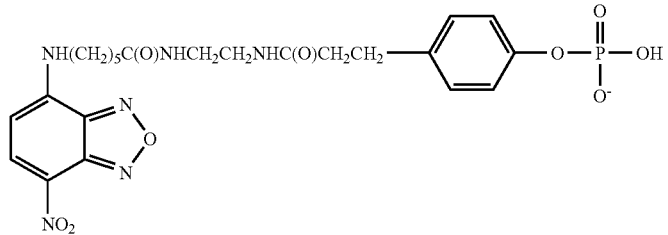
Compound 30
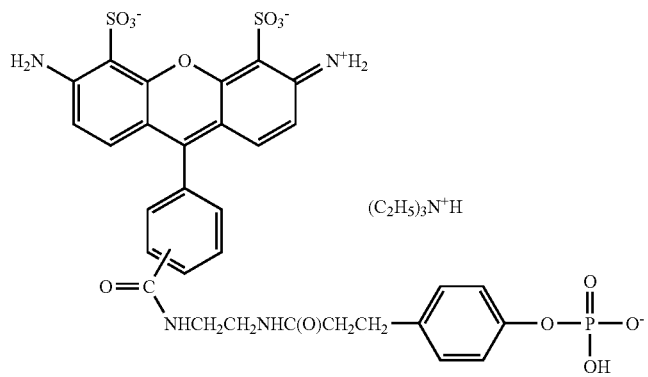
Compound 31
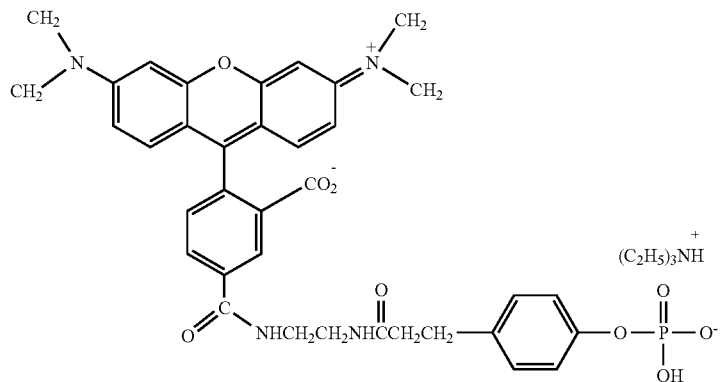
Compound 32
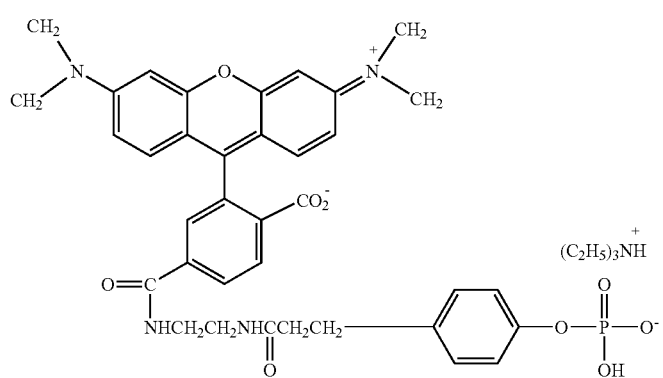
Compound 33

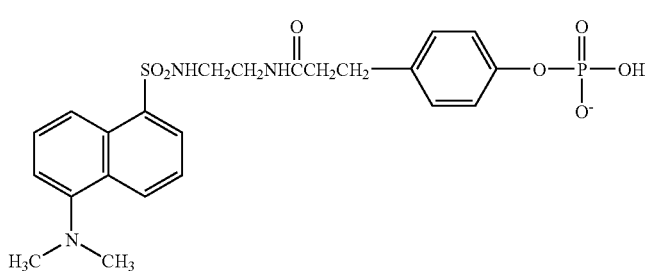

Compound 40

Example 7

Synthesis of Phosphotryosinamide Ligand Analogs, Compounds 34-38 and 41

The following compounds were made with the same starting material but different reporter molecule compounds with a succinimidyl ester reactive group. First, the phosphotryosinamide intermediate was synthesized wherein a solution of L-tyrosinamide (0.75 g, 4.17 mmol) and triethylamine (640 µl, 4.59 mmol) in 20 ml of THF was added di-tert-butyl dicarbonate (1.0 g, 4.59 mmol). After stirring at room temperature for 4 hours, 100 ml of chloroform was added and the mixture was washed with water (2×100 ml). The separated organic layer is dried over $Na_2SO_4$ and concentrated under vacuum to give 1 g of a white solid. This solid is dissolved in 30 ml of THF. To this solution is added di-tert-butyl diethylphosphoramidite (1.0 g, 3.93 mmol), followed by addition of tetrazole (750 mg, 10.70 mmol). After stirring at room temperature for 2 hours, a solution of 3-chloroperbenzoic acid (930 mg, 5.39 mmol) in 10 ml of dichloromethane was added while the reaction mixture was stirred under ice water bath. After stirring at room temperature for 1 hour, a 10% solution of sodium bisulfite in water (50 ml) was added and stirred at room temperature for 20 minutes. It was then extracted with chloroform (2×100 ml) and washed with 10% sodium bisulfite (2×100 ml) followed by washing with 10% sodium bicarbonate (1×100 ml). The separated organic layer was dried over sodium sulfate and concentrated under vacuum to give a crude fully protected intermediate. This crude intermediate was purified by column chromatography (silica gel) eluting with 5% methanol in chloroform to give 1.8 g of a protected intermediate. This is dissolved in 10 ml of TFA and stirred at room temperature overnight. All the TFA is removed under vacuum and the resulting residue is dissolved in about 2 ml of water and subjected to LH-20 column eluting with water. From the combined desired fractions 400 mg of a product is obtained as a white powder.

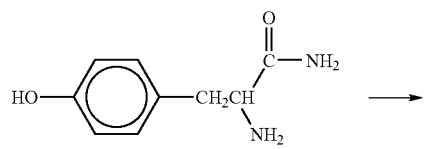

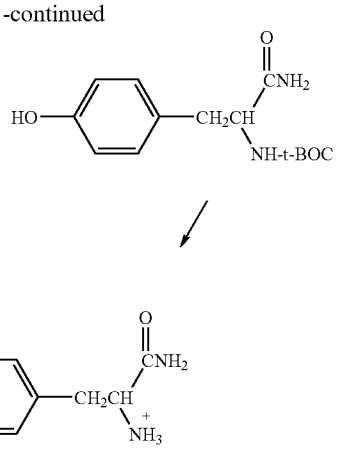

Next the succinimidyl ester version of a dye was added to phosphotryosinamide to give Compound 34. This is accomplished wherein a solution of the phosphotryosinamide compound (3 mg, 0.01 mmol) and triethylamine (5 µl, 0.04 mmol) in 500 µl of water is added to a solution of Dye-carboxylic acid, succinimidyl ester (6-isomer) (5 mg, 0.01 mmol) in 500 µl of DMF and the mixture is stirred at room temperature for 2 hours. To the reaction mixture is added ethyl acetate (10 ml) and stirred at room temperature for 5 minutes. The upper ethyl acetate layer is removed by decantation. The resulting aqueous layer is treated again with ethyl acetate (10 ml) and decanted. The remaining aqueous residue is purified by preparative TLC eluting with 20% H2O in acetonitrile. Obtained 4.0 mg of a pure desired product.

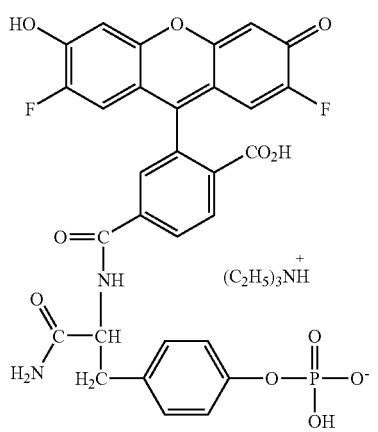

Compound 34

The following compounds were made with the same starting material but different reporter molecule compounds with a succinimidyl ester reactive group. It is appreciated that numerous phosphotryosinamide ligand analogs can be made using this synthesis scheme wherein the desired reporter molecule with an appropriate reactive group, such as succinimidyl ester, is conjugated to the phosphotryosineamide moiety. In this instance the following compounds are not intended to be limiting.

Compound 35

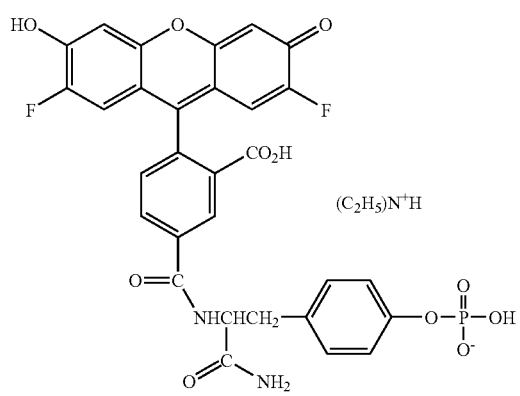

Compound 36

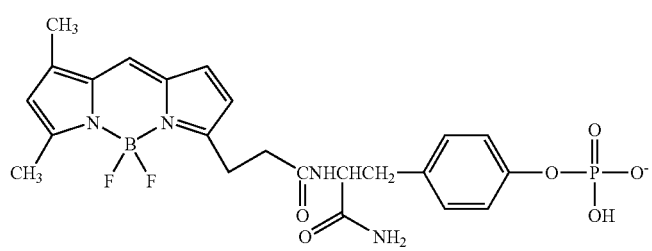

Compound 37

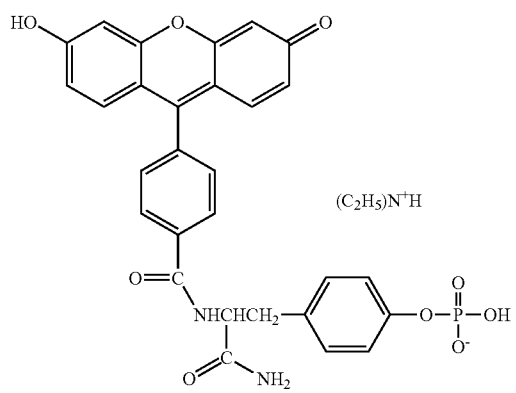

Compound 38

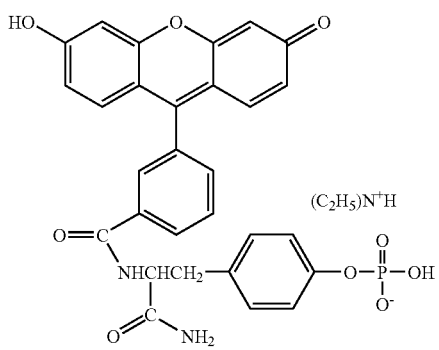

Compound 41

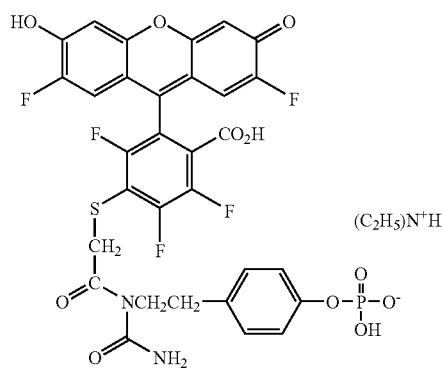

Compound 42

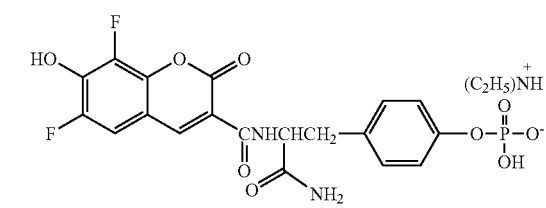

Example 8

Synthesis of Phosphoserine Ligand Analog, Compound 43

O-phosphorylserine, N-methylamide, N'-acylated with the 6-isomer of carboxy-2',7'-difluorofluorescein (B750-82-GEE45). The pH of a 0.10 M solution of O-phosphorylserine-N-methylamide was raised to 8.0 with aqueous sodium carbonate. A 100 µL aliquot (0.01 mmol) of this solution was added to a solution of Oregon Green 488 succinimidyl ester, 6-isomer (Molecular Probes 6149, 5.0 mg, 0.01 mmol) in 1.0 mL dioxane. The resulting mixture was stirred at room temperature for 4 hours, then filtered and lyophilized to afford Compound 43 as an orange powder.

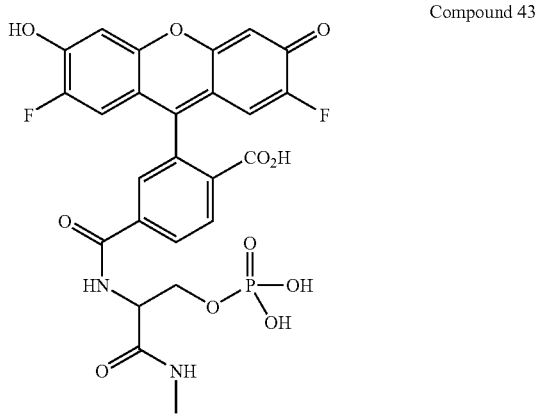

Compound 43

It is appreciated that other phosphoserine ligand analogs can be made using a similar synthetic scheme wherein a different reporter group with an appropriate reactive group such as succinimidyl ester is used to make numerous phosphoserine ligand analogs with various reporter groups. In this instance, Compound 43 is not intended to be limiting.

Example 9

Detection of Digoxigenin Employing a Ligand-Binding Antibody—Labeling Protein—Ligand Analog Ternary Complex To form a ligand-binding antibody labeling protein complex, mouse monoclonal anti-Digoxigenin antibody (Roche product #1333062) in 50 mM MOPS buffer, pH 7.2, was mixed in a 1:5 ratio with a Fab fragment of goat-anti-mouse kappa chain labeled with a quenching moiety (QSY 9) (Molecular Probes, Inc.). The degree of QSY 9 labeling on the Fab fragment was 1.7, determined by absorbance. The ligand-binding antibody+labeling protein complex (zero to 100 nm final concentration) was serially diluted two-fold in 90 µl buffer down a black, 96-well flat-bottom microplate precoated with 1% (w/v) bovine serum albumin. As a control, the ligand-binding antibody (anti-Digoxigenin antibody) was diluted in the plate in 90 µl buffer. After the serial dilution, 10 µl of the ligand analog (BODIPY FL Digoxigenin, Molecular Probes Inc., B-23460) (50 nM final) in 50 mM MOPS buffer, pH 7.2 was added to the same wells.

The resulting fluorescence intensity was measured on a Victor$^2$ microplate reader (Wallac), 1 read/well for 1 sec each at 50000V gain, excitation 485+/−17.5 nm, emission 535+/−12.5 nm. This demonstrates the ability of the quenching moiety on the labeling protein to diminish the fluorescent signal of the BODIPY dye on the ligand analog when a ternary complex is formed. As the amount anti-Digoxigenin/Fab fragment complex increases, the fluorescence of the BODIPY-FL Digoxigenin decreases. After the initial read, 1 µl of 100 µM ligand (unlabeled Digoxigenin) (Sigma, catalog # D-9026) in 50 mM MOPS buffer, pH 7.2, was added to all wells, and the resulting fluorescence intensity was measured on the same instrument at the same settings.

Figure 2:
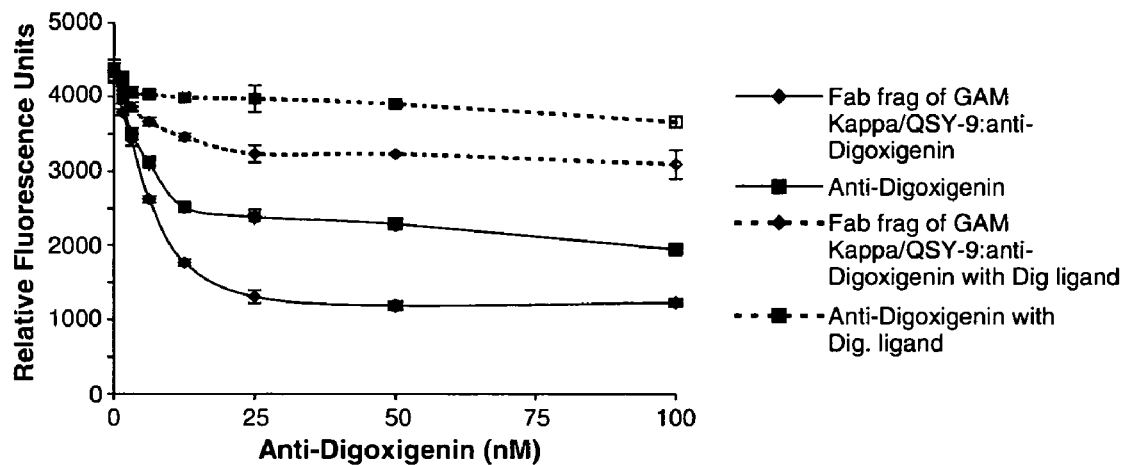
FIG. 2: Shows the amount of fluorescence quenching by BODIPY-FL Digoxigenin ligand analog when bound to the ligand-binding antibody/Fab fragment of goat anti-mouse kappa chain conjugated to QSY-9 complex. As the amount of anti Digoxigenin/Fab fragment increases, the fluorescence of the BODIPY-FL Digoxigenin decreases. When target ligand (Digoxigenin) is added the fluorescence quenching is partially relieved.

These results demonstrate that the ligand (unlabeled Digoxigenin) is capable of displacing the ligand analog to restore the fluorescent signal generated by the BODIPY fluorophore. When excess (1 µM) unlabeled Digoxigenin is added, the fluorescence quenching is partially relieved. See, FIG. 2.

Example 10

Binding of Ethanolamine Phosphate Ligand Analog (Compound 2) by Anti-Akt Antibody A 5 mM solution of BODIPY FL ethanolamine phosphate Compound 2 was made in water. A 2.5 mM solution of BODIPY FL ethanolamine (Compound 1) was made in 50% (v/v) DMSO, See Example 1. Rabbit anti-Akt polyclonal antibody (Cell Signaling Technology, catalog # 9611) was serially diluted in 5 µl 50 mM Tris buffer, pH 7.5 in a black, 384-well flat-bottom Packard ProxiPlate preblocked with 0.25% (v/v) Mowiol. After the antibody was serially diluted in the plate, 5 µl of either Compound 2 or Compound 1 was added to the same wells. The final concentration of both compounds in the wells was each 50 nM. The final antibody concentration in the wells was zero to 250 nM. The fluorescence intensity was measured on an EnVision microplate reader (Perkin Elmer), PMT 1 gain 155, PMT 2 gain 191, excitation light 76%, 100 flashes at 9 mM height. The ligand analog, Compound 2, is slightly quenched by the Rabbit anti-Akt polyclonal antibody when the ligand is bound by the antibody.

Example 11

Figure 3:
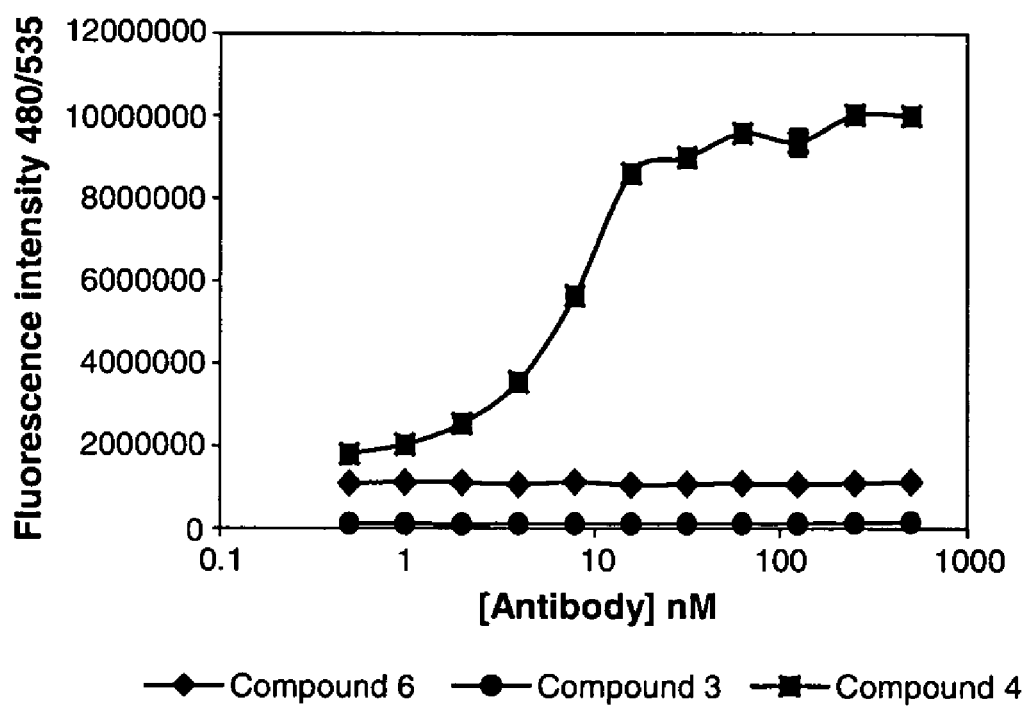
FIG. 3: Shows the use of a fluorogenic ligand analog (Compound 4) that upon interaction with the ligand-binding antibody exhibits fluorescence enhancement.

Fluorescence Enhancement of bis(acetamidophenylphosphate)-derivatized Dye Upon Binding to Antiphosphotyrosine Antibody Solutions of Compounds 3, 4 and 6 (100 nM) were prepared in 50 mM Tris-HCl, pH 7.5. 25 µl aliquots of these solutions were pipetted into the wells of a 384-well microplate. 25 µl aliquots of a serially-diluted 1 µM stock solution of P-Tyr-100 (U.S. Pat. No. 6,441,140) antiphosphotyrosine monoclonal antibody (Cell Signaling Technology, Beverly, Mass.) were added to the wells. The resulting samples contained 50 nM test compound and antibody concentrations ranging from 0.5 to 500 nM. Fluorescence intensity of the samples was measured on an EnVision microplate reader (PerkinElmer Life Sciences) using excitation/emission filter settings of 480/535 nm. The bis(acetamidophenylphosphate) (Compound 4) exhibits fluorescence enhancement upon interaction with the antibody, whereas the corresponding mono-substituted compound 6 and the parent bis(acetamidophenol) (Compound 3) do not. See, FIG. 3.

Example 12

Competitive Immunoassay with Compound 15 as the Ligand Analog, Anti-Phosphotyrosine Antibody as the Ligand-Binding Antibody and a Phosphotyrosine Peptide as the Target Ligand A 5 mM solution of Compound 15 was prepared in water. In 150 µl kinase buffer (50 mM Tris, pH 7.5, 10 mM MgCl$_2$, 1 mM EGTA, 0.01% Brij 35, 2 mM DTT, 100 µM ATP) several separate reactions were made containing: 1) 100 nM Compound 15; 2) 100 nM Compound 14+100 nM P-Tyr-100 monoclonal anti-phosphotyrosine antibody (Cell Signaling Technology, catalog # 9411); 3) 100 nM Compound 15+100 nM P-Tyr-100+10 µM phospho-pp60 c-src peptide (521-533) (TSTEPQY*QPGENL) from Bachem, catalog # H-3258; 4) 100 nM Compound 15+100 nM P-Tyr-100+10 µM phospho-abl peptide (EAIY*AAPFAKKK), custom peptide MPIJ6 from Anaspec. The resulting fluorescence was measured using a Hitachi F-4500 cuvette fluorimeter using 100 µl cuvettes. The F-4500 was set on 'emission scan', with an excitation at 470 nm, slit width of 5 nm, emission scan from 485-650 nm, slit width 5 nm, and the PMT gain was at 700 V.

Figure 4:
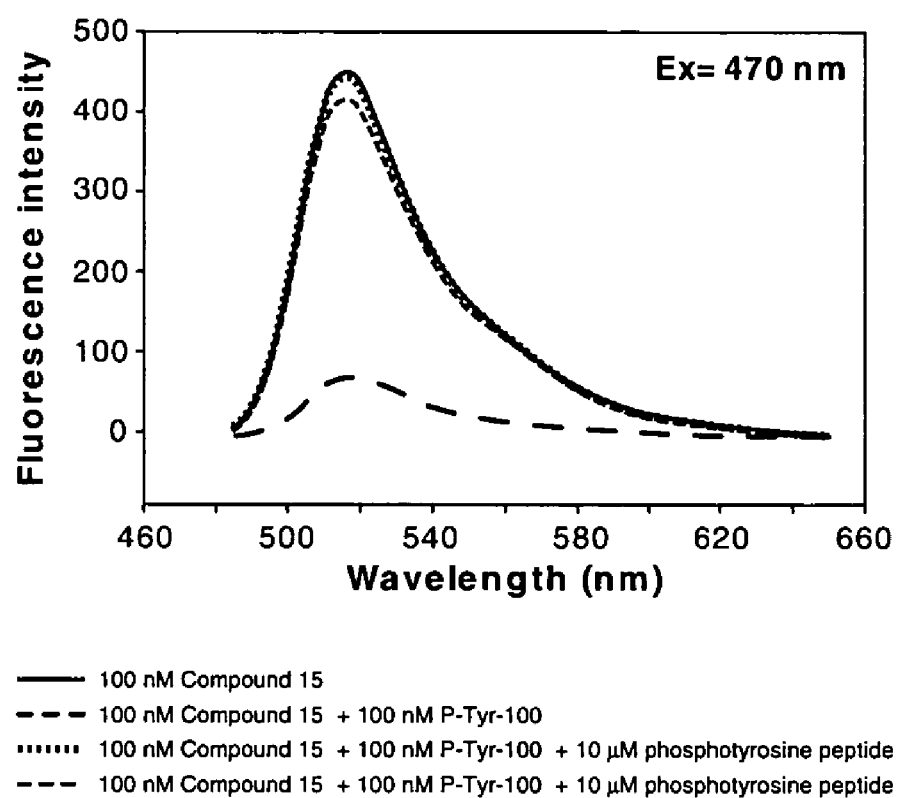
FIG. 4: Shows the quenching of the ligand analog (Compound 15) when bound by the ligand-binding antibody and the subsequent relief of quenching when target ligand, phosphotyrosine peptides, are added and the ligand analog displaced from the binding groove of the phosphotyrosine ligand-binding antibody.

Addition of P-Tyr-100 antibody to the ligand ligand analog (Compound 15) significantly quenched the reporter molecule of the ligand analog. Addition of either of two phosphotyrosine peptides relieved almost all of the quenching, demonstrating both the ability of the ligand-binding antibody to quench the ligand analog when bound to the antibody and the ability of the target ligand (phosphotyrosine peptide) to displace the ligand analog (Compound 15). See, FIG. 4.

Example 13

Rapid Displacement of the Ligand Analog by the Target Ligand

A 5 mM solution of Compound 15 was prepared in water. In 150 µl kinase buffer (50 mM Tris, pH 7.5, 10 mM MgCl$_2$, 1 mM EGTA, 0.01% Brij 35, 2 mM DTT, 100 µM ATP) a reaction was made containing 100 nM Compound 15+100 nM P-Tyr-100 monoclonal anti-phosphotyrosine antibody (Cell Signaling Technology, catalog # 9411). The fluorescence was measured over time using a Hitachi F-4500 fluorimeter (Ex 470, Em 510, slit width 5 nm for both wavelengths, PMT gain 700 V). After 15 seconds, 10 µM phospho-pp60 c-src peptide (521-533) (TSTEPQY*QPGENL) from Bachem, catalog # H-3258 was added.

Figure 5:
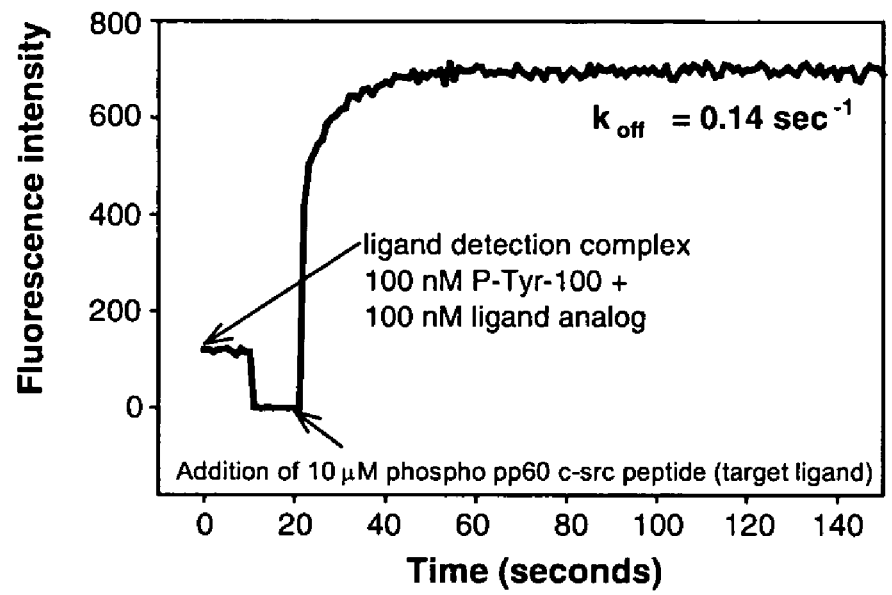
FIG. 5: Shows the off rate of the ligand analog (Compound 15) when target ligand is added to the ligand-detection reagent.

The off rate of Compound 15 (ligand analog) was calculated as 0.14 sec$^{-1}$, demonstrating the ability of the target ligand to displace the ligand analog very rapidly. See, FIG. 5.

Example 14

A 2 mM solution of Compound 34 was prepared in water. Two working stocks were prepared in kinase buffer (50 mM Tris, pH 7.5, 10 mM MgCl$_2$, 1 mM EGTA, 0.01% Brij 35, 2 mM DTT, 100 µM ATP): 1) 50 nM of Compound 34+100 nM P-Tyr-100 monoclonal anti-phosphotyrosine antibody (Cell Signaling Technology, catalog # 9411); 2) 100 µM phospho-pp60 c-src peptide (521-533) (TSTEPQY*QPGENL) from Bachem, catalog # H-3258. In two 384-well microplates, 2511 of the 50 nM Compound 34+100 nM P-Tyr-100 complex was added to 96 wells in each plate. To the same wells, 25 µl of either kinase buffer alone (48 wells each plate) or the 100 µM phospho-pp60 c-src peptide in kinase buffer (48 wells each plate) was added. The fluorescence was measured in a Victor$^2$ microplate reader (Wallac), 1 read/well for 0.2 sec each at 30000V gain, excitation 485+/−17.5 nm, emission 535+/−12.5 nm.

Figure 6:
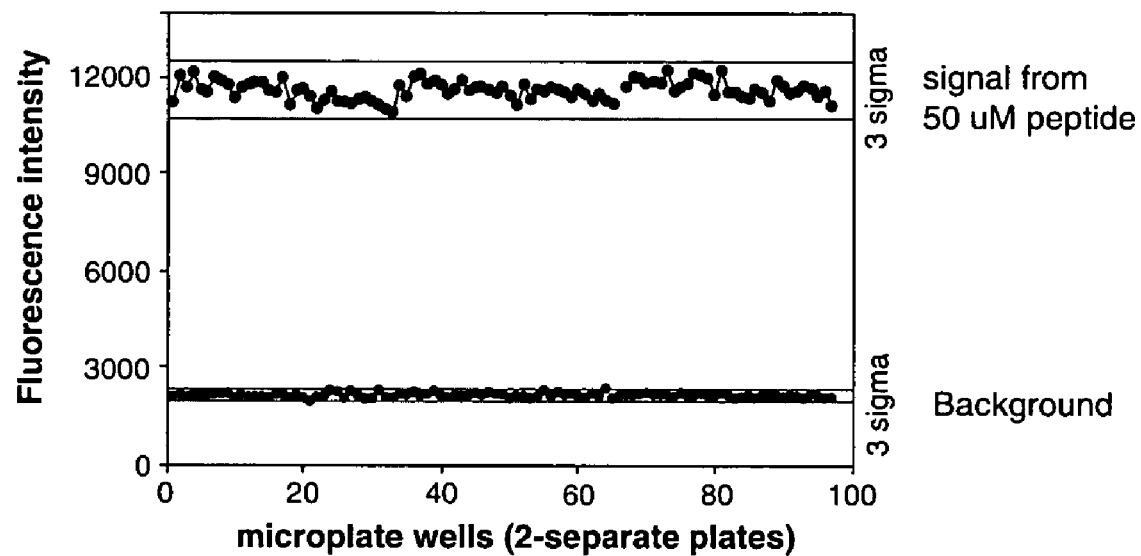
FIG. 6: Shows the Z-factor when using Compound 34 (ligand analog) demonstrating the large change in detectable signal after the target peptide displaces the ligand analog compared to before when the ligand-binding antibody binds the ligand analog.

The Z' statistic was calculated using equation 5 from Zhang, J.-H., Chung, T., D., Y., and Oldenburg, K. R. (1999) A simple statistical parameter for use in evaluation and validation of high throughput screening assays. *J. Biomol. Screen.* 4, 67-73. The Z' factor using data from both plates combined was calculated as 0.919, demonstrating the ability to differentiate between background signal and signal generate when the target ligand is bound by the antibody. In other words, there is a 4-fold increase in fluorescent signal after the ligand analog is displaced by the phosphorylated peptide. See, FIG. 6.

Example 15

A 5 mM solution of Compound 15 was prepared in water. In kinase buffer (50 mM Tris, pH 7.5, 10 mM MgCl$_2$, 1 mM EGTA, 0.01% Brij 35, 2 mM DTT, 100 µM ATP) 120 µM phospho-pp60 c-src peptide (521-533) (TSTEPQY*QPGENL) (Bachem, catalog # H-3258) was serially diluted three-fold across a microplate in 20 µl volume. 20 µl of 100 nM of Compound 15+200 nM P-Tyr-100 complex was added to all wells. The fluorescence intensity was measured on an EnVision microplate reader (Perkin Elmer), PMT 1 gain 155, PMT 2 gain 183, excitation light 60%, 100 flashes at 9 mM height.

Figure 7:
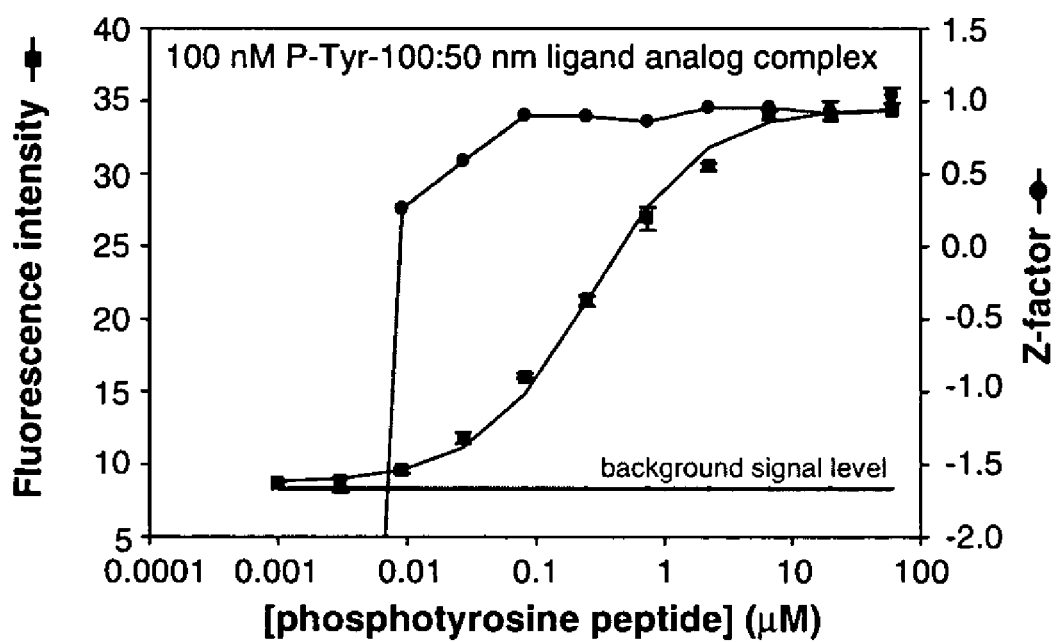
FIG. 7: Shows the Z-factor relative to the fluorescence intensity of the displaced ligand analog (Compound 15)

To generate the Z' scores in FIG. 7, the Z' factor was calculated using equation 5 from Zhang, J.-H., Chung, T., D., Y., and Oldenburg, K. R. (1999) A simple statistical parameter for use in evaluation and validation of high throughput screening assays. *J. Biomol. Screen.* 4, 67-73. This demonstrates the large increase in fluorescent signal after the ligand analog is displaced by the target ligand.

Example 16

A 5 mM solution of Compound 15 was prepared in water. In kinase buffer (50 mM Tris, pH 7.5, 10 mM MgCl$_2$, 1 mM EGTA, 0.01% Brij 35, 2 mM DTT, 100 µM ATP) 80 µM solutions of six different peptides or proteins were made: 1) phospho-pp60 c-src peptide (521-533) (TSTEPQY*QPGENL) (Bachem, catalog # H-3258); 2) non-phospho-pp60 c-src peptide (521-533) (TSTEPQYQP-GENL) (Bachem, catalog # H-3256); 3) phospho-DSIP peptide (WAGGDAS*GE) (SynPep, catalog # 3920); 4) phospho-RRA(pT)VA peptide (RRAT*VA) (Sigma, catalog V248A); 5) beta-casein (Sigma, catalog # C6905); 6) bovine serum albumin (Sigma, catalog # A7284). These peptides or proteins were serially diluted 2-fold in 20 µl in a 0.025% Mowiol-blocked 384-well black Packard OptiPlate. 20 µl of a 2× mix of 50 nM of Compound 15+100 nM P-Tyr-100 (Cell Signaling Technology, catalog # 9411) complex in kinase buffer was added to the wells. The fluorescence intensity was measured on an EnVision microplate reader (Perkin Elmer), PMT 1 gain 155, PMT 2 gain 183, excitation light 60%, 100 flashes at 9 mM height.

Figure 8:
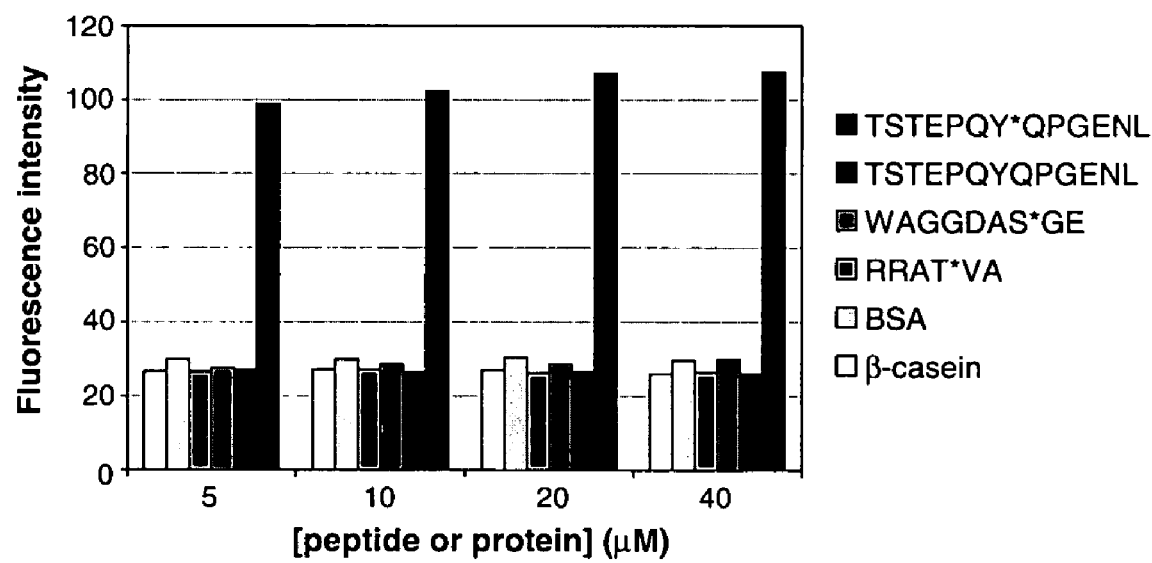
FIG. 8: Shows the selectivity of the ligand-binding antibody for the target ligand and ligand analog (Compound 15)

The phospho-pp60 c-src peptide is the only peptide or protein that significantly displaces the ligand analog (Compound 15), indicating that the reaction is specific for phosphotyrosine residues. See, FIG. 8.

Example 17

Displacement of Phosphotyramide Ligand Analog by Phosphotyrosine Containing Peptide but not by ATP A 5 mM solution of Compound 15 was prepared in water. Separate reactions of 100 nM Compound 15+/−100 nM P-Tyr-100 (Cell Signaling Technology, catalog # 9411) complexes were made in kinase buffer with various amounts of ATP (50 mM Tris, pH 7.5, 10 mM $MgCl_2$, 1 mM EGTA, 0.01% Brij 35, 2 mM DTT, with zero, 0.1, 0.25, 0.5, or 1 mM ATP). The fluorescence emission of each of the ten solutions was measured using a Hitachi F-4500 spectrofluorometer (Ex 450, Em 510, slit width 5 nm for both wavelengths, PMT gain 700 V). After the initial read, 10 μM phospho-pp60 c-src (10 μM final concentration) peptide (521-533) (TSTEPQY*QPGENL) (Bachem, catalog # H-3258) in kinase buffer was added to the antibody:ligand reactions, and the resulting fluorescence intensity was measured on the same instrument at the same settings.

Figure 9:
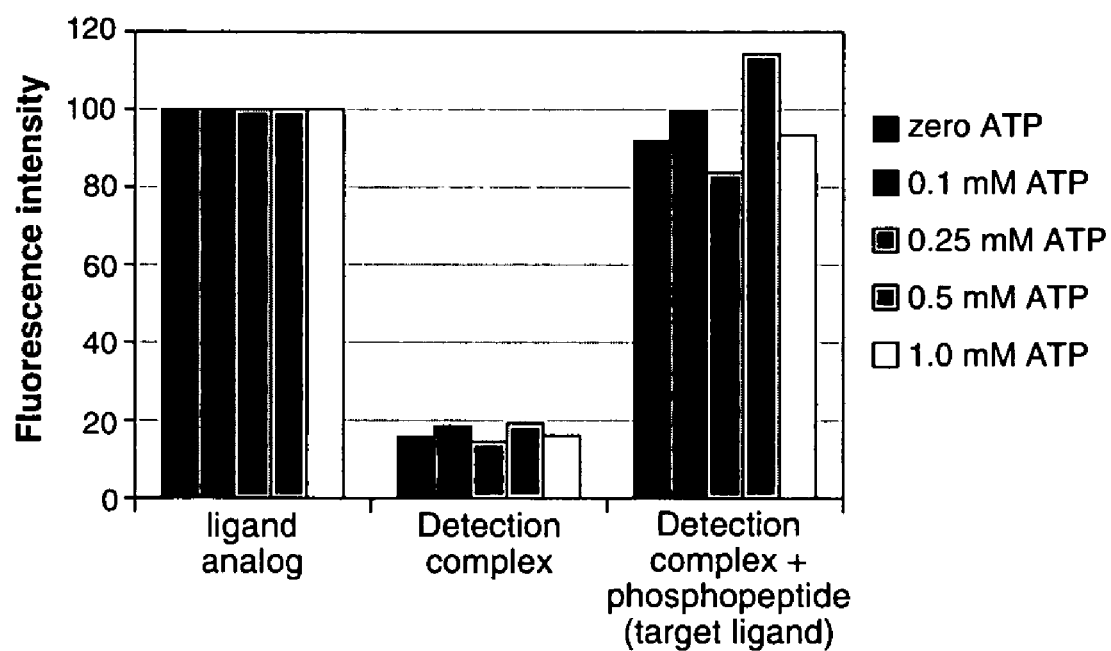
FIG. 9: Shows that the use of ATP in a kinase assay does not compete for binding of the phosphotyrosine ligand-binding antibody.

These data indicate that the assay is relatively insensitive to ATP concentrations. See, FIG. 9.

Example 18

Detection of Kinase Activity

A 5 mM solution of Compound 15 was prepared in water. Abl kinase (New England Biolabs, catalog # P6050S) was serially diluted 2-fold in 20 μl kinase buffer (50 mM Tris, pH 7.5, 10 mM $MgCl_2$, 1 mM EGTA, 0.01% Brij 35, 2 mM DTT, 500 μM ATP) in a 0.025% Mowiol-blocked 384-well black Packard OptiPlate. To the wells containing the serial dilution, 20 μl of either 400 μg/ml poly (Glu:Ala:Tyr) 6:3:1 ratio (Sigma, catalog # P-3899)+100 nM p-Tyr-100 antibody (Cell Signaling Technology, catalog # 9411)+50 nM Compound 15 in kinase buffer or 100 μM abl substrate peptide (custom peptide from AnaSpec, MPIJ-5 (EAIYAAPFAKKKC))+100 nM p-Tyr-100 antibody+50 nM Compound 15 in kinase buffer was added. After a one hour incubation the fluorescence intensity was measured on a Victor² microplate reader (Wallac), 1 read/well for 0.1 sec each at 20000 V gain, excitation 450+/−3 nm, emission 510+/−20 nm.

Figure 10:
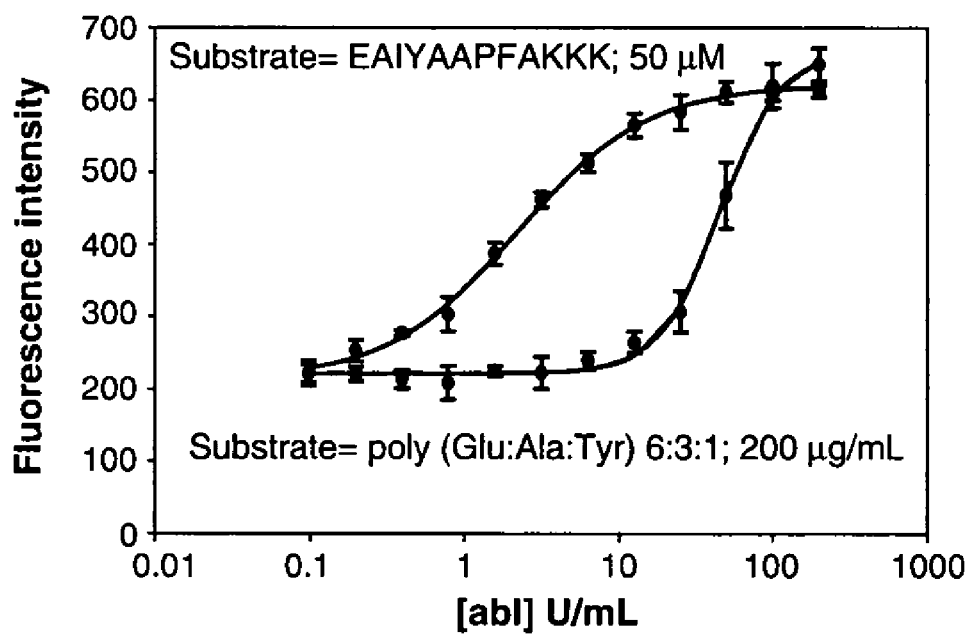
FIG. 10: Shows the detection of Abl kinase activity using Compound 15 as the ligand analog, phosphotyrosine ligand-binding antibody as the ligand-binding antibody and MPIJ-5 as the kinase substrate and subsequent target ligand.

The assay is capable of detecting Abl kinase activity wherein the phosphorylated peptides displace the ligand analog (Compound 15). The Abl kinase can phosphorylate both peptides, though it is more effective at phosphorylating the abl substrate peptide, MPIJ-5. See, FIG. 10.

Example 19

A 5 mM solution of Compound 15 was prepared in water. In kinase buffer (50 mM Tris, pH 7.5, 10 mM $MgCl_2$, 1 mM EGTA, 0.01% Brij 35, 2 mM DTT, 100 μM ATP) prepared 150 μl 333.3 μM staurosporine (Sigma, catalog # S-4400). The 333.3 μM staurosporine stock was serially diluted three-fold in 15 μl kinase buffer in a 0.025% Mowiol-blocked 384-well black Packard OptiPlate. To the same wells 10 μl of either kinase buffer alone, 10 μl of 333 Units/ml abl kinase (New England Biolabs, catalog # P6050S) in kinase buffer, or 10 μl of 125 Units/ml src kinase (Upstate Biotechnology, catalog # 14-326) in kinase buffer was added. The plate was centrifuged to ensure mixing and then incubated for 20 minutes at 37° C. To this, 25 μl of kinase buffer containing 200 nM Compound 15+200 nM p-Tyr-100 antibody (Cell Signaling Technology, catalog # 9411)+1.2 μM Fab fragment of goat-anti-mouse antibody labeled with Alexa Fluor® 555 as a quenching moiety+250 μg/ml poly (Glu:Tyr) 4:1 ratio (Sigma, catalog # P-0275). The plate was centrifuged again then incubated at 37° C. while monitoring the fluorescence intensity in a Victor² microplate reader (Wallac), 1 read/well for 0.1 sec each at 20000 V gain, excitation 450+/−3 nm, emission 510 +/−20 nm. After 45 minutes there was no increase in intensity in the abl-kinase-containing wells, so abl peptide substrate (custom peptide from AnaSpec, MPIJ-5 (EAIYAAPFAKKKC)) was added to a final concentration of 100 μM, and the plate incubated for an additional 50 minutes at 37° C.

Figure 11:
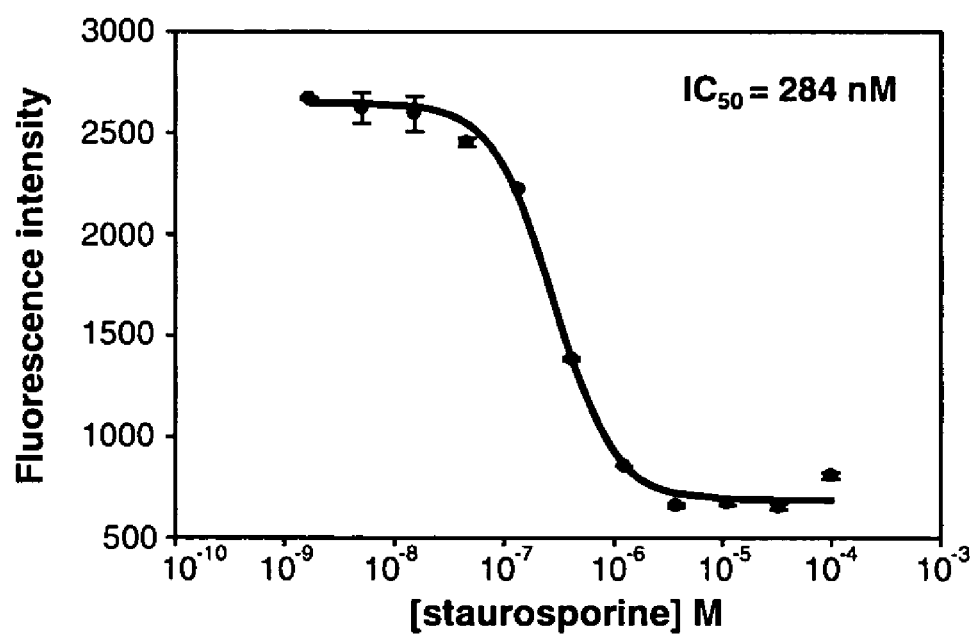
FIG. 11: Shows the ability of the ligand-detection reagent to detect the presence of an inhibitor of kinase activity (staurosporine).

The assay can determine the $IC_{50}$ of staurosporine, a model tyrosine kinase inhibitor. This indicates that the assay can be used to determine the $IC_{50}$ of unknown/experimental tyrosine kinase inhibitors. See, FIG. 11.

Example 20

A 4 mM stock of Compound 16 was made in 16% (v/v) DMSO. Three different antibodies were diluted to 1 μM in 50 mM MOPS, pH 7.2:1) p-Tyr-100 antibody (Cell Signaling Technology, catalog # 9411); 2) p-Tyr-69 antibody (BD Transduction Labs, catalog # 610430); 3) p-Tyr-20 antibody (BD Transduction Labs, catalog # 610000). A fourth antibody, the 4G10 antibody (Upstate Biotechnology, catalog # 05-321), was diluted to 400 nM in MOPS buffer. The antibodies were serially diluted in a microplate in 25 μl 50 mM MOPS, pH 7.2, buffer. 25 μl 100 nM Compound 16 in MOPS buffer was added to all wells. The fluorescence intensity was measured on an EnVision microplate reader (Perkin Elmer), PMT 1 gain 155, PMT 2 gain 187, excitation light 53%, 100 flashes at 9 mM height.

Figure 12:
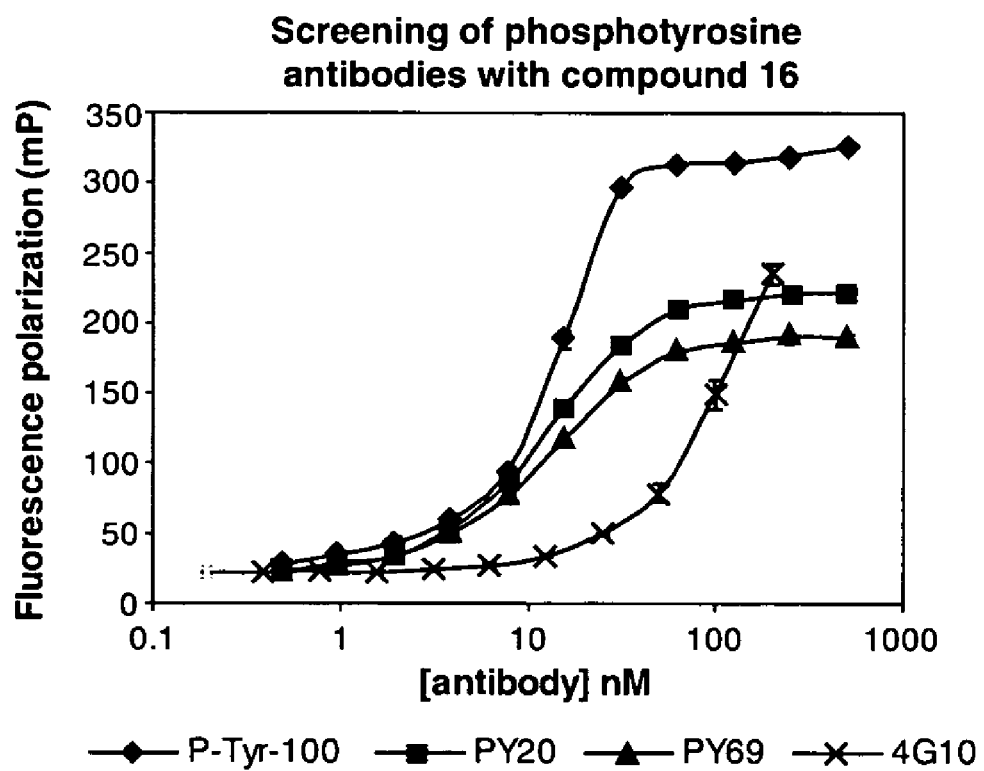
FIG. 12: Shows the screening of multiple phosphotyrosine ligand-binding antibodies to optimize the affinity of the ligand analog (Compound 16) for the ligand-binding antibody.

This experiment indicates that the p-Tyr-100 antibody from Cell Signaling Technology has the highest affinity for the ligand analog (Compound 16). See, FIG. 12.

Example 21

Phosphotyrosine Causes Minimal Displacement of Phosphotyramide-Dye Ligand Analogs from Antibody Binding Sites Solutions containing 100 nM ligand analog Compound 15 or ligand-detection complex (100 nM (B573-85-HCK)+100 nM P-Tyr-100 antiphosphotyrosine monoclonal antibody (Cell Signaling Technology, Beverly, Mass.)) were prepared in 50 mM Tris-HCl pH 7.5, 10 mM $MgCl_2$, 0.01% Brij-35, 100 μM ATP, 2 mM DTT, 1 mM EGTA. Fluorescence emission spectra of these samples were recorded on a Hitach F-4500 spectrofluorometer using an excitation wavelength of 470 nm. O-phosho-L-tyrosine (Sigma Chemical Co., St. Louis, Mo.) or phosphotyrosine peptide (phospho-pp60 c-src (521-533); TSTEPQY*QPGENL, Bachem California, Inc. Torrance, Calif.) at a concentration of 10 μM were added to samples of the detection complex and the resulting change in fluorescence was measured. See, FIG. 13.

Example 22

Method for Selecting Ligands for Use in Displacement Assay

TABLE 4

Ligands screened for efficacy in FIGS. 14A-D

| Compound Number | Ligand analog | $F_{max}/F_{min}$** |
|---|---|---|
| 15 | Oregon Green 488 6-phosphotyramide | 5.4 |
| 7 | Oregon Green 514 phosphotyramide | 4.0 |
| 8 | 5-FAM phosphotyramide | 1.3 |
| 9 | 6-FAM phosphotyramide | 3.2 |

TABLE 4-continued

Ligands screened for efficacy in FIGS. 14A-D

| Compound Number | Ligand analog | $F_{max}/F_{min}$** |
|---|---|---|
| 18 | 5-FITC phosphotyramide | 1.7 |
| 19 | 6-FITC phosphotyramide | 1.6 |

**obtained from data in FIG. B as the ratio of the fluorescence intensity at the lowest antibody concentration ($F_{max}$) to that at the highest antibody concentration ($F_{min}$).

Solutions of test compounds (100 nM) were prepared were prepared in 50 mM Tris-HCl pH 7.5, 10 mM MgCl$_2$, 0.01% Brij-35, 500 µM ATP, 2 mM DTT, 1 mM EGTA. 20 µl aliquots of these solutions were pipetted into the wells of a 384-well microplate. 20 µl aliquots of a serially-diluted 0.8 µM stock solution of P-Tyr-100 antiphosphotyrosine monoclonal antibody (Cell Signaling Technology, Beverly, Mass.) were added to the wells. The resulting samples contained 50 nM of each ligand analog (Compounds 15, 7, 8, 9, 18 and 19) and antibody concentrations ranging from 0.8 to 500 nM. Fluorescence polarization and intensity of the samples was measured on an EnVision microplate reader (PerkinElmer Life Sciences) using excitation/emission filter settings of 480/535 nm. Increasing fluorescence polarization as a function of antibody concentration (A) provides confirmation of ligand analog binding to the antibody. Ligand analogs exhibiting the largest possible signal changes (B) upon antibody binding (i.e. largest value of $F_{max}/F_{min}$ see Table 4) are preferred for displacement assays using a fluorescence intensity readout. Phosphotyrosine peptide, target ligand, (phospho-pp60 c-src (521-533); TSTEPQY*QPGENL, Bachem California, Inc. Torrance, Calif.) was then added to all samples at a concentration of 10 µM and the fluorescence intensity and polarization measurements were repeated (C, D). Preferred ligand analogs for displacement assays using a fluorescence intensity readout exhibit large fluorescence intensity upon phosphopeptide addition (i.e. C compared to B). Displacement of the ligand analogs from antibody is confirmed by depolarization of fluorescence (D compared to A). Based on these considerations, xanthene dye-based ligand analogs with a phosphotyramide moiety attached at the 6-position of the carboxyphenyl ring (e.g Compound 8) exhibit superior performance to the corresponding compounds derivatized at the 5-position (e.g. Compound 9). See, FIG. 14.

Example 23

Comparison of Phosphotyramide Ligand Analog to Phosphotyrosinamide Ligand Analog: Determination of Dissociation Constants for Antibody-Ligand Complexes Solutions of Compound 15 and Compound 34 (2 nM) were prepared in 50 mM Tris-HCl pH 7.5, 10 mM MgCl$_2$, 0.01% Brij-35, 500 µM ATP, 2 mM DTT, 1 mM EGTA, 0.5 mg/ml bovine serum albumin. 25 µl aliquots of these solutions were pipetted into the wells of a 384-well microplate. 25 µl aliquots of a serially-diluted 0.08 µM stock solution of P-Tyr-100 anti-phosphotyrosine monoclonal antibody (Cell Signaling Technology, Beverly, Mass.) were added to the wells. The resulting samples contained 1 nM test compound and antibody concentrations ranging from 0.02 to 40 nM. Fluorescence intensities of triplicate samples at each antibody concentration were measured on an EnVision microplate reader (PerkinElmer Life Sciences) using excitation/emission filter settings of 480/535 nm. The mean (n=3) fluorescence intensities were plotted against the corresponding antibody concentrations. Dissociation constants were determined from hyperbolic single-site saturation binding functions fitted to the experimental data by nonlinear regression analysis (SigmaPlot, Jandel Scientific Inc). The dissociation constants obtained were 2.0 nM for Compound 15+P-Tyr-100 and 1.7 nM for Compound 34+P-Tyr-100.

Example 24

Detection of a Target Ligand

Figure 15:
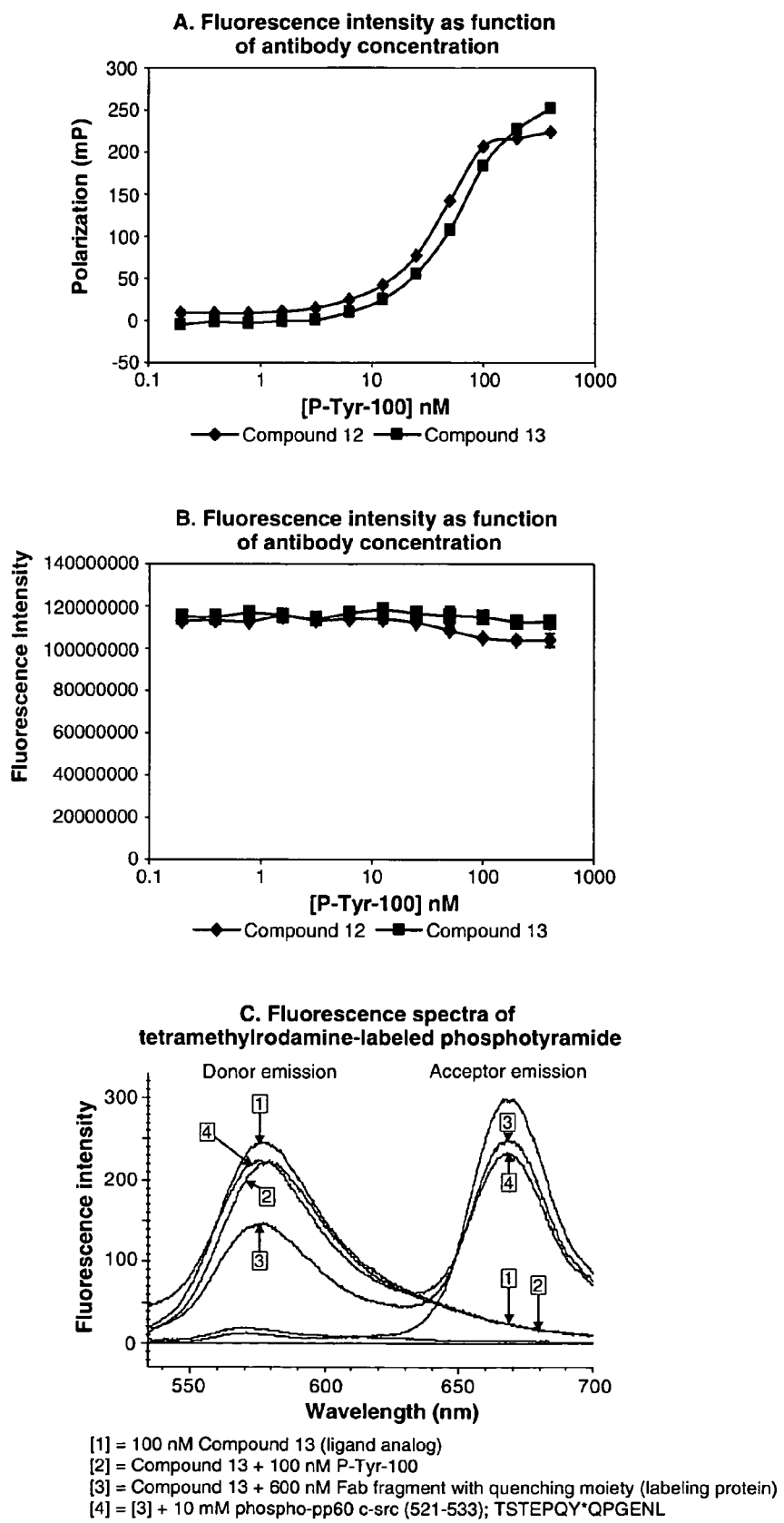
FIG. 15: Shows the ability of the labeling reagent to quench the reporter molecule when present as a ligand detection reagent ternary complex.

Compound 12 and Compound 13 were assessed for efficacy using the methods described in Example 22. The results of this assessment show large fluorescence polarization changes (Figure A), indicating binding of the ligands to the P-Tyr-100 antibody, but little or no analytically useful fluorescence intensity change (Figure B). The experiment shown in Figure C demonstrates that complexation of the mouse monoclonal anti-phosphotyrosine antibody (P-Tyr-100) with a secondary antibody labeled with a fluorescence resonance energy transfer acceptor dye (Alexa Fluor 647 dye-labeled F(ab')$_2$ fragment of goat anti-mouse IgG; "labeling protein") results in quenching of the fluorescence of Compound 13 that is reversed up addition of a phosphotyrosine-containing peptide. Samples containing 100 nM of Compound 13 and additional components identified in the figure legend were prepared in 50 mM Tris-HCl pH 7.5, 10 mM MgCl$_2$, 0.01% Brij-35, 100 µM ATP, 2 mM DTT, 1 mM EGTA. 100 µL volumes of these samples were transferred to microcuvettes. The fluorescence emission spectrum was recorded for each sample using a Hitachi F-4500 spectrofluorometer (excitation wavelength=520 nm). See, FIG. 15

Example 25

Flow Cytometric Assays

Coupling of antibodies to microspheres is a common methodology utilized to develop assays for analytes detected using flow cytometry instrumentation. Antibody-microsphere coupling procedures are typically performed so as to preserve antigen-binding activity. Hence, antibodies on microspheres will be capable of binding the ligand analog. Upon exposure of antibody-coupled microspheres to antigen, the ligand analog will be displaced from the microsphere, and a signal decrease will be observed in the flow cytometer. To generate flow cytometry assays with signals that increase upon analyte detection, a bound labeling protein (anti-Fc antibody fragment) can be complexed with the microsphere-coupled ligand-analog bound antibody. The observed signal from the labeling protein will be quenched, through FRET to the ligand analog. Upon exposure to the antibody-coupled microsphere to antigen, the ligand analog will be displaced, and the donor labeling protein signal will increase.

Example 26

The Use Enzyme Amplified Detectable Signal with an Enzyme Cofactor Conjugated Ligand Analog for a One Step Immunoassay The fluorophore moiety of the ligand-detection-reagent is replaced with an "enzyme-activating-factor" and then the signal associated with a single antigen-binding event is enzymatically amplified. For instance, the cofactor-ligandanalog is pre-complexed with the antibody wherein the ligand analog is displaced upon antigen binding. The types of cofactors utilized are: NAD(P)H, ATP, GTP, cAMP, coenzyme-A, FADH, hematin, glutathione, etc. Any small molecule that can be coupled to an antigen and still retain the ability to activate an enzyme-reaction are candidates for this approach. Antigen target detection is performed in the presence of the inactive (cofactor requiring) enzyme. The concentrations of the reagents are established, such that while the cofactor-ligand-analog is bound by antibody, the cofactor-requiring enzyme is not able to bind cofactor (not effective at competing with the antibody). Upon displacement of the cofactor-ligand-analog from the antibody, the cofactor-requiring enzyme binds the cofactor-ligand-analog and is activated. Any fluorogenic or chromogenic substrate is utilized that can be coupled to the activated enzyme and thereby significantly amplifying the single antigen-binding event. In this manner, the requirement for a second separate detection/amplification antibody to detect the antigen is obviated, Example 27

Efficacy of Secondary Antibody Labels as Fluorescence Resonance Energy Transfer Acceptors

TABLE 5

| Dye label on Fab (DOS)** | Sample A. 100 nM Compound 16 | Sample B. 100 nM Compound 16 + 100 nM P-Tyr-100 | Sample C. 100 nM Compound 16 + 100 nM P-Tyr-100 + 600 nM Fab |
|---|---|---|---|
| Unlabeled | 100 | 51 | 51 |
| Alexa Fluor 555 (3.8) | 100 | 53 | 36 |
| Alexa Fluor 594 (2.5) | 100 | 49 | 48 |
| Alexa Fluor 647 (2.8) | 100 | 49 | 47 |

Tabulated values are fluorescence intensities measured at 510 nm (excitation at 450 nm) expressed as percentages of the fluorescence intensity of 100 nM phosphotyramide ligand analog (Sample A) under the same conditions.
**DOS = degree of substitution i.e. the average number of dye labels per antibody.

Solutions containing (A) 100 nM phosphotyramide ligand analog, (B) 100 nM phosphotyramide ligand analog complexed with 100 nM P-Tyr-100 mouse monoclonal antiphosphotyrosine antibody and (C) 100 nM phosphotyramide ligand analog complexed with 100 nM P-Tyr-100 antiphosphotyrosine antibody and 600 nM Fab fragments of goat anti-mouse IgG were prepared in 50 mM Tris-HC1, pH 7.5. Corresponding sets for solutions were prepared for Fab fragments labeled with three different dyes and an unlabeled control. Fluorescence intensities at 510 nm (excitation at 450 nm) were measured on a Hitachi F-4500 spectrofluorometer and were expressed as percentages of the intensity of the free phosphotyramide ligand sample (Table 5). In all cases, binding of the ligand to the P-Tyr-100 antibody resulted in an approximately 50% decrease of fluorescence intensity. Addition of a labeled secondary antibody produced a further decrease in intensity only in the case of the Alexa Fluor 555 labeling dye, which has spectral characteristics that are consistent with efficient fluorescence resonance energy transfer from the BODIPY FL phosphotyramide ligand (Compound 16).

Example 28

The Use of Ligand Detection Reagent with Protein Microarray Assays

Antibodies are immobilized on a solid surface to form a microarray. Antibody arrays of this type are often utilized for analyte detection in a multi-step process. The microarrayed antibody captures the antigen, and then a second detection antibody is utilized to record the presence/absence of the captured antigen. Utilizing ligand-detection-reagents, this multi-step process can be eliminated, and antigen detection performed in the following manner. Microarraying antibodies either pre-bound with ligand-analog or subsequently exposed to ligand-ligand, will generate a signal associated with the bound ligand. Exposure of that antibody to a detectably distinct labeling protein, generates two independent signals associated with any given microarrayed antibody spot. Exposure of the protein microarray to antigen (target ligand) will cause displacement of the ligand-analog signal, but will not alter the labeling protein signal. For instance, for phosphotyrosine detection, a high affinity binding (yet not quenching) dye-antigens are utilized such as compound 12 or 13. Microarraying the antiphosphotyrosine-Compound 12 complexes will yield "bright-spots" on the protein microarray when detected with the appropriate excitation/emission filters. For graphical representation purposes, these data can be psuedo-colored "green." Pre-complexing the same antibodies with, for instance, a detectably distinct labeling protein will yield bright-spots when detected with the appropriate excitation/emission filters. For graphical representation purposes, these data can be psuedo-colored "red." In the absence of antigen, the images psuedo-colored "red" and "green" can be superimposed (overlay image) to generate a "yellow" spot, indicative of the absence of antigen. Exposure of the antibody microarray to target ligand will cause a displacement of the "green" signal and not effect the "red" signal. Hence, a single-step determination of the exposure of the antibody microarray to target ligand can be quantitated by observing to what degree the original "yellow-spots" change to "red-spots." For 100% displacement, pure red-spots would be observed, and for 0% analyte yellow-spots. Hence, protein-microarray spots are observed to change from "yellow-to-red" upon antigen detection—in a 1-step immunoassay detection scheme.

The reagents employed in the preceding examples are commercially available or can be prepared using commercially available instrumentation, methods, or reagents known in the art or whose preparation is described in the examples. It is evident from the above description and results that the subject invention is greatly superior to the presently available methods for determining the presence of a target ligand in a biological sample. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference to the same extent as if each individual publication, patent or patent application was specifically and individually indicated to be incorporated by reference.

What is claimed is:

1. A fluorescent phosphophenol ligand analog according to formula

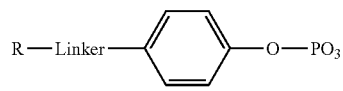

wherein R is a reporter molecule; and
linker is a single covalent bond or consists of hydrogen and non-hydrogen atoms selected from the group consisting of C, N, O, S and P, wherein the linker has less than 10 non-hydrogen atoms;
with the proviso that when the linker is —NHCH$_2$CH$_2$— that the reporter molecule is not FITC.

2. The ligand according to claim 1, wherein the fluorescent phosphophenol ligand analog is

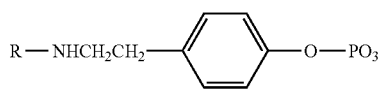

3. The ligand analog according to claim 1, wherein the R is a reporter molecule that is a borapolyazaindacene, a coumarin, a xanthene, a cyanine, a fluorescent protein or a phosphorescent dye.

4. A fluorescent phosphophenol ligand analog according to formula

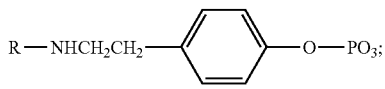

wherein R is a reporter molecule that is a borapolyazaindacene, a coumarin, a xanthene, a cyanine, a fluorescent protein or a phosphorescent dye;
with the proviso that the reporter molecule is not FITC.

5. The ligand analog according to claim 4, wherein the ligand analog is

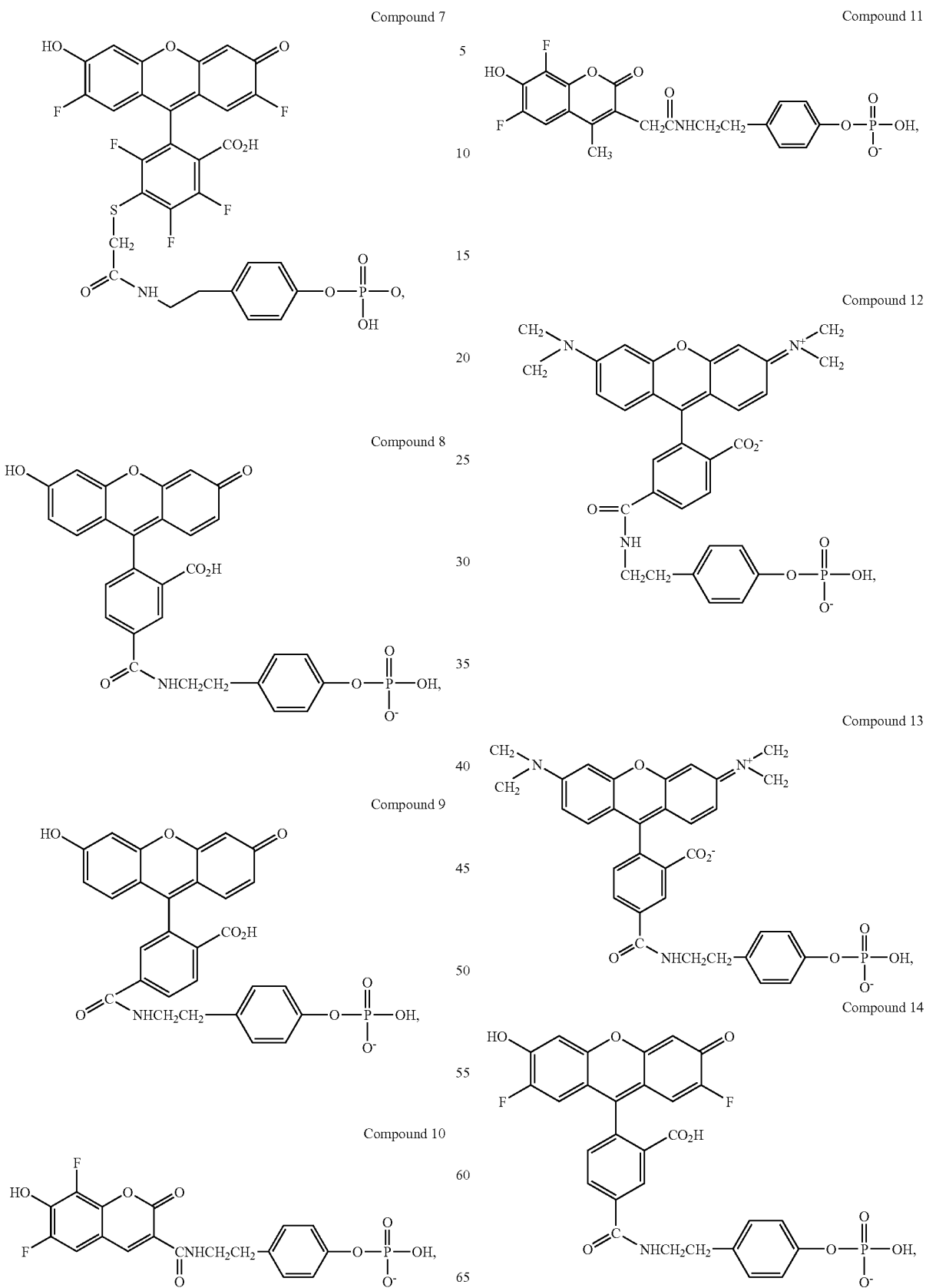

Compound 15
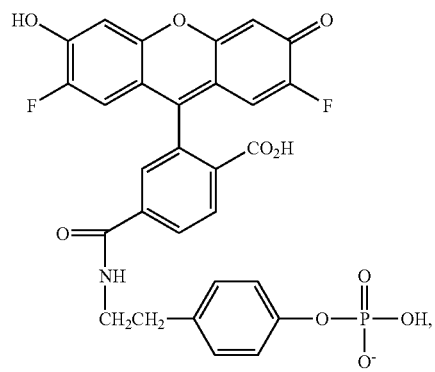
Compound 16
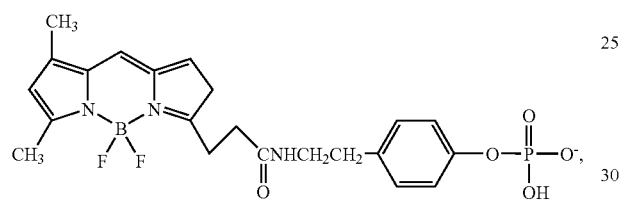
Compound 17
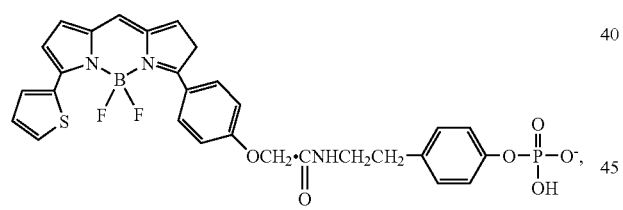
Compound 18
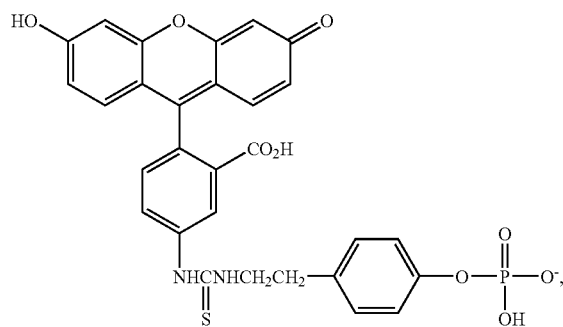
Compound 19
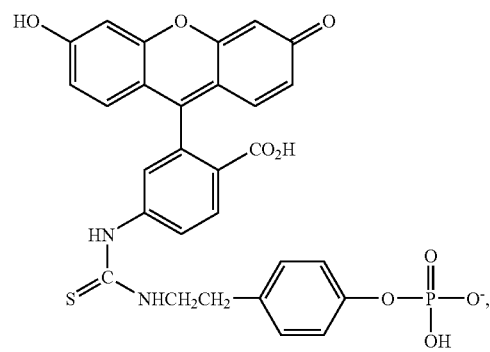
Compound 20
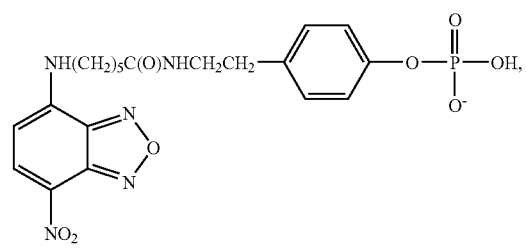
Compound 21
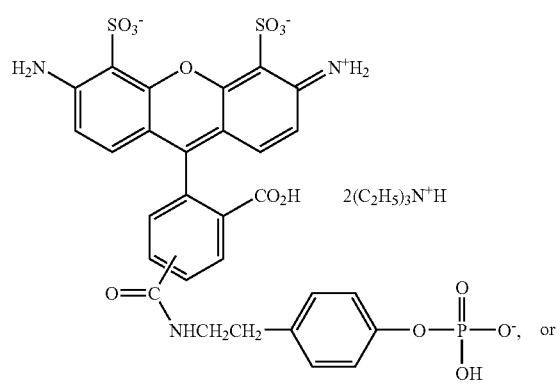
Compound 39
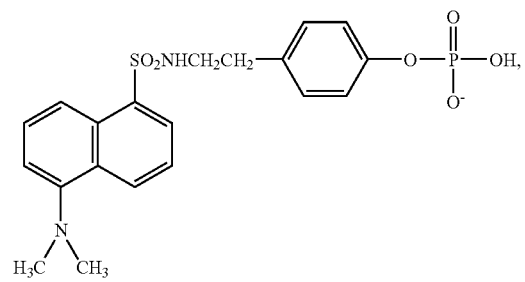
with an appropriate counterion and salts thereof.

6. A method for determining the presence of a phosphorylated target ligand in a sample, in which is employed a ligand-detection reagent comprising a ligand-binding antibody that is capable of binding a phosphotyrosine, phosphoserine or phosphothreonine moiety and a ligand analog that is selected from the group consisting of phosphotyramide, phosphoethanolamine, phosphorylated kinase peptide substrate, phosphatase substrate and phosphorylated peptide to form an antibody-ligand analog complex wherein the ligand analog is covalently bonded to a reporter molecule whereby the amount of generated detectable signal from the reporter molecule is dependent on the presence of the target ligand, the method comprising:

a. generating a ligand-detection comprising a ligand-binding antibody and a ligand analog according to any one of claim 1 wherein the ligand-binding antibody and the ligand analog are incubated together for a sufficient amount of time to form the reagent;

b. incubating the reagent with the sample for a sufficient amount of time for the phosphorylated ligand to displace the ligand analog from a binding groove of the ligand-binding antibody to form a labeled sample;

c. illuminating the labeled sample with an appropriate wavelength wherein the reporter molecule generates a change in detectable signal in the presence of the phosphorylated ligand to form an illuminated sample;

d. observing the illuminated sample whereby the presence or absence of the phosphorylated ligand is determined.

7. The method according to claim 6, wherein the phosphorylated target ligand is selected from the group consisting of proteins, peptides, amino acids, nucleotides, phosphatase substrates, and kinase substrates.

8. The method according to claim 6, wherein the phosphorylated target ligands are immobilized on a solid or semi-solid matrix or are in solution.

9. The method according to claim 8, wherein the solid or semi-solid matrix is a polymeric gel, a membrane, a polymeric particle, a polymeric microparticle or an array.

10. The method according to claim 6, wherein the presence of the target ligand is determined by a shift in color of the detectable signal.

11. The method according to claim 6, wherein the presence of the ligand is determined by an increase in intensity of the detectable signal.

12. The method according to claim 6, wherein the presence of the ligand is determined by a decrease in intensity of the detectable signal.

13. A compound selected from the group consisting of:

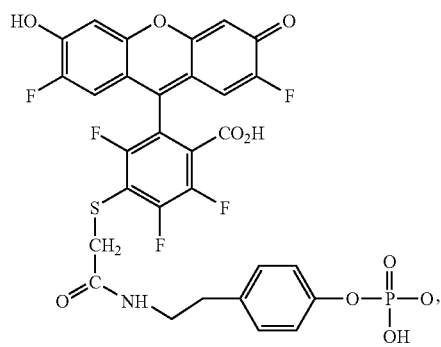

Compound 7

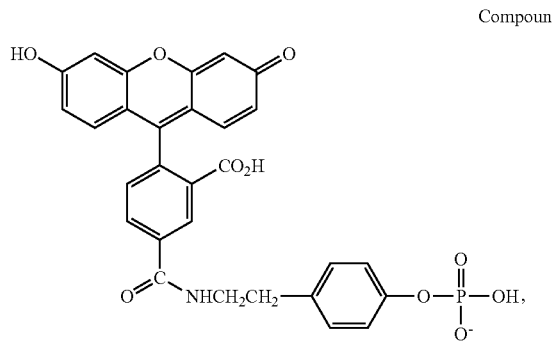

Compound 8

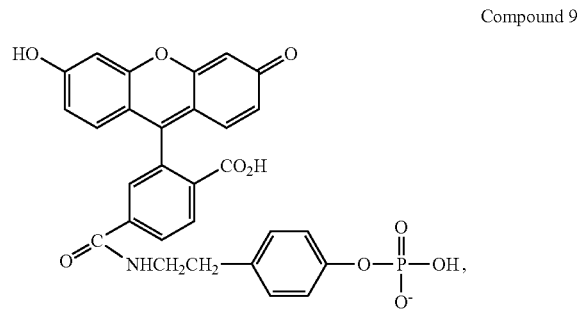

Compound 9

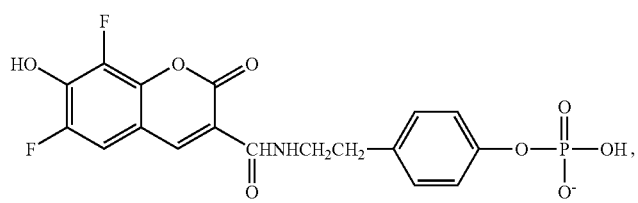

Compound 10

Compound 11
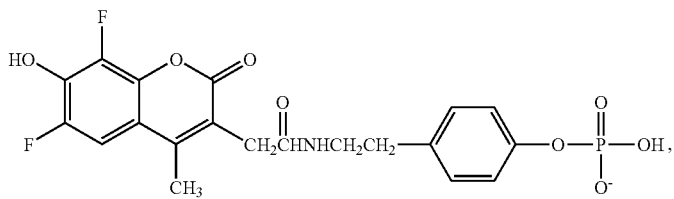
Compound 12
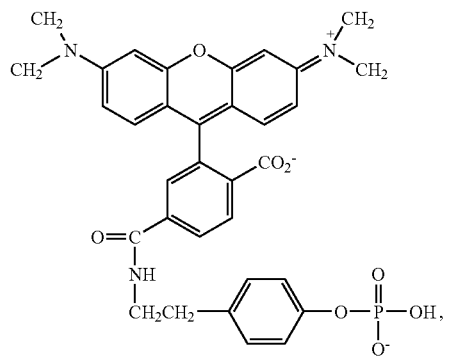
Compound 13
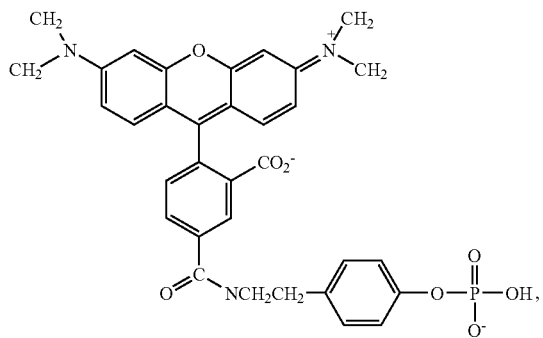
Compound 14
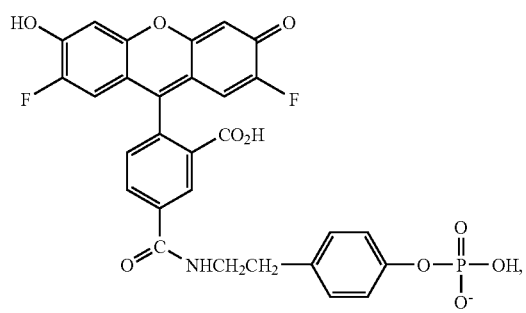
Compound 15
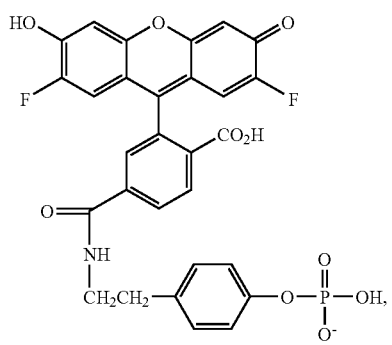
Compound 16
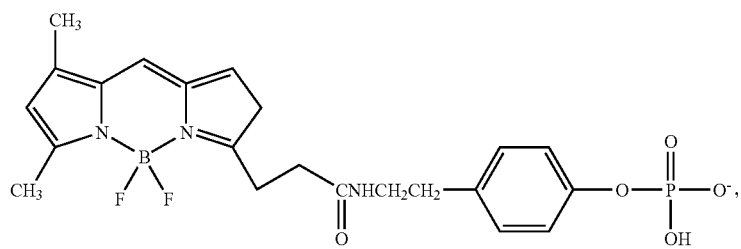
Compound 17
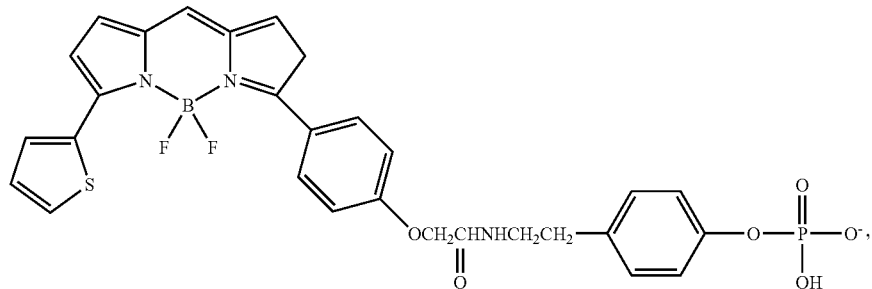

-continued
Compound 18
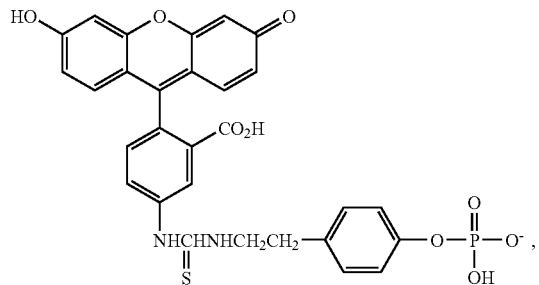
Compound 19
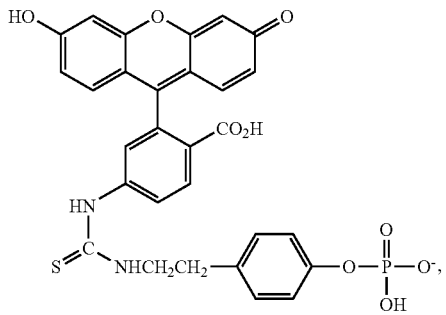
Compound 20
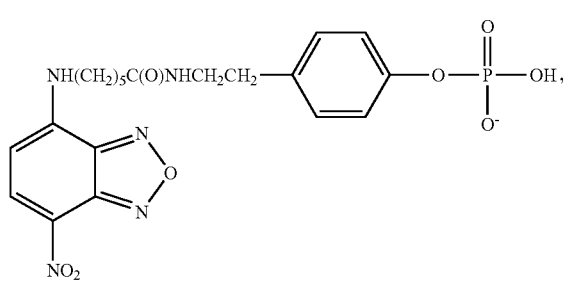
Compound 21
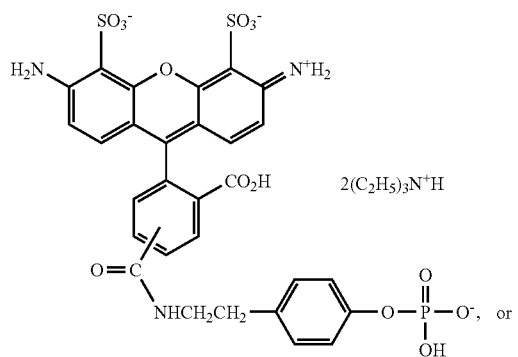
Compound 39
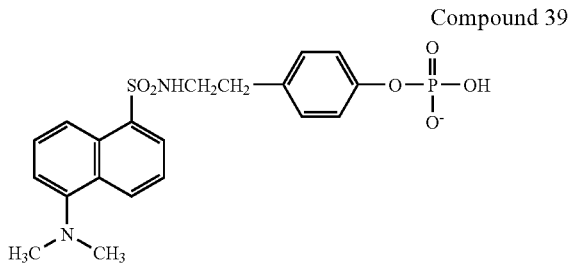
or an appropriate counterion or salt thereof.
* * * * *